US012559450B2

(12) United States Patent
Cigler et al.

(10) Patent No.: US 12,559,450 B2
(45) Date of Patent: Feb. 24, 2026

(54) LIPIDOIDS FOR NUCLEIC ACID TRANSFECTION AND USE THEREOF

(71) Applicant: Ustav Organicke Chemie a Biochemie AV CR, v.v.i., Prague (CZ)

(72) Inventors: Petr Cigler, Prague (CZ); Klara Grantz Saskova, Prague (CZ); Vaclav Vanek, Prague (CZ); Zuzana Kruzikova, Prague (CZ); Frantisek Sedlak, Prague (CZ)

(73) Assignee: Ustav Organicke Chemie a Biochemie AV CR, v.v.i., Prague (CZ)

( * ) Notice: Subject to any disclaimer, the term of this patent is extended or adjusted under 35 U.S.C. 154(b) by 533 days.

(21) Appl. No.: 18/015,254

(22) PCT Filed: Jul. 23, 2021

(86) PCT No.: PCT/CZ2021/050079
§ 371 (c)(1),
(2) Date: Jan. 9, 2023

(87) PCT Pub. No.: WO2022/063350
PCT Pub. Date: Mar. 31, 2022

(65) Prior Publication Data
US 2023/0265049 A1 Aug. 24, 2023

(30) Foreign Application Priority Data
Sep. 23, 2020 (CZ) ................................ CZ2020-529

(51) Int. Cl.

| | |
|---|---|
| ***C07C 233/62*** | (2006.01) |
| ***A61K 9/51*** | (2006.01) |
| ***A61K 48/00*** | (2006.01) |
| ***A61P 43/00*** | (2006.01) |
| ***C12N 15/11*** | (2006.01) |

(52) U.S. Cl.
CPC .......... *C07C 233/62* (2013.01); *A61K 9/5123* (2013.01); *A61K 48/0033* (2013.01); *A61P 43/00* (2018.01); *C12N 15/11* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 3,452,082 | A | 6/1969 | Krimmel |
| 3,534,086 | A | 10/1970 | Narayanan |
| 3,565,942 | A | 2/1971 | Krimmel |
| 3,573,312 | A | 3/1971 | Krimmel |
| 3,624,086 | A | 11/1971 | Krimmel |
| 3,625,985 | A | 12/1971 | Krimmel |
| 3,657,273 | A | 4/1972 | Krimmel |
| 3,663,565 | A | 5/1972 | Krimmel |
| 3,671,527 | A | 6/1972 | Krimmel |
| 3,682,922 | A | 8/1972 | Klimstra |
| 3,704,306 | A | 11/1972 | Krimmel |
| 3,705,141 | A | 12/1972 | Krimmel |
| 3,816,509 | A | 6/1974 | Krimmel |
| 4,448,972 | A | 5/1984 | Pfeiffer |
| 6,511,832 | B1 | 1/2003 | Guarino |
| 7,074,596 | B2 | 7/2006 | Darzynkiewicz |
| 7,288,262 | B1 | 10/2007 | Livoreil |
| 8,058,069 | B2 | 11/2011 | Yaworski |
| 8,323,686 | B2 | 12/2012 | Mirkin |
| 8,329,070 | B2 | 12/2012 | Maclachlan |
| 8,492,359 | B2 | 7/2013 | Yaworski |
| 8,598,333 | B2 | 12/2013 | Maclachlan |
| 8,822,668 | B2 | 9/2014 | Yaworski |
| 9,006,417 | B2 | 4/2015 | Yaworski |
| 9,216,155 | B2 | 12/2015 | Thaxton |

(Continued)

FOREIGN PATENT DOCUMENTS

| | | | |
|---|---|---|---|
| CA | 879102 A | | 8/1971 |
| CN | 102513023 A | * | 6/2012 |

(Continued)

OTHER PUBLICATIONS

CN-102513023-A—English Trans from Google (Year: 2012).*

(Continued)

*Primary Examiner* — Jeffrey S Lundgren
*Assistant Examiner* — Michael J Schmitt
(74) *Attorney, Agent, or Firm* — Riverside Law LLP

(57) ABSTRACT

A lipidoid is disclosed of general formula I (I)

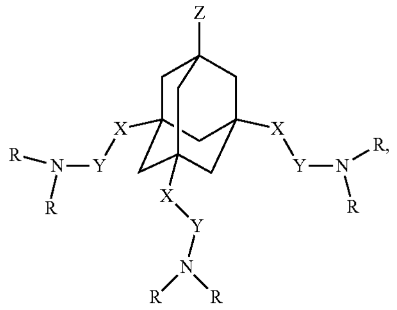

wherein X, Y, Z and R are as defined in the claims.

This lipidoid is useful as a transfection agent. The disclosure further describes transfection agents, transfection particles containing this lipidoid, and their use.

14 Claims, 10 Drawing Sheets

Specification includes a Sequence Listing.

(56) References Cited

U.S. PATENT DOCUMENTS

| | | | |
|---|---|---|---|
| 9,364,435 | B2 | 6/2016 | Yaworski |
| 9,404,127 | B2 | 8/2016 | Yaworski |
| 9,504,651 | B2 | 11/2016 | Maclachlan |
| 9,518,272 | B2 | 12/2016 | Yaworski |
| 9,668,980 | B2 | 6/2017 | Derosa |
| 9,687,448 | B2 | 6/2017 | Akinc |
| 9,872,900 | B2 | 1/2018 | Ciaramella |
| 9,877,919 | B2 | 1/2018 | Derosa |
| 9,878,042 | B2 | 1/2018 | Yaworski |
| 9,974,862 | B2 | 5/2018 | Nishikawa |
| 10,041,091 | B2 | 8/2018 | Cullis |
| 10,137,087 | B2 | 11/2018 | Derosa |
| 10,143,758 | B2 | 12/2018 | Guild |
| 10,201,499 | B2 | 2/2019 | Bell |
| 10,238,754 | B2 | 3/2019 | Guild |
| 10,238,756 | B2 | 3/2019 | Ho |
| 10,325,026 | B2 | 6/2019 | Cardillo |
| 10,369,122 | B2 | 8/2019 | Dong |
| 10,369,226 | B2 | 8/2019 | Maier |
| 10,471,153 | B2 | 11/2019 | Derosa |
| 10,487,332 | B2 | 11/2019 | Geall |
| 10,507,183 | B2 | 12/2019 | Guild |
| 10,626,393 | B2 | 4/2020 | Lee |
| 10,709,779 | B2 | 7/2020 | Ciaramella |
| 10,933,127 | B2 | 3/2021 | Ciaramella |
| 11,045,418 | B2 | 6/2021 | Hefesha |
| 11,141,378 | B2 | 10/2021 | Yaworski |
| 11,246,933 | B1 | 2/2022 | Maier |
| 11,291,682 | B2 | 4/2022 | Geall |
| 11,342,770 | B2 | 5/2022 | Liu |
| 11,357,726 | B2 | 6/2022 | Karve |
| 11,382,979 | B2 | 7/2022 | Maier |
| 11,395,799 | B2 | 7/2022 | Haas |
| 11,446,383 | B2 | 9/2022 | Yaworski |
| 11,471,525 | B2 | 10/2022 | Rauch |
| 11,524,023 | B2 | 12/2022 | Packer |
| 11,583,504 | B2 | 2/2023 | Brader |
| 11,590,229 | B2 | 2/2023 | Maier |
| 11,591,544 | B2 | 2/2023 | Drummond |
| 11,596,645 | B2 | 3/2023 | Geall |
| 11,612,657 | B2 | 3/2023 | Maier |
| 11,633,479 | B2 | 4/2023 | Maier |
| 11,633,480 | B2 | 4/2023 | Maier |
| 11,638,693 | B2 | 5/2023 | Geall |
| 11,638,694 | B2 | 5/2023 | Geall |
| 11,655,475 | B2 | 5/2023 | Geall |
| 11,666,534 | B2 | 6/2023 | Geall |
| 11,679,159 | B2 | 6/2023 | Anitha |
| 11,690,862 | B1 | 7/2023 | Geall |
| 11,707,482 | B2 | 7/2023 | Geall |
| 11,718,852 | B2 | 8/2023 | Yaworski |
| 11,766,401 | B2 | 9/2023 | Geall |
| 11,771,652 | B2 | 10/2023 | Casimiro |
| 11,786,467 | B2 | 10/2023 | Geall |
| 11,786,598 | B2 | 10/2023 | Yaworski |
| 11,839,686 | B2 | 12/2023 | Geall |
| 11,850,305 | B2 | 12/2023 | Geall |
| 11,857,681 | B2 | 1/2024 | Geall |
| 11,865,190 | B2 | 1/2024 | Leavitt |
| 11,883,534 | B2 | 1/2024 | Geall |
| 11,938,227 | B2 | 3/2024 | Bao |
| 11,951,177 | B2 | 4/2024 | An |
| 12,011,507 | B2 | 6/2024 | Kurek |
| 12,016,929 | B2 | 6/2024 | Yaworski |
| 12,059,498 | B2 | 8/2024 | Haas |
| 12,064,479 | B2 | 8/2024 | Drummond |
| 12,064,515 | B2 | 8/2024 | Karve |
| 12,077,725 | B2 | 9/2024 | Drummond |
| 2005/0245534 | A1 | 11/2005 | Link |
| 2012/0172411 | A1 | 7/2012 | Heyes |
| 2012/0295832 | A1 | 11/2012 | Constien |
| 2015/0018436 | A1 | 1/2015 | Drasar |
| 2016/0151284 | A1 | 6/2016 | Heyes |
| 2016/0256567 | A1 | 9/2016 | Heyes |
| 2016/0376224 | A1 | 12/2016 | Du |
| 2018/0043320 | A1 | 2/2018 | Ramsay |
| 2018/0221510 | A1 | 8/2018 | Manoharan |
| 2018/0311176 | A1 | 11/2018 | Ozsolak |
| 2018/0311343 | A1 | 11/2018 | Huang |
| 2019/0002609 | A1 | 1/2019 | Klein |
| 2019/0032051 | A1 | 1/2019 | Yaworski |
| 2019/0076358 | A1 | 3/2019 | Ishihara |
| 2019/0106379 | A1 | 4/2019 | Heyes |
| 2019/0374466 | A1 | 12/2019 | Klein |
| 2020/0308603 | A1 | 10/2020 | Stewart |
| 2020/0330607 | A1 | 10/2020 | Dahlman |
| 2021/0059953 | A1 | 3/2021 | Kotin |
| 2021/0171521 | A1 | 6/2021 | Plewe |
| 2021/0346306 | A1 | 11/2021 | Dimitrov |
| 2021/0353556 | A1 | 11/2021 | Karve |
| 2021/0378962 | A1 | 12/2021 | Karve |
| 2021/0378980 | A1 | 12/2021 | Horhota |
| 2022/0001025 | A1 | 1/2022 | Barz |
| 2022/0016029 | A1 | 1/2022 | Karve |
| 2022/0047519 | A1 | 2/2022 | Sagi |
| 2022/0062175 | A1 | 3/2022 | Smith |
| 2022/0071905 | A1 | 3/2022 | Karve |
| 2022/0110884 | A1 | 4/2022 | Karve |
| 2022/0133631 | A1 | 5/2022 | Shah |
| 2022/0162552 | A1 | 5/2022 | Thomas |
| 2022/0168222 | A1 | 6/2022 | Heyes |
| 2022/0280427 | A1 | 9/2022 | Su |
| 2022/0280639 | A1 | 9/2022 | Huang |
| 2022/0287966 | A1 | 9/2022 | Karve |
| 2022/0296517 | A1 | 9/2022 | Benenato |
| 2022/0370624 | A1 | 11/2022 | Rajappan |
| 2022/0381748 | A1 | 12/2022 | Haas |
| 2022/0395589 | A1 | 12/2022 | Green |
| 2022/0396548 | A1 | 12/2022 | Jain |
| 2023/0000781 | A1 | 1/2023 | Derosa |
| 2023/0097090 | A1 | 3/2023 | Tam |
| 2023/0099898 | A1 | 3/2023 | Heinrich |
| 2023/0159449 | A1 | 5/2023 | Perez-Garcia |
| 2023/0241002 | A1 | 8/2023 | Smith |
| 2023/0241223 | A1 | 8/2023 | Heinrich |
| 2023/0277457 | A1 | 9/2023 | Shepard |
| 2023/0285297 | A1 | 9/2023 | Smith |
| 2023/0285310 | A1 | 9/2023 | Cadete Pires |
| 2023/0302153 | A1 | 9/2023 | An |
| 2023/0364024 | A1 | 11/2023 | Brader |
| 2023/0372537 | A1 | 11/2023 | Hope |
| 2023/0398076 | A1 | 12/2023 | Karmali |
| 2023/0398082 | A1 | 12/2023 | Kurek |
| 2023/0414516 | A1 | 12/2023 | Bhatnagar |
| 2023/0414747 | A1 | 12/2023 | Panzner |
| 2024/0009131 | A1 | 1/2024 | Schariter |
| 2024/0009238 | A1 | 1/2024 | Sahin |
| 2024/0024422 | A1 | 1/2024 | Frederick |
| 2024/0041785 | A1 | 2/2024 | Panzner |
| 2024/0110214 | A1 | 4/2024 | Ziegenhals |
| 2024/0123035 | A1 | 4/2024 | De Fougerolles |
| 2024/0131193 | A1 | 4/2024 | De Fougerolles |
| 2024/0148794 | A1 | 5/2024 | Alvarez |
| 2024/0197636 | A1 | 6/2024 | Patil |
| 2024/0216291 | A1 | 7/2024 | Van Der Meel |
| 2024/0229034 | A1 | 7/2024 | Morris |
| 2024/0238211 | A1 | 7/2024 | Brader |
| 2024/0269323 | A1 | 8/2024 | Kulkarni |

FOREIGN PATENT DOCUMENTS

| | | | |
|---|---|---|---|
| EP | 3156077 | A1 | 4/2017 |
| EP | 3192788 | A1 | 7/2017 |
| EP | 3604533 | A1 | 2/2020 |
| GB | 1310652 | A | 3/1973 |
| WO | 2008042973 | A2 | 4/2008 |
| WO | 2011071860 | A2 | 6/2011 |
| WO | 2011141705 | A1 | 11/2011 |
| WO | 2013086354 | A1 | 6/2013 |
| WO | 2013126803 | A1 | 8/2013 |
| WO | 2015199952 | A1 | 12/2015 |
| WO | 2015200465 | A1 | 12/2015 |
| WO | 2016187531 | A1 | 11/2016 |
| WO | 2017008076 | A1 | 1/2017 |

(56) References Cited

FOREIGN PATENT DOCUMENTS

| | | | |
|---|---|---|---|
| WO | 2017019891 | A2 | 2/2017 |
| WO | 2017117528 | A1 | 7/2017 |
| WO | 2017176974 | A1 | 10/2017 |
| WO | 2018081480 | A1 | 5/2018 |
| WO | 2018087753 | A1 | 5/2018 |
| WO | 2019099501 | A1 | 5/2019 |
| WO | 2020070040 | A1 | 4/2020 |
| WO | 2020072324 | A1 | 4/2020 |
| WO | 2020077007 | A1 | 4/2020 |
| WO | 2020097520 | A1 | 5/2020 |
| WO | 2020097548 | A1 | 5/2020 |
| WO | 2020185293 | A1 | 9/2020 |
| WO | 2020227642 | A1 | 11/2020 |
| WO | 2020247604 | A1 | 12/2020 |
| WO | 2021021634 | A1 | 2/2021 |
| WO | 2021026358 | A1 | 2/2021 |
| WO | 2021113365 | A1 | 6/2021 |
| WO | 2022011156 | A1 | 1/2022 |
| WO | 2022063350 | A1 | 3/2022 |
| WO | 2022132926 | A1 | 6/2022 |
| WO | 2022159475 | A1 | 7/2022 |
| WO | 2022225918 | A1 | 10/2022 |
| WO | 2022251953 | A1 | 12/2022 |
| WO | 2022251959 | A1 | 12/2022 |
| WO | 2023001323 | A1 | 1/2023 |
| WO | 2023009421 | A1 | 2/2023 |
| WO | 2023009422 | A1 | 2/2023 |
| WO | 2023021427 | A1 | 2/2023 |
| WO | 2023031392 | A1 | 3/2023 |
| WO | 2023043038 | A1 | 3/2023 |
| WO | 2023205628 | A1 | 10/2023 |
| WO | 2023220815 | A1 | 11/2023 |
| WO | 2023239756 | A1 | 12/2023 |
| WO | 2024006863 | A1 | 1/2024 |
| WO | 2024026475 | A1 | 2/2024 |
| WO | 2024086929 | A1 | 5/2024 |
| WO | 2024119276 | A1 | 6/2024 |
| WO | 2024133635 | A1 | 6/2024 |
| WO | 2024136626 | A1 | 6/2024 |

OTHER PUBLICATIONS

Grillaud et al. “Polycationic Adamantane-Based Dendrons of Different Generations Display High Cellular Uptake without Triggering Cytotoxicity,” J. Am. Chem. Soc. 2014, 136, 810-819. (Year: 2014).*

Li, Bin, et al.; “An Orthogonal Array Optimization of Lipid-Like Nanoparticles for mRNA Delivery in Vivo”; NANO Letters 2015; 15(12):8099-8107.

Grillaud, Maxime, et al.; “Polycationic Adamantane-Based Dendrons of Different Generations Display High Cellular Uptake without Triggering Cytotoxicity”; Journal of the American Chemical Society 2014; 136(2):810-819.

International Search Report and Written Opinion for PCT Application No. PCT/CZ2021/050079 mailed Feb. 2, 2022.

International Application Status Report generated Mar. 31, 2022.

* cited by examiner

1a, n=1
b, n=2
c, n=3
d, n=4
e, n=5
f, n=6
g, n=7

2a, n=1
b, n=2
c, n=3
d, n=4
e, n=5
f, n=6
g, n=7

3a, n=1
b, n=2
c, n=3
d, n=4
e, n=5
f, n=6
g, n=7

4a, n=1
b, n=2
c, n=3
d, n=4
e, n=5
f, n=6
g, n=7

19

20

21

22

| | n | m |
|---|---|---|
| 26a | 2 | 4 |
| b | 3 | 3 |
| c | 2 | 6 |
| d | 3 | 5 |

| | n | m |
|---|---|---|
| 30a | 2 | 4 |
| b | 3 | 3 |
| c | 2 | 6 |
| d | 3 | 5 |

| | n | m |
|---|---|---|
| 31a | 2 | 4 |
| b | 3 | 3 |
| c | 2 | 6 |
| d | 3 | 5 |

LIPIDOIDS FOR NUCLEIC ACID TRANSFECTION AND USE THEREOF

FIELD OF ART

The invention relates to novel ionizable lipidoids and to the use of these compounds for transfection and administration of nucleotides and nucleic acids and their synthetic analogues into cells and tissues.

BACKGROUND ART

The development of nucleic acid (NA)-based therapies has experienced an unprecedented renaissance in recent years. Due to the high efficacy and at the same time the low risk of adverse side effects compared to previously tested therapeutic deoxyribonucleic acids (DNA), ribonucleic acid (RNA) therapies are now gaining ground. Several such drugs have already reached clinical use, for example patisiran for hereditary transthyretin amyloidosis, eteplirsen for certain types of Duchenne muscular dystrophy, or nusinersen for the treatment of spinal muscular atrophy. All of these diseases are life-threatening and there is no alternative treatment for them. Potential drugs targeting ribonucleic acid (RNA) or its use can be divided into three categories according to whether they target NA or proteins or encode proteins. The first category includes single-stranded antisense oligonucleotides of 13-25 nucleotides (nt) that block the translation of messenger RNA (mRNA) or RNA splicing (nusinersen, eteplirsen); and small interfering RNAs (siRNA, 21-23 nt) that degrade mRNA (patisiran). Therapeutic RNA molecules targeting proteins use a type of molecule known as an RNA aptamer. It is designed to modulate the function of a particular protein. An example of such a drug is pegaptanib, used to treat neovascular age-related macular degeneration, which was the first approved drug of its kind in 2004. Therapies using mRNA are mainly used for the preparation of so-called personalized vaccines against cancer or vaccines against infectious diseases (eg. Zika virus, SARS-CoV-2). It is in viral diseases that candidates for a prophylactic vaccine based on mRNA against rabies and pandemic influenza have been shown to induce safe antibody production in healthy volunteers. Enormous efforts have been put into vaccine development against Severe Acute Respiratory Syndrome Coronavirus 2 (SARS-CoV-2), the virus responsible for the COVID-19 pandemic. These efforts led to safe and highly effective mRNA vaccine candidates that are now being distributed for widespread use. Protein-replacing mRNA therapies are also in the preclinical stages of development, for example for treating hemophilia.

Molecular technologies enabling direct genome editing, especially those based on the CRISPR-Cas9 system, are now booming. CRISPR technology is a tool that allows you to change DNA sequences and modify gene function. Potential applications include the repair of genetic defects, the treatment and prevention of the spread of diseases or the improvement of agricultural crops. The CRISPR-Cas9 system has been tested in a number of preclinical and clinical studies including HIV treatment, the treatment of hematological malignancies and genetic disorders, including sickle cell disease and p-thalassemia. RNA editing is then enabled by the system of ADARs (adenosine deaminase acting on RNA), which so far seems to be safer from a clinical point of view. Molecular technologies for direct genome editing can be delivered to the site of action in the form of mRNA that encodes the appropriate enzyme responsible for editing.

A key factor enabling the safe use of all the above technologies (or others, based on NA) is their safe and efficient transport to the site of action. The critical step is the penetration of negatively charged NAs through the phospholipid membrane of the cell; the process of deliberately introducing NAs into eukaryotic cells is called transfection. In recent decades, there has been an intensive development of carriers (so-called vectors) to efficiently transport NA across the cell membrane while protecting NA from degradation in vivo (Stewart, M. P.: *Chem. Rev.* 2018, 118, 7409-7531).

Both viral and non-viral (physical, chemical) vectors are used for NA transfection. Although approximately 70% of clinical trials in the field of gene therapy have so far been performed using viral vectors, this approach carries numerous risks (carcinogenicity, induction of an immune response, tissue non-specificity, limited NA incorporation capacity and manufacturing complexity). Physical methods (eg. electroporation) are difficult to use systemically in human medicine.

In contrast, synthetic chemical vectors usually have lower immunogenicity, are able to transport larger amounts of genetic material, and because they are composed of well-defined molecules, their structure can be influenced as needed to increase their efficiency and suppress toxicity. Cationic polymers or cationic lipids are used as chemical vectors, which form a complex with negatively charged NA. This complex is able to penetrate the cell membrane and at the same time protects NA from degradation in the extracellular environment.

From a structural point of view, so-called lipid nanoparticles (LNPs) are currently the most promising and clinically advanced form of these complexes. In them, cationic lipids are usually formulated with a PEGylated lipid that prevents aggregation, affects particle size and transfection efficiency, with helper lipid and cholesterol, which are necessary for stable NK encapsulation, as shown, for example, in an siRNA transfection system (Kulkarni, J.: *Nanoscale,* 2019, 11, 21733-21739). LNPs can accommodate NA molecules ranging in size from a few nucleotide units to millions.

Synthetic cationic lipids and lipidoids (synthetic molecules similar to lipids differing in a large number of hydrophobic chains) are formed by a cationic and a hydrophobic domain. To date, a large number of these substances have been developed with high structural variability in both domains, both by targeted design and by testing combinatorially generated libraries.

Lipids and lipidoids such as D-Lin-MC3-DMA, C12-200, cKK-E12, SA2-SC8 and others have been specially developed for siRNA transfection (Dong, Y.: *Adv. Drug Deliv. Rev.* 2019, 144, 133-147). A formulation containing D-Lin-MC3-DMA was recently (August 2018) introduced into clinical practice under the name Onpattro (formerly Patisiran), making it the first approved siRNA drug in history (Zhang, X.: *J. Clin. Pharmacol.* 2020, 60 (1), 37-49). However, formulations developed for siRNA may not be effective for mRNA, and targeted optimization is therefore necessary (Cullis, P.: *Mol. Ther.* 2017, 25 (7), 1467-1475).

Ionizable lipids and lipidoids such as D-Lin-MC3-DMA, C12-200, cKK-E12, and TT3 are used to transfect mRNA (Zhong, Z.: *Nano Today* 2018, 23, 16-39; Kowalski, P.: *Mol. Ther.* 2019, 27(4), 1-19; Li, B.: *Nano Lett.* 2015, 15, 8099-8107). Ionizable lipids are also used for DNA transfection. Again, it should be emphasized that transfection systems optimized for small molecule (siRNA) transfection are not always suitable for DNA transfection, and even formulations developed for mRNA may not be effective for DNA (Buck, J.: *ACS Nano* 2019, 13, 3754-3782).

Due to the fact that despite their enormous therapeutic potential, very few synthetic vectors based on ionizable lipids have been brought to the stage of clinical use so far, it is necessary to develop new systems with higher efficiency, which would also have very low in vivo toxicity.

DISCLOSURE OF THE INVENTION

The present invention provides a solution to the problem of the efficiency of transfection and targeted delivery of nucleotides and nucleic acids and their synthetic analogs using ionizable (cationic) lipids and the problem of the toxicity of these lipids to the target organism or cell. We have surprisingly found that if adamantane is used as the central core of the ionizable lipidoid, the transfection efficiency of such lipidoids is significantly increased compared to previously known solutions, especially in the transfection of mRNA, cyclic dinucleotides, siRNA and DNA. At the same time, these adamantane-containing lipidoids exhibit extremely low cytotoxicity at relevant doses. They show no signs of toxicity in mice after intravenous or intraperitoneal administration. A specific property of the adamantane core, used as the central structural motif of the new ionizable lipidoids, is steric complexity in its vicinity and a high rigidity in comparison with the ionizable lipids and lipidoids known so far. A further advantage of bioactive substances structurally derived from adamantane is generally good biocompatibility, and thus suitability for pharmaceutical use, in particular in human medicine.

The invention relates to ionizable lipidoids of general formula I (I)

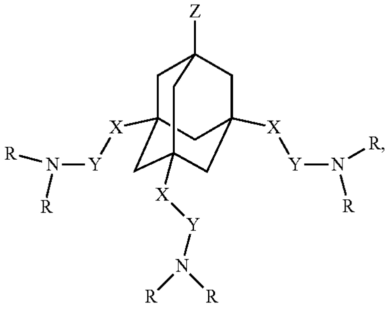

wherein X is selected from a group consisting of —C(═O)NH—, —C(═O)O—, —C(═S)O—, —C(═O)S—, —C(═S)S—, —C(═O)NHNH—, —$CH_2$—, —O—, —OC(═O)—, —S—, —SC(═O)—, —NH—, —NHNH—, —NHC(═O)—, —NHNHC(═O)—, —C≡C—, —CH═CH—, a five-membered heterocycle containing at least 2 nitrogen atoms, —$CH_2$C(═O)NH—, —$CH_2$C(═O)O—, —$CH_2$C(═S)O—, —$CH_2$C(═S)S—, —$CH_2$C(═O)NHNH—, —N═CH—, and —CH═N—;

Y is independently selected from a group consisting of alkylene chains $C_2$-$C_{10}$, wherein in the said alkylene chain, one or more —$CH_2$— groups may optionally be replaced with one or more O or S atoms;

Z is selected from the group consisting of hydrogen, —OH, —$CH_2$OH, —$NH_2$, —$N^+(CH_3)_2$—$(CH_2)_3$—$SO_3^-$, —$N^+(CH_3)_2$—$(CH_2)_2$—$COO^-$, and —$NHCH_3$, —$N(CH_3)_2$, —$N^+(CH_3)_3$, —$OCH_3$, —$OCH_2CH_3$, —C(═O)$R^1$, wherein $R^1$ is selected from —$NH_2$, —NH$(CH_2)_n$OH, —N[$(CH_2)_n$OH$]_2$, —NHCH$(CH_2OH)_2$, —$NHCH_2$CH(—OH)$CH_2$OH, —NH$(CH_2)_n$C(═O)$NH_2$, —N[$CH_2$C(═O)$NH_2]_2$, —NHCH[C(═O)$NH_2]_2$, —NH$(CH_2)_2$NHC(═O)$NH_2$,

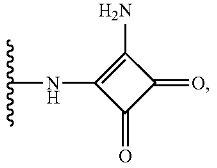

and

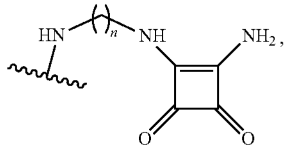

wherein n is an integer within the range from 2 to 5;

and R are the same or different from each other, each R being independently selected from the group consisting of alkyl $C_8$-$C_{20}$, alkenyl $C_8$-$C_{20}$, and alkynyl $C_8$-$C_{20}$, wherein in the said alkyl, alkenyl or alkynyl, one or more —$CH_2$— groups may optionally be replaced with one or more groups selected from —CH(OH)—, —OC(═O)—, —C(═O)O—, —S—S—, —C(═O)NH—, —NHC(═O)—, —O—, and —S—;

and pharmaceutically acceptable salts, addition salts and solvates thereof.

In some embodiments, X is selected from a group consisting of —C(═O)NH—, —C(═O)O—, —C(═S)O—, —C(═O)S—, —C(═S)S—, —C(═O)NHNH—, —$CH_2$—, —O—, —S—, —NH—, —NHNH—, —NHC(═O)—, —NHNHC(═O)—, —C≡C—, —CH═CH—, five-membered heterocycle comprising at least two nitrogen atoms, —$CH_2$C(═O)NH—, —$CH_2$C(═O)O—, $CH_2$C(═S)O—, $CH_2$C(═S)S—, —$CH_2$C(═O)NHNH—, —N═CH—, —CH═N—.

In some embodiments, Y is selected from a group consisting of alkylene chains $C_2$-$C_{10}$.

In some embodiments, Z is selected from a group consisting of hydrogen atom, —OH, —$NH_2$, —$NHCH_3$, —$N(CH_3)_2$, —$N^+(CH_3)_3$, —$OCH_3$, —$OCH_2CH_3$, —$N^+(CH_3)_2$—$(CH_2)_3$—$SO_3^-$, —$N^+(CH_3)_2$—$(CH_2)_2$—$COO^-$.

In some embodiments, Z is selected from a group consisting of hydrogen, —OH, —$CH_2$OH, —$NH_2$, —$N^+(CH_3)_2$—$(CH_2)_3$—$SO_3^-$, —$N^+(CH_3)_2$—$(CH_2)_2$—$COO^-$, and —C(═O)$R^1$, wherein $R^1$ is selected from —$NH_2$, —NH$(CH_2)_n$OH, —N[$(CH_2)_n$OH$]_2$, —NHCH$(CH_2OH)_2$, —$NHCH_2$CH(OH)$CH_2$OH, —NH$(CH_2)_n$C(═O)$NH_2$, —N[$CH_2$C(═O)$NH_2]_2$, —NHCH[C(═O)$NH_2]_2$, —NH$(CH_2)_2$NHC(═O)$NH_2$,

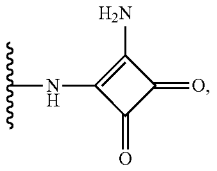

and

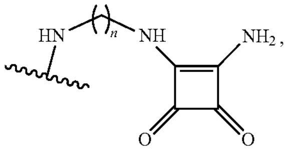

wherein n is an integer within the range from 2 to 5.

In some embodiments, Z is selected from a group consisting of hydrogen, —OH, —$CH_2$OH, —$NH_2$, —$N^+(CH_3)_2$—$(CH_2)_3$—$SO_3^-$, —$N^+(CH_3)_2$—$(CH_2)_2$—$COO^-$, and —C(═O)$R^1$, wherein $R^1$ is selected from $-NH_2$, $-NH(CH_2)_2OH$, $-N[(CH_2)_2OH]_2$, $-NHCH(CH_2OH)_2$, $-NHCH_2CH(-OH)CH_2OH$, $-NH(CH_2)_2C(=O)NH_2$, $-N[CH_2C(=O)NH_2]_2$, $-NHCH[C(=O)NH_2]_2$, $-NH(CH_2)_2NHC(=O)NH_2$,

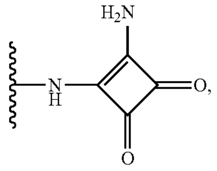

and

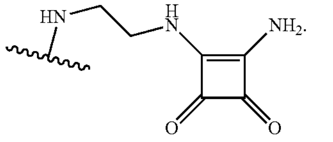

The term "alkyl" means a saturated hydrocarbon chain, which may be straight, branched or cyclic or cycle-containing.

The term "alkenyl" means a hydrocarbon chain containing at least one double bond between carbon atoms. The hydrocarbon chain may be straight, branched or cyclic or cycle-containing.

The term "alkynyl" means a hydrocarbon chain containing at least one triple bond between carbon atoms, and optionally further one or more double bonds between carbon atoms. The hydrocarbon chain may be straight, branched or cyclic or cycle-containing.

The term "alkylene chain" means a saturated hydrocarbon chain, which may be straight, branched or cyclic or cycle-containing, but is preferably straight. This chain has two valencies, i.e. it binds as a linker or bridge via two bonds.

When the molecule of general formula I has a positive charge, the compound includes a counterion, which may be a pharmaceutically acceptable anion of an organic or inorganic acid, to form a pharmaceutically acceptable salt. Such an anion may be selected, for example, from the group consisting of acetate, aspartate, benzesulphonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, iodide, lactate, malate, maleate, mandelate, mesylate, methanesulphate, napsylate, nitrate, octanoate, oleate, palmoate, pantothenate, phosphate, polygalacturonate, propionate, salicylate, stearate, succinate, sulphate, tartrate, and tosylate.

When the compound of formula I contains chiral centers, then the formula I includes pure enantiomers as well as mixtures of enantiomers, including the racemate.

Formula I includes compounds of formula I in free form, as well as in the form of salts, addition salts (with acids or bases) and/or solvates, including hydrates or alcohol solvates.

The linker X in the formula I is formed by the reaction of attachment of the amine moieties of the molecule to the central adamantane core. These may therefore be different linkers, depending on the reaction chosen, e.g. the formation of ester, amide and their analogues, click reaction (e.g. azido-alkyne cycloaddition), etc. X is thus selected from the group consisting of $-C(=O)NH-$, $-C(=O)O-$, $-C(=S)O-$, $-C(=O)S-$, $-C(=S)S-$, $-C(=O)NHNH-$, $-CH_2-$, $-O-$, $-OC(=O)-$, $-S-$, $-SC(=O)-$, $-NH-$, $-NHNH-$, $-NHC(=O)-$, $-NHNHC(=O)-$, $-C\equiv C-$, $-CH=CH-$, a five-membered heterocycle containing at least 2 nitrogen atoms, $-CH_2C(=O)NH-$, $-CH_2C(=O)O-$, $-CH_2C(=S)O-$, $-CH_2C(=S)S-$, $-CH_2C(=O)NHNH-$, $-N=CH-$, and $-CH=N-$. Preferably, X is selected from $-C(=O)NH-$, a five membered heterocycle containing at least 2 nitrogen atoms, and $-C(=O)O-$.

The linker Y is an alkylene chain providing at least a minimum distance of the amine from the linker X and the adamantane core. Y is a $C_2$-$C_{10}$ alkylene chain, preferably $C_2$-$C_8$ alkylene chain, wherein in the said alkylene chain, one or more $-CH_2-$ groups may optionally be replaced with one or more O or S atoms.

The substituent Z may further modify the properties of the compound of formula I to a small extent.

Preferably, Z is a hydrogen atom or $-C(=O)R^1$. The moiety $-C(=O)R^1$ is typically formed by a reaction of an amine-terminated molecule with the central adamantane core bearing a carboxylic acid group. $R^1$ is thus selected from the group consisting of $-NH_2$, $-NH(CH_2)_nOH$, $-N[(CH_2)_nOH]_2$, $-NHCH(CH_2OH)_2$, $-NHCH_2CH(-OH)CH_2OH$, $-NH(CH_2)_nC(=O)NH_2$, $-N[CH_2C(=O)NH_2]_2$, $-NHCH[C(=O)NH_2]_2$, $-NH(CH_2)_2NHC(=O)NH_2$,

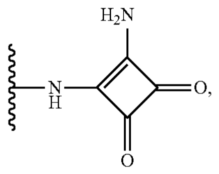

and

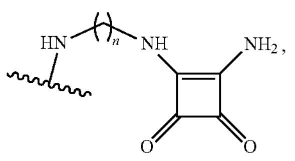

wherein n is an integer within the range from 2 to 5.

Preferably, $R^1$ is selected from $-NH_2$, $-NH(CH_2)_2OH$, $-NHCH(CH_2OH)_2$.

The R chains may be the same or different from each other, preferably they are the same, or all nitrogen atoms are substituted identically (with two identical Rs or two different Rs), for synthetic simplicity. R substituents are fatty chains, and they are selected from the group consisting of $C_8$-$C_{20}$ alkyl, $C_8$-$C_{20}$ alkenyl, and $C_8$-$C_{20}$ alkynyl, wherein in the said alkyl, alkenyl or alkynyl, one or more $-CH_2-$ groups may optionally be replaced by one or more groups selected from $-CH(OH)-$, $-OC(=O)-$, $-C(=O)O-$, $-SS-$, $-C(=O)NH-$, $-NHC(=O)-$, $-O-$, and $-S-$. Preferably, substituents R are selected from a group consisting of $C_8$-$C_{20}$ alkyl, $C_8$-$C_{20}$ alkenyl, and $C_8$-$C_{20}$ alkynyl, wherein in the said alkyl, alkenyl or alkynyl, one or more $-CH_2-$ groups may optionally be replaced by one or more groups selected from $-CH(OH)-$, $-OC(=O)-$, and $-C(=O)O-$.

Preferably, R is selected from $C_{10}$-$C_{16}$ alkyl, $C_{10}$-$C_{16}$ alkyl in which $-CH_2-$ group is replaced with $-CH(OH)-$ or $-C(=O)O-$, $C_{14}$-$C_{20}$ alkenyl with one or two or three double bonds, $C_{14}$-$C_{20}$ alkenyl with one or two or three double bonds in which $-CH_2-$ group is replaced by $-C(=O)O-$ or $-CH(OH)-$.

Compounds of formula I are prepared by the corresponding reaction of an adamantane precursor substituted with group Z in position 7 and precursor groups of linker X in positions 1, 3, 5 with an amine of general formula X'—Y—$NR_2$, wherein X' is a precursor group of the linker X. The amine can be prepared by reactions and procedures known to those skilled in the art, and suitable amines are also commercially available.

In a more specific example, the compounds of formula I are preferably prepared by reacting a compound of formula II (II)

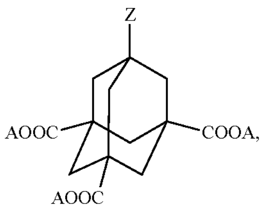

wherein A is hydrogen, with a diamine of formula III (III)

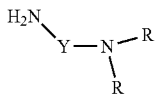

in the presence of a condensing agent and a base, or by reacting a compound of general formula II wherein A is a halogen, with a diamine of general formula III in the presence of a base.

In formulas II and III, Z, Y and R are as described above.

The present invention also relates to a transfection agent comprising at least one lipidoid of general formula I, and at least one helper lipid. The transfection agent can be prepared by combining the components. Transfection agent in the form of a solution may be prepared by dissolving and mixing the components. Transfection agent in solid form (particulate form, preferably nanoparticulate form) can be prepared by means of techniques used in conventional nanoparticle technology, for example, by microfluidic mixing. The particles of the transfection agent are usually nanoparticles, which is generally understood to mean particles with dimensions in the range of 1 to 500 nm. Typically, the dimensions of the nanoparticles are in the range of 30 to 250 nm, more preferably 40 to 150 nm.

Preferably, the transfection agent contains at least one lipidoid of general formula I in an amount of 10 to 50 mol. 00 and at least one helper lipid in an amount of 50 to 90 mol. %. Preferably, the transfection agent contains at least one lipidoid of general formula I in an amount of 15 to 30 mol. %, and at least one helper lipid in an amount of 70 to 85 mol. %. In some preferred embodiments, the transfection agent comprises at least one lipidoid of general formula I in an amount of 15 to 30 mol. %, cholesterol in an amount of 30 to 55 mol. %, and at least one other helper lipid in an amount of 20 to 50 mol. %.

In a particularly preferred embodiment, the transfection agent contains at least one lipidoid of general formula I in an amount of 15 to 30 mol. %, cholesterol in an amount of 30 to 55 mol. %, 1,2-dioleoyl-sn-glycero-3-phosphoethanolamine in an amount of 20 to 45 mol. % and 1,2-dimyristoyl-rac-glycero-3-methoxypolyethyleneglycol-2000 in an amount of 0.5 to 5 mol. %.

The present invention also relates to a transfection particle comprising at least one lipidoid of formula I, at least one nucleic acid and/or a part thereof and/or nucleic acid derivative, and preferably also at least one helper lipid. The transfection particles can be prepared, for example, by mixing a solution of a lipidoid of general formula I, optionally containing helper lipids, with a solution of the nucleic acid and/or a part thereof and/or nucleic acid derivative. Mixing can be performed by means of techniques used in conventional nanoparticle technology, for example, by microfluidic mixing.

The weight ratio of the total amount of nucleic acid and/or a part thereof and/or nucleic acid derivative to the total amount of lipidoid of general formula I and helper lipids in the transfection particle is preferably in the range of 1:2 to 1:500, more preferably 1:5 to 1:100. Specifically and for illustration: in the particles which are prepared in the examples herein below, this ratio was around 1:9 for mRNA and around 1:68 for siRNA.

Transfection particles are usually nanoparticles, which is generally understood to mean particles with dimensions in the range of 1 to 500 nm. Typically, the dimensions of the transfection nanoparticles are in the range of 30 to 250 nm, preferably 40 to 200 nm, more preferably 40 to 150 nm.

The structure of the transfection particles was observed by cryogenic transmission electron microscopy, and the observation showed that the transfection particles were compact layered lipid nanoparticles containing nucleic acid (or a part or derivative thereof) inside.

Helper lipids in transfection reagents and transfection particles are mainly neutral lipids, sterols or lipid conjugates with hydrophilic polymers.

Neutral lipids have a zero net charge at physiological pH and they can exist in an uncharged form or electroneutral zwitterionic form at physiological pH, such as 1,2-dioleoyl-sn-glycero-3-phosphoethanolamine (DOPE), 1,2-dioleoyl-sn-glycero-3-phosphocholine (DOPC), 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), and 1,2-dioleoyl-sn-glycero-3-phosphoethanolamine-N-(Cyanine 5).

Sterols may, for example, be selected from cholesterol, 0-sitosterol, stigmastanol, campesterol, fucosterol, avenasterol, fecosterol, brassicasterol, ergosterol, and 9,11-dehydroergosterol. Preferably, sterol is cholesterol.

Lipid conjugates with hydrophilic polymers comprise a lipid portion and a polymer portion such as poly(ethyleneglycol), poly(2-ethyl-2-oxazoline), poly(2-methyl-2-oxazoline), poly(glycerol), poly(N-(2-hydroxypropyl) methacrylamide), poly(sarcosine) or glycol chitosan. Preferably, the polymer portion consists of poly(ethylene glycol) of molecular weight which may range from about 500 to about 10,000 Da, more preferably from about 1,000 to about 5,000 Da. Lipid conjugates with hydrophilic polymers may, for example, be selected from 1,2-dimyristoyl-rac-glycero-3-methoxy poly(ethyleneglycol)-2000, 1,2-dimyristoyl-sn-glycero-3-phosphoethanolamine-poly(ethylene glycol)-2000, 1,2-distearoyl-sn-glycero-3-phosphoethanolamine-poly(ethylene glycol)-2000, 1,2-dipalmitoyl-sn-glycero-3-phosphoethanolamine-poly(ethylene glycol)-2000, and the like. Lipid conjugate with hydrophilic polymers may be preferably 1,2-dimyristoyl-rac-glycero-3-methoxy poly(ethyleneglycol)-2000.

The nucleic acid or a part thereof are moieties containing one or more nucleotides and/or deoxynucleotides. The nucleic acid or the part thereof may be a therapeutic, diagnostic or prophylactic agent or may provide labeling for the cells or tissues into which they are transfected. The compounds of formula I thus have predominantly therapeutic or biotechnological uses.

The term "nucleic acid or a part thereof" is understood to mean nucleic acids or their segments selected preferably from oligonucleotides (1-100 nucleotides, e.g. aptamers), cyclic dinucleotides (e.g. 2',3'-cGAMP), antisense oligonucleotides, deoxyribonucleic acid (single-stranded DNA, double-stranded DNA, cDNA, plasmid DNA encoding a gene or genes), ribonucleic acid, typically messenger RNA (mRNA), transfer RNA (tRNA), small interfering RNA (siRNA), double-stranded RNA, micro-RNA (miRNA), piwi-RNA (piRNA), antisense RNA (asRNA), guide RNA (gRNA) for the CRISPR system and their combinations (typically e.g. gRNA and mRNA encoding Cas9 nuclease, Cas13a/C2c2 and Cas13b, or analogous nucleases, suitable for use in CRISPR, CRISPRi and other variations and subsequent modification of the host cell or tissue genome or modification of the host cell or tissue transcriptome). Furthermore, all nucleic acids (NA) disclosed herein may be formed or modified with synthetic base analogs, for example, to increase their stability in biological systems. Synthetic NA analogs involve, in particular, the following substitutions: phosphorylation at the 5' and/or 3' end of the strand, 5-methylcytidine-5'-triphosphate, $N^1$-methylpseudouridine-5'-triphosphate, $P^1$-(5'-(3'-O-methyl)-7-methyl-guanosyl)-$P^3$-(5'-(guanosyl))triphosphate, $P^1$-(guanosyl) $P^3$-(5'-(guanosyl))triphosphate, $P^1$-(5'-7-methyl-guanosyl) $P^3$-(5'-(guanosyl))triphosphate, $P^1$-(5'-2,2,7-trimethyl-guanosyl) $P^3$-(5'-(guanosyl))triphosphate, $N^6$-methyladenosine-5'-triphosphate, 2-thiouridine-5'-triphosphate, pseudouridine-5'-triphosphate, 5-methoxyuridine-5'-triphosphate, $N^1$-methyladenosine-5'-triphosphate, $N^4$-acetylcytidine-5'-triphosphate, 2-O-methyl, 2'-O-methoxyethyl, 2'-fluoro, a methylene bridge between the 2'-oxygen and the 4'-carbon of the pentose ring (a so-called locked nucleic acid), boranophosphonates, or phosphorothioates.

The present invention further includes the use of lipidoids of formula I or transfection agents or transfection particles for transfecting cells or tissues with nucleic acid and/or a part thereof and/or nucleic acid derivative in vitro. In addition, the invention includes lipidoids of formula I or transfection particles for use in transfecting cells or tissues with nucleic acid and/or a part thereof and/or nucleic acid derivative in vivo (excluding the transfection of human embryos for industrial or commercial use, and excluding the modification of human germ line).

Transfection particles containing lipidoids of general formula I are useful in a number of biological applications in basic research, especially for transfection of cell cultures or animals to deliver active nucleic acid and subsequent silencing or activation of a chromosomal gene or genes, genome editing (gene excision, gene insertion or mutation introduction) or transcriptome editing, or enabling the expression of a given protein encoded by the nucleic acid inserted by means of a transfection particle, so-called "in trans".

In veterinary and human medicine, transfection particles containing lipidoids of the general formula I can preferably be used for therapeutic or prophylactic purposes. Particles containing therapeutic nucleic acid can be administered to an animal or human to silence or activate chromosomal gene(s), to silence or activate immunogens, to inhibit or activate signaling pathways, to edit the genome (gene excision, gene insertion or mutation introduction) or the transcriptome, or enable the expression of protein(s) encoded by the nucleic acid.

The present invention also provides lipidoids of general formula I or transfection agents or transfection particles for use as medicaments, in particular for gene therapy. In particular, they are suitable for use in the treatment of malignancies and/or genetic disorders.

The lipidoids of general formula I or transfection particles can be formulated for therapeutic, cosmetic or biotechnological use in the form of preparations with pharmaceutically acceptable excipients. The formulations may be in liquid or solid form, or in other forms, such as an aerosol. Liquid forms include solutions, suspensions, dispersions, adapted e.g. for injection or oral administration. Solid forms include, for example, capsules, tablets, coated tablets, powders, suppositories, and other forms.

The liquid formulations can be nebulized. Nebulized suspensions may be breathed in directly from the nebulizing device or the nebulizing device can be attached to face masks tent, or intermittent positive pressure breathing machine.

The solid dosage forms may also be administered via inhalation using dry-powder inhalers. Suspension or dry powder formulations can be administered orally or nasally from devices which deliver the pharmaceutical composition in an appropriate manner.

In order to deliver an active substance on the skin or mucous membranes, the transfection particles with the active substance can be also prepared in the form of a cream, gel, ointment, paste, balm, liquid.

These topical forms may be applied directly on the site of action.

Pharmaceutically acceptable excipients include solvents, solubility control agents, pH adjusting agents, carriers, fillers, binders, glidants, disintegrants, preservatives, sorbents, viscosity control agents, agents that affect sensory properties such as taste, odor or the color of the formulation.

Furthermore, lipidoids of general formula I or the transfection agents or transfection particles can preferably be used for the purposes of the cosmetics industry in order to deliver an active substance to the site of action. The transfection particles with the active substance can be prepared in the form of a cream, gel, ointment, paste, balm, liquid and the like, and used as make-up, hair cosmetics or a personal hygiene product.

EXAMPLES

Figure 1:
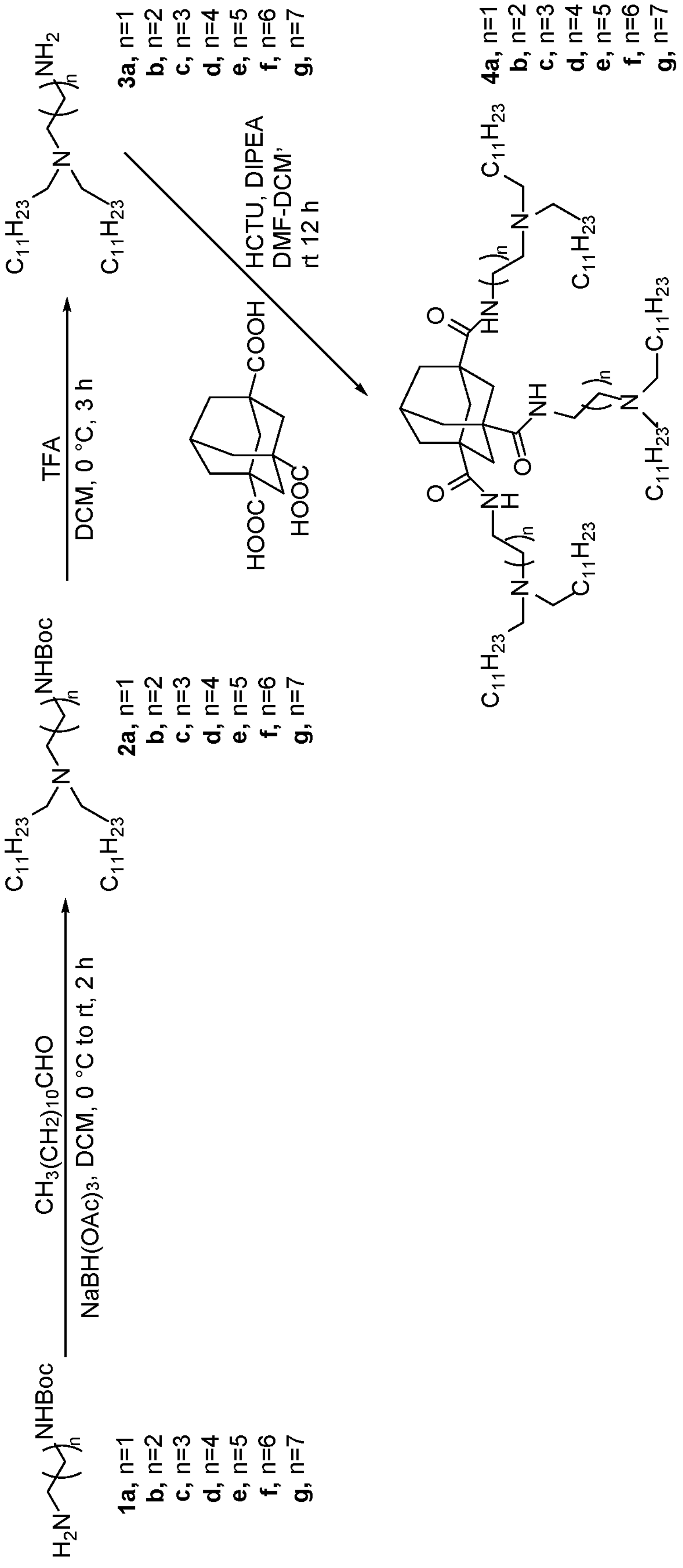
FIG. 1. Synthetic scheme of lipidoids 4a-g.
Figure 2:
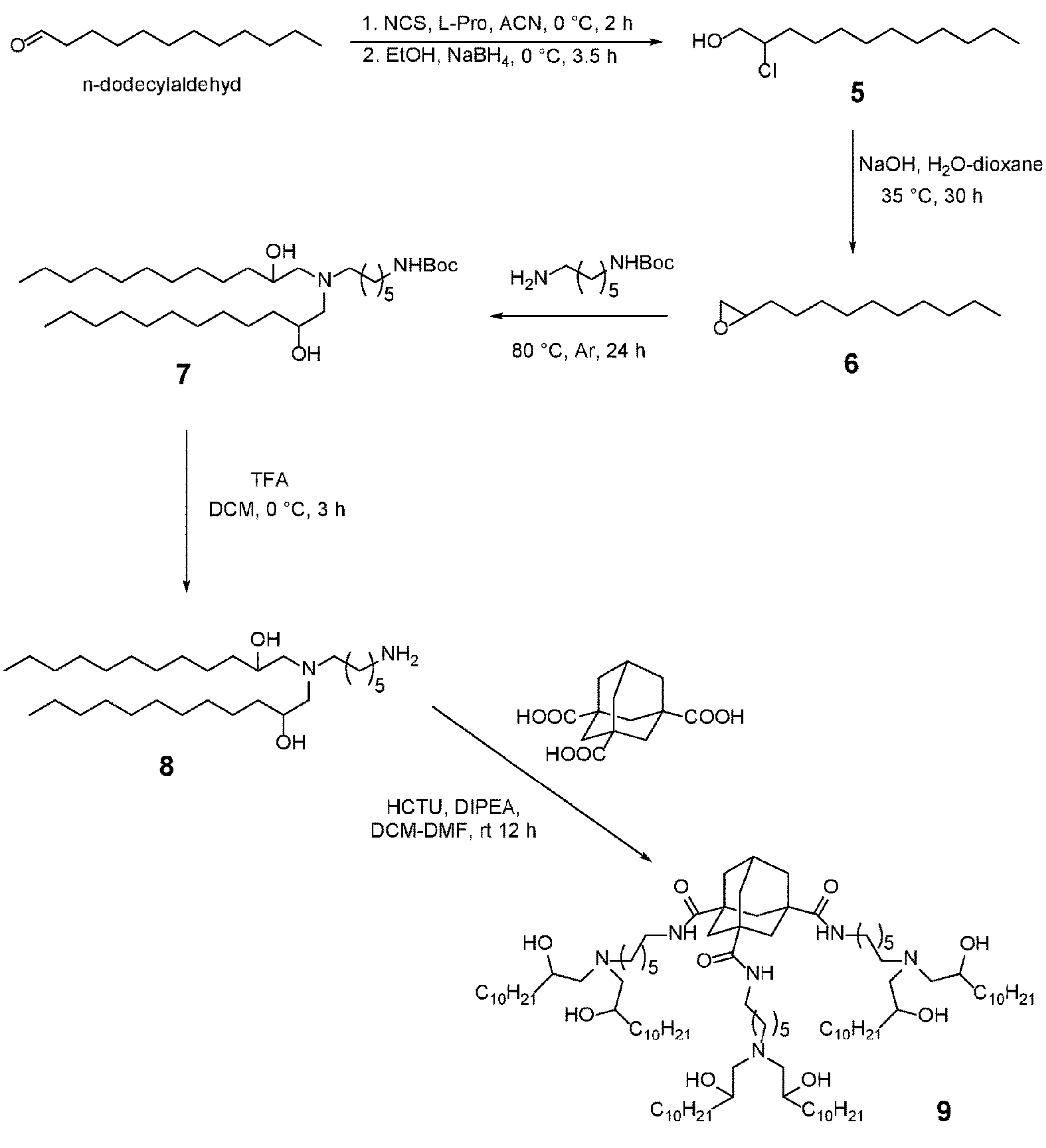
FIG. 2. Synthetic scheme of lipidoid 9.
Figure 3:
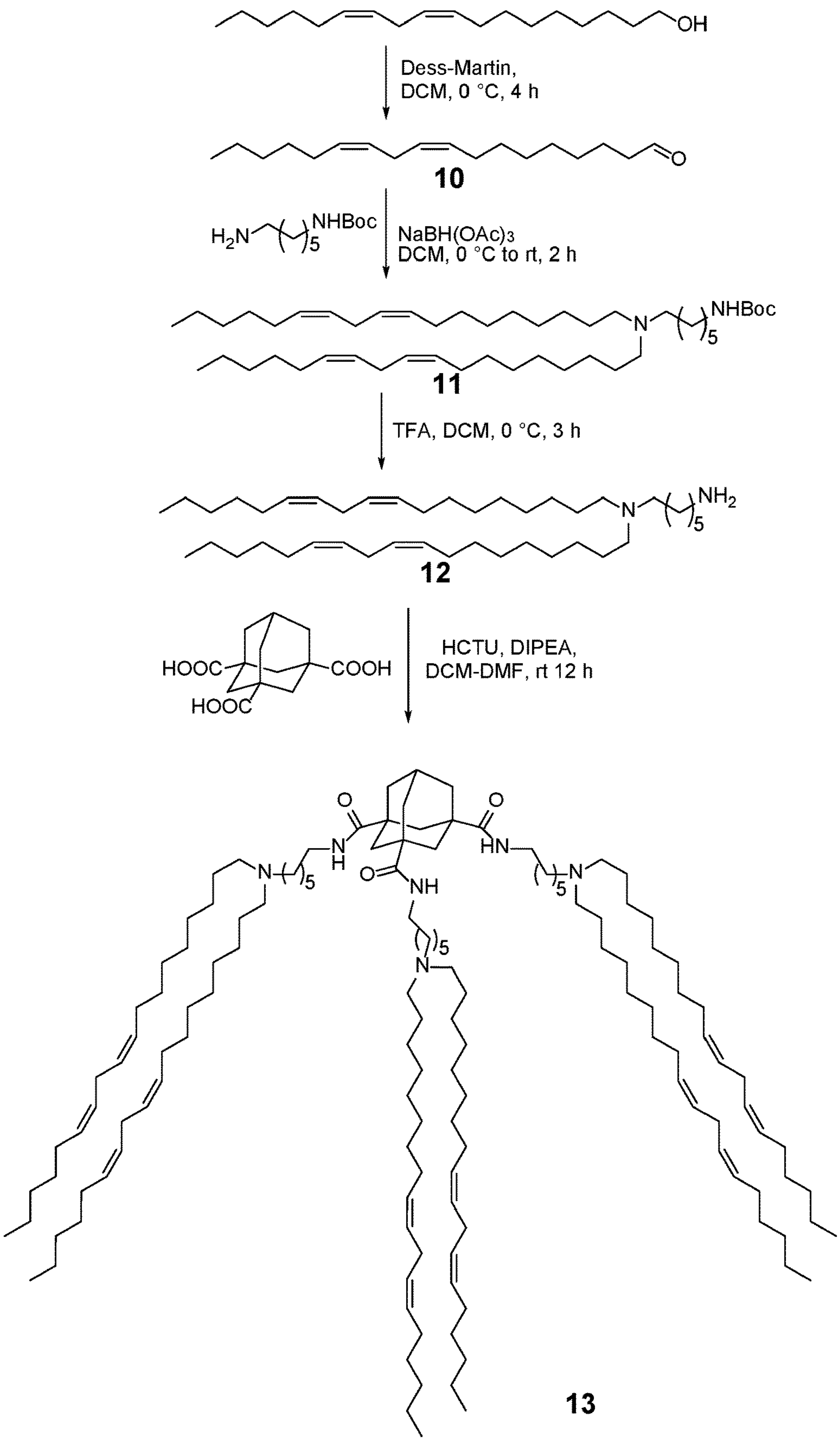
FIG. 3. Synthetic scheme of lipidoid 13.
Figure 4:
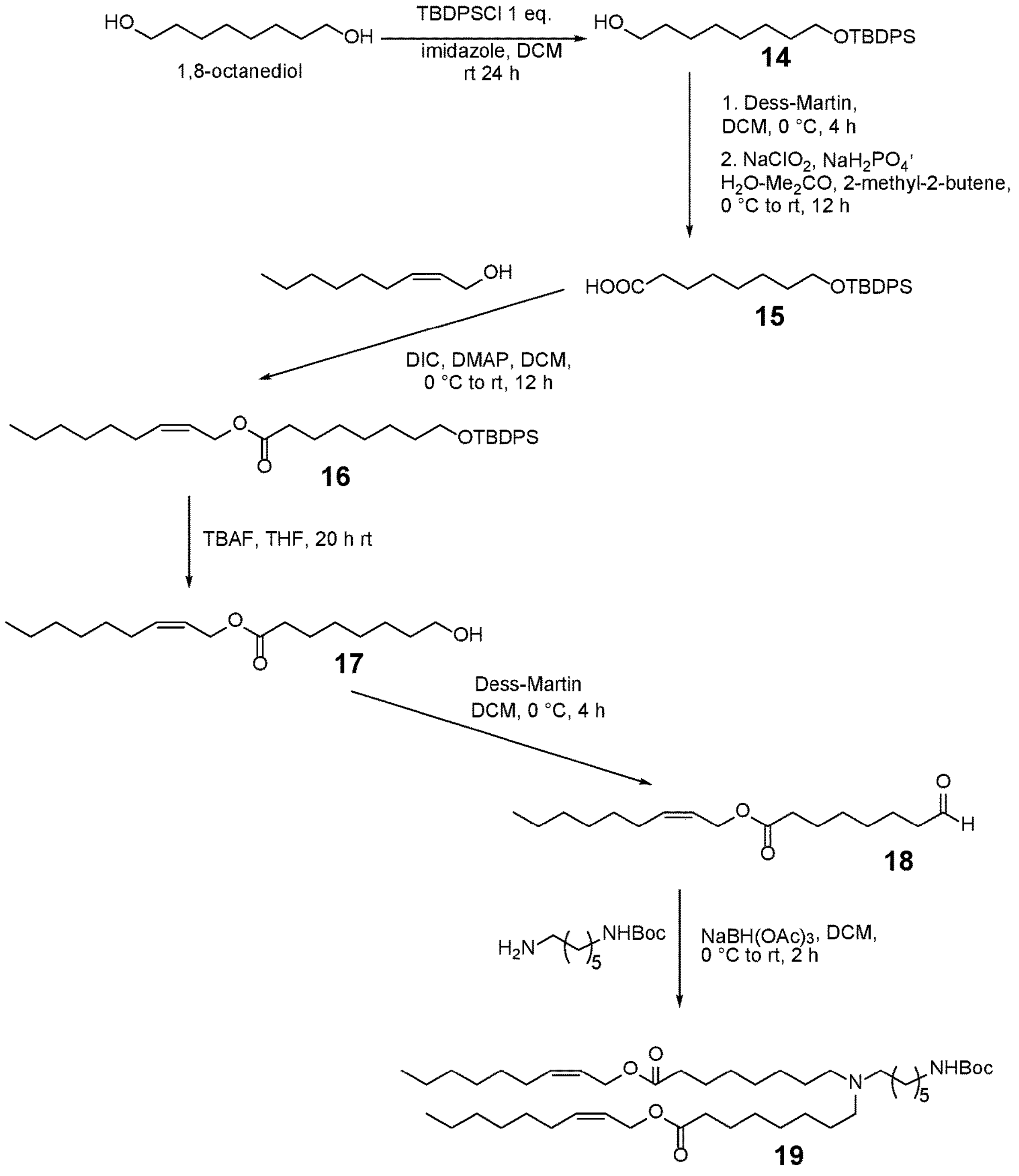
FIG. 4. Synthetic scheme of compound 19, precursor of lipidoid 21.
Figure 5:
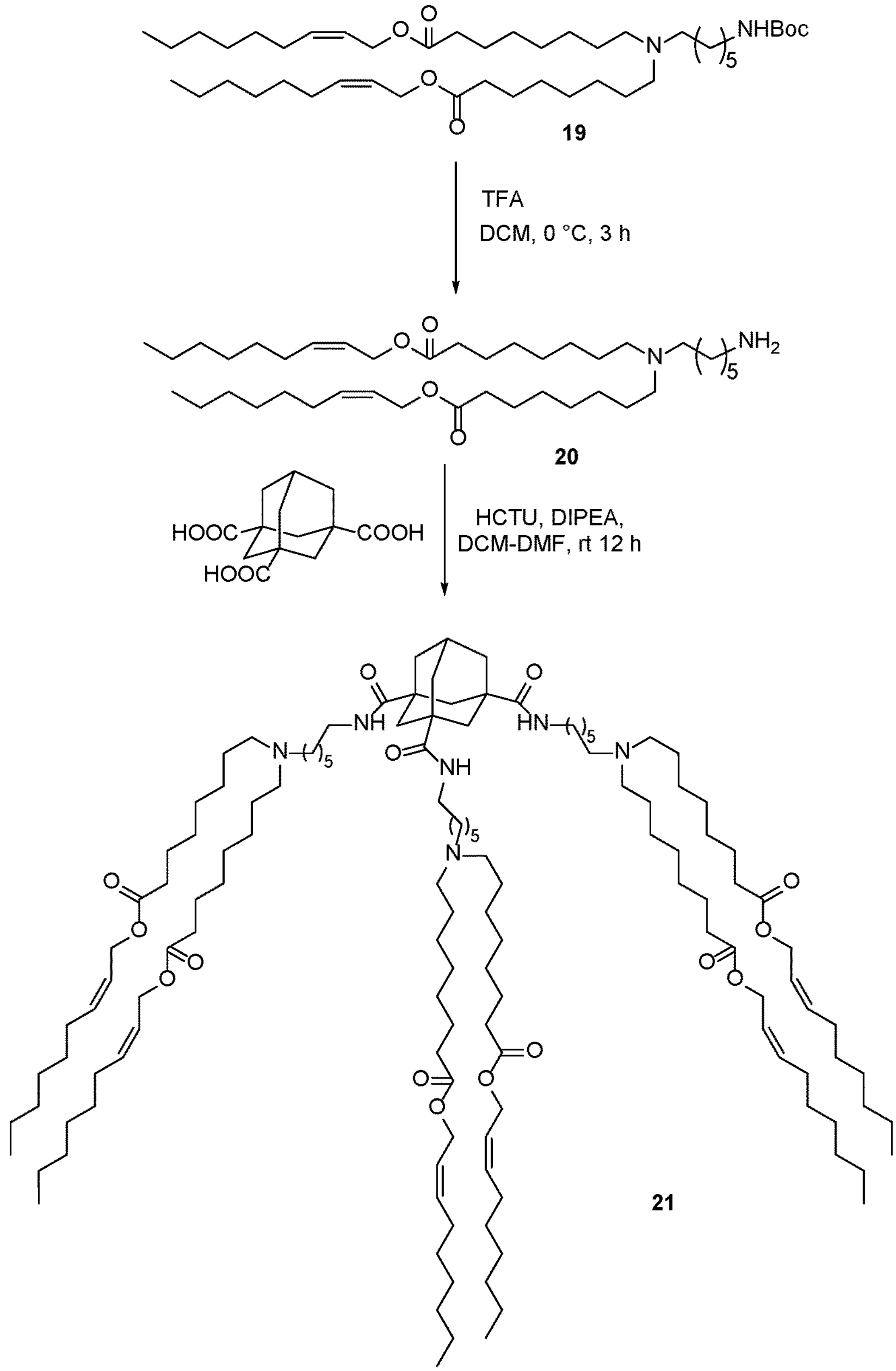
FIG. 5. Synthetic scheme of lipidoid 21.
Figure 6:
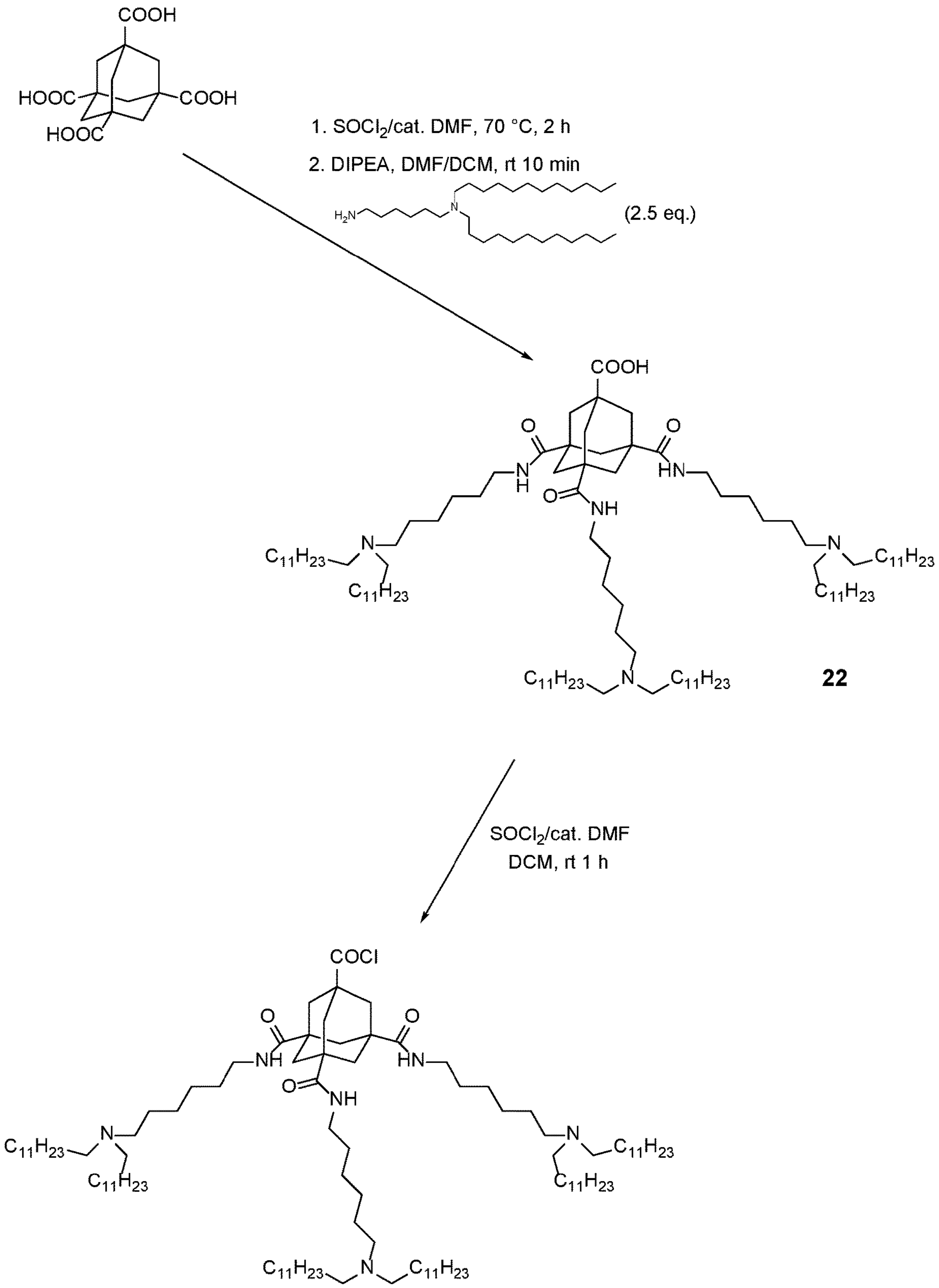
FIG. 6. Synthetic scheme of compound 22 and its acylchloride, precursors of lipidoids 23-25.

List of Abbreviations eq. equivalent
$R_f$ retention factor
TLC thin-layer chromatography
RVE rotary vacuum evaporator
rt room temperature
br s broad signal s singlet
d doublet
m multiplet
dd doublet of doublets
J interaction constant
6 chemical shift
HRMS high-resolution mass spectrometry
ESI electrospray ionization
MALDI matrix-assisted laser desorption/ionisation
IR infrared spectroscopy
NMR nuclear magnetic resonance
CE5 cyclohexane-ethylacetate mixture 95:5 (v/v)
CE20 cyclohexane-ethylacetate mixture 80:20 (v/v)
CE50 cyclohexane-ethylacetate mixture 50:50 (v/v)
D1 dichloromethane-methanol-25% aqueous $NH_3$ mixture 75:3 (v/v/v)
D2 dichloromethane-methanol-25% aqueous $NH_3$ mixture 175:22:3 (v/v/v)
D3 dichloromethane-methanol-25% aqueous $NH_3$ mixture 275:22:3 (v/v/v)
D4 dichloromethane-methanol-25% aqueous $NH_3$ mixture 375:22:3 (v/v/v)
TFA trifluoroacetic acid
HCTU O-(1H-6-chlorobenzotriazole-1-yl)-1,1,3,3-tetramethyluronium hexafluorophosphate
DIPEA N,N-diisopropylethylamine
DMF N,N-dimethylformamide
DCM dichloromethane
ACN acetonitrile
TBDPSCI tert-butyldiphenylchlorosilane
DIC diisopropylcarbodiimide
DMAP 4-dimethylaminopyridine
LNP lipid nanoparticles
NA nucleic acid
DNA deoxyribonucleic acid
RNA ribonucleic acid
mRNA messenger RNA
siRNA small interfering RNA
tRNA transfer RNA
miRNA micro RNA
ssDNA/RNA single-stranded DNA/RNA
dsDNA/RNA double-stranded DNA/RNA
DMG-$PEG_{2000}$ 1,2-dimyristoyl-rac-glycero-3-methoxypolyethyleneglycol-2000
DOPE 1,2-dioleoyl-sn-glycero-3-phosphoethanolamine
DOPC 1,2-dioleoyl-sn-glycero-3-phosphocholine
DSPC 1,2-distearoyl-sn-glycero-3-phosphocholine
DOPE-Cy5 1,2-dioleoyl-sn-glycero-3-phosphoethanolamine-N-(Cyanine 5)
Lip2000 Lipofectamine® 2000 (Invitrogen)

Example 1

$N^1$,$N^1$-Didodecylethan-1,2-diamine 3a

A 500 ml round-bottom flask equipped with a chlorocalcium cap and magnetic stirrer was filled with a solution of amine 1a (5.00 g, 31.2 mmol) in DCM (100 ml) and cooled to 0° C. in an ice bath. With intensive stirring, n-dodecylaldehyde (20.8 ml, 93.6 mmol, 3 eq.) was added, followed by sodium triacetoxyborohydride (19.8 g, 93.6 mmol, 3 eq.) in three portions over 10 minutes. The cooling bath was removed, and the reaction mixture was stirred at room temperature for 2 h. The progress of the reaction was monitored by TLC using an 80:20 (v/v) hexane-ethylacetate mobile phase on a TLC plate pre-saturated with ammonia (detection with ninhydrin). After completion of the reaction, aqueous NaOH solution (1 M, 200 ml) was added, the reaction mixture was stirred for 15 min, then poured into a separatory funnel and diluted with water (300 ml). The product was extracted with DCM (300 ml, 2×50 ml), the combined organic phase was washed with brine (50 ml), dried over anhydrous sodium sulphate, filtered through an S2 frit, and the solvents were evaporated in an RVE. The dark oily residue was purified by silica gel column chromatography using a linear gradient of ethyl acetate in hexane (10-30%). Amine 2a (5.12 g, 33.0%) was obtained as a yellowish oil.

Trifluoroacetic acid (10 ml) was added to a solution of compound 2a (5.12 g) in DCM (10 ml), cooled to 0° C. with stirring in an ice bath, and the reaction mixture was left at 0° C. for 3 h. The solution was then poured into a 11 separatory flask, diluted with 20% aqueous $Na_2CO_3$ (300 ml), and the product was extracted with DCM (250 ml, 2×50 ml). The combined organic phase was washed with brine (100 ml), dried over anhydrous sodium sulphate, filtered through an S2 frit, and the solvents were evaporated in an RVE. The crude product was purified by silica gel column chromatography using a linear gradient of D1 in DCM (0-70%). The diamine 3a (2.55 g, 62.4%; $R_f$ 0.46 in mobile phase D2 on a TLC plate pre-saturated with ammonia, detection with ninhydrin) was obtained in the form of a yellowish oil. $^1H$ NMR (600 MHz, $CDCl_3$): δ=2.895, 2.64, 2.48, 1.45, 1.28, 1.26, 1.24-1.28, 1.24, 0.87 ppm. $^{13}C$ NMR (150.9 MHz, $CDCl_3$): δ=54.31, 53.85, 38.33, 31.90, 29.65, 29.62, 29.61, 29.52, 29.34, 26.36, 23.88, 22.67, 14.10 ppm. IR (film): $\nu_{max}/cm^{-1}$=3371 w and 3315 w (ν $NH_2$), 2801 m ($\nu_s$ N—$\underline{CH_2}$), 2953 s ($\nu_{as}CH_3$), 2924 vs ($\nu_{as}$ $CH_2$), 2853 s ($\nu_s$ $CH_2$), 1467 m and 1457 m, sh ($\beta_s$ $CH_2$ and $\delta_{as}$ $CH_3$), 1378 w and 1367 w ($\delta_s$ $CH_3$), 721 m ($\beta_{as}$ $CH_2$). HRMS (ESI): m/z calculated for $C_{26}H_{57}N_2$ $[M+H]^+$ 397.45163; found 397.45093.

$N^1$,$N^3$,$N^5$-Tris(2-(didodecylamino)ethyl) adamantane-1,3,5-tricarboxamide 4a O-(1H-6-chlorobenzotriazole-1-yl)-1,1,3,3-tetramethyluronium hexafluorophosphate (HCTU, 256 mg, 0.596 mmol, 4 eq.) and N,N-diisopropylethylamine (DIPEA, 0.415 ml, 2.39 mmol, 16 eq.) were added to a solution of adamantane-1,3,5-tricarboxylic acid (40 mg, 0.149 mmol) in anhydrous DMF (1.5 ml), and the solution was stirred for 15 min at room temperature. Then a solution of $N^1$,$N^1$-didodecylethane-1,2-diamine 3a (237 mg, 0.149 mmol, 4 eq.) in DCM (1.0 ml) was added, and the reaction mixture was stirred for 12 h. The solution was poured into a 250 ml separatory flask, diluted with saturated aqueous $NaHCO_3$ (50 ml), and the product was extracted with DCM (50 ml, 2×20 ml). The combined organic phase was washed with brine (20 ml), dried over anhydrous sodium sulphate, filtered through an S2 frit, and the solvents were evaporated in an RVE. The crude product was purified by silica gel column chromatography using a linear gradient of D1 in DCM (20-50%). Lipidoid 4a (71 mg, 33.9%; $R_f$ 0.73 in D2 in mobile phase D2 on a TLC plate pre-saturated with ammonia, detection with ninhydrin) was obtained in the form of a viscous yellowish oil. $^1H$ NMR (600 MHz, $CDCl_3$): δ=7.33, 3.56, 3.32, 3.125, 3.075, 2.34, 2.01, 1.91, 1.79, 1.67, 1.36, 1.285, 1.26-1.32, 1.25, 0.88 ppm. $^{13}C$ NMR (150.9 MHz, $CDCl_3$): δ=180.48, 56.72, 53.78, 41.38, 39.04, 36.86, 36.29, 31.90, 29.64, 29.62, 29.50, 29.40, 29.35, 29.04, 27.79, 26.36, 23.88, 22.68, 14.10 ppm. IR ($CCl_4$): $\nu_{max}/cm^{-1}$=3440 w and 3322 w (ν NH), 1653 w (amide I) and 1623 w (amide I bound), 1535 w (amide II), 2956 m ($\nu_{as}$ $CH_3$), 2927 vs ($\nu_{as}$ $CH_2$), 2855 m ($\nu_s$ $CH_2$), 1467 w and 1457 w ($\beta_s$ $CH_2$ and $\delta_{as}$ $CH_3$), 1378 w ($\delta_s$ $CH_3$). HRMS (MALDI): m/z calculated for $C_{91}H_{179}N_6O_3$ $[M+H]^+$ 1404.4033; found 1404.4012.

Example 2

$N^1$,$N^1$-Didodecylpropane-1,3-diamine 3b

Amine 2b was prepared from amine 1b (6.0 g, 34.43 mmol), n-dodecylaldehyde (22.91 ml, 103.30 mmol, 3 eq.) and sodium triacetoxyborohydride (21.89 g, 103.30 mmol, 3 eq.) according to the procedure described for compound 2a in Example 1. Amine 2b was obtained as a yellowish oil (7.72 g, 43.9%).

The deprotection of amine 2b was performed according to the procedure described for compound 2a in Example 1; diamine 3b (4.26 g, 68.6%; $R_f$ 0.35 in mobile phase D2 on a TLC plate pre-saturated with ammonia, detection with ninhydrin) was obtained in the form of a yellowish oil. $^1H$ NMR (600 MHz, $CDCl_3$): δ=3.07, 2.70, 2.50, 1.81, 1.46, 1.28, 1.26, 1.25-1.29, 1.24, 0.87 ppm. $^{13}C$ NMR (150.9 MHz, $CDCl_3$): δ=53.70, 53.30, 41.18, 31.90, 29.64, 29.62, 29.60, 29.58, 29.48, 29.33, 27.42, 25.71, 23.87, 22.67, 14.10 ppm. IR (film): $\nu_{max}$/$cm^{-1}$=3361 w and 3274 w (ν $NH_2$), 2803 m ($\nu_s$ N—$\underline{CH_2}$), 2954 s ($\nu_{as}$$CH_3$), 2924 vs ($\nu_{as}$ $CH_2$), 2853 s ($\nu_s$ $CH_2$), 1467 m and 1456 m, sh ($\beta_s$ $CH_2$ and $\delta_{as}$ $CH_3$), 1378 w and 1364 w ($\delta_s$ $CH_3$), 720 m ($\beta_{as}$ $CH_2$). HRMS (ESI): m/z calculated for $C_{27}H_{59}N_2$ $[M+H]^+$ 411.46728; found 411.46652.

$N^1$,$N^3$,$N^5$-tris(3-(didodecylamino)propyl)adamantane-1,3,5-tricarboxamide 4b Lipidoid 4b was prepared from adamantane-1,3,5-tricarboxylic acid (20 mg, 0.075 mmol), HCTU (128 mg, 0.298 mmol, 4 eq.), DIPEA (0.208 ml, 1.19 mmol, 16 eq.) and diamine 3b (123 mg, 0.298 mmol, 4 eq.) according to the procedure described for compound 4a in Example 1; lipidoid 4b (64 mg, 59.3%; $R_f$ 0.51 in mobile phase D2 on a TLC plate pre-saturated with ammonia, detection with ninhydrin) was obtained as a viscous yellow oil. $^1H$ NMR (600 MHz, $CDCl_3$): δ=7.59, 3.36, 2.99, 2.88, 2.31, 2.13, 2.00, 1.96, 1.81, 1.67, 1.31, 1.28, 1.25-1.30, 1.24, 0.87 ppm. $^{13}C$ NMR (150.9 MHz, $CDCl_3$): δ=177.39, 55.22, 50.70, 41.78, 40.38, 37.20, 35.67, 31.89, 29.60, 29.51, 29.48, 29.32, 29.19, 28.39, 26.94, 24.10, 23.68, 22.67, 14.10 ppm. IR ($CCl_4$): $\nu_{max}$/$cm^{-1}$=3466 w and 3287 w (ν NH), 1656 m (amide I) and 1511 m (amide II), 2814 w ($\nu_s$ $\underline{CH_2}NR_2$), 2954 s ($\nu_{as}$ $CH_3$), 2927 vs ($\nu_{as}$ $CH_2$), 2871 m ($\nu_s$ $\underline{CH_3}$), 2855 s ($\nu_s$$CH_2$), 1468 m and 1456 m ($\beta_s$ $CH_2$ and $\delta_{as}$ $CH_3$), 1378 w ($\delta_s$ $CH_3$), 721 w ($\beta_{as}$ $CH_2$). HRMS (MALDI): m/z calculated for $C_{94}H_{185}O_3N_6$ $[M+H]^+$ 1446.45027; found 1446.44896.

Example 3

$N^1$,$N^1$-Didodecylbutane-1,4-diamine 3c

Amine 2c was prepared from amine 1c (5.0 g, 26.56 mmol), n-dodecylaldehyde (17.67 ml, 79.67 mmol, 3 eq.) and sodium triacetoxyborohydride (16.89 g, 79.67 mmol, 3 eq.) according to the procedure described for compound 2a in Example 1. Amine 2c was obtained as a yellowish oil (4.15 g, 29.8%). The deprotection of amine 2c was performed according to the procedure described for compound 2a in Example 1; diamine 3c (2.36 g, 70.3%; $R_f$ 0.29 in mobile phase D2 on a TLC plate pre-saturated with ammonia, detection with ninhydrin) was obtained in the form of a yellowish oil. $^1H$ NMR (600 MHz, $CDCl_3$): δ=2.85, 2.81, 2.59, 1.725, 1.68, 1.51, 1.28, 1.265, 1.25-1.30, 1.24, 0.87 ppm. $^{13}C$ NMR (150.9 MHz, $CDCl_3$): δ=53.33, 52.74, 40.44, 31.90, 29.64, 29.60, 29.60, 29.40, 29.33, 28.65, 27.46, 24.83, 24.40, 22.67, 14.10 ppm. IR (film): $\nu_{max}$/$cm^{-1}$=3370 w and 3274 w (ν $NH_2$), 2798 m ($\nu_s$ N—$\underline{CH_2}$), 2957 s ($\nu_{as}$ $CH_3$), 2924 vs ($\nu_{as}$ $CH_2$), 2853 s ($\nu_s$ $CH_2$), 1467 m and 1456 m, sh ($\beta_s$ $CH_2$ and $\delta_{as}$ $CH_3$), 1378 w and 1367 w ($\delta_s$ $CH_3$), 720 m ($\beta_{as}$ $CH_2$). HRMS (ESI): m/z calculated for $C_{28}H_{61}N_2$ $[M+H]^+$ 425.48293; found 425.48227.

$N^1$,$N^3$,$N^5$-tris(4-(didodecylamino)butyl)adamantane-1,3,5-tricarboxamide 4c Lipidoid 4c was prepared from adamantane-1,3,5-tricarboxylic acid (40 mg, 0.149 mmol), HCTU (256 mg, 0.596 mmol, 4 eq.), DIPEA (0.416 ml, 2.39 mmol, 16 eq.) and diamine 3c (253 mg, 0.596 mmol, 4 eq.) according to the procedure described for compound 4a in Example 1; lipidoid 4c (64 mg, 28.8%; $R_f$ 0.48 in mobile phase D2 on a TLC plate pre-saturated with ammonia, detection with ninhydrin) was obtained in the form of a viscous yellowish oil. $^1H$ NMR (600 MHz, $CDCl_3$): δ=7.27, 3.335, 3.03, 2.98, 2.28, 2.12, 2.06, 1.875, 1.81, 1.74, 1.64, 1.33, 1.28, 1.25-1.29, 1.24, 0.87 ppm. $^{13}C$ NMR (150.9 MHz, $CDCl_3$): δ=177.27, 52.78, 52.27, 41.83, 40.26, 37.36, 37.20, 31.88, 29.58, 29.49, 29.43, 29.31, 29.10, 28.37, 26.82, 26.56, 22.94, 22.66, 20.79, 14.10 ppm. IR ($CCl_4$): $\nu_{max}$/$cm^{-1}$=3441 w and 3329 w (ν NH), 1641 m (amide I), 1534 w (amide II), 2956 m ($\nu_{as}$ $CH_3$), 2927 vs ($\nu_{as}$ $CH_2$), 2855 m ($\nu_s$ $CH_2$), 1466 m and 1458 m ($\beta_s$ $CH_2$ and $\delta_{as}$ $CH_3$), 1378 w ($\delta_s$ $CH_3$). HRMS (MALDI): m/z calculated for $C_{97}H_{191}N_6O_3$ $[M+H]^+$ 1488.4972; found 1488.4956.

Example 4

$N^1$,$N^1$-Didodecylpentane-1,5-diamine 3d

Amine 2d was prepared from amine 1d (5.0 g, 24.72 mmol), n-dodecylaldehyde (16.45 ml, 74.15 mmol, 3 eq.) and sodium triacetoxyborohydride (15.71 g, 74.15 mmol, 3 eq.) According to the procedure described for compound 2a in Example 1. Amine 2d was obtained as a yellowish oil (6.01 g, 45.1%).

The deprotection of amine 2d was performed according to the procedure described for compound 2a in Example 1; diamine 3d (4.32 g, 88.3%; $R_f$ 0.28 in mobile phase D2 on a TLC plate pre-saturated with ammonia, detection with ninhydrin) was obtained as a yellowish oil. $^1H$ NMR (600 MHz, $CDCl_3$): δ=2.75, 2.68, 2.55, 1.565, 1.53, 1.50, 1.35, 1.28, 1.27, 1.24-1.28, 1.24, 0.87 ppm. $^{13}C$ NMR (150.9 MHz, $CDCl_3$): δ=53.61, 53.55, 41.48, 32.10, 31.89, 29.63, 29.61, 29.58, 29.45, 29.32, 27.41, 25.74, 24.90, 24.55, 22.66, 14.09 ppm. IR (film): $\nu_{max}$/$cm^{-1}$=3367 w and 3284 w (ν $NH_2$), 2797 m (vs N—$\underline{CH_2}$), 2956 s (vas $CH_3$), 2924 vs ($\nu_{as}$ $CH_2$), 2853 s ($\nu_s$ $CH_2$), 1467 m and 1456 m, sh ($\beta_s$ $CH_2$ and $\delta_{as}$ $CH_3$), 1378 w and 1367 w ($\delta_s$ $CH_3$), 720 m ($\beta_{as}$ $CH_2$). HRMS (ESI): m/z calculated for $C_{29}H_{63}N_2$ $[M+H]^+$ 439.49858; found 439.49783.

$N^1$,$N^3$,$N^5$-Tris(5-(didodecylamino)pentyl)adamantane-1,3,5-tricarboxamide 4d Lipidoid 4d was prepared from adamantane-1,3,5-tricarboxylic acid (40 mg, 0.149 mmol), HCTU (256 mg, 0.596 mmol, 4 eq.), DIPEA (0.416 ml, 2.39 mmol, 16 eq.) and diamine 3d (262 mg, 0.596 mmol, 4 eq.) according to the procedure described for compound 4a in Example 1; lipidoid 4d (74 mg, 32.4%; $R_f$ 0.49 in mobile phase D2 on a TLC plate pre-saturated with ammonia, detection with ninhydrin) was obtained as a viscous yellowish oil. $^1H$ NMR (600 MHz, $CDCl_3$): δ=6.91, 3.27, 2.99, 2.29, 2.09, 1.97, 1.82, 1.81, 1.76, 1.59, 1.45, 1.34, 1.28, 1.25-1.30, 1.24, 0.87 ppm. $^{13}C$ NMR (150.9 MHz, $CDCl_3$): δ=177.01, 52.77, 52.30, 41.82, 40.10, 38.33, 37.59, 31.88, 29.58, 29.48, 29.43, 29.30, 29.09, 28.53, 28.39, 26.84, 23.83, 23.09, 23.02, 22.66, 14.10 ppm. IR ($CCl_4$): $\nu_{max}/cm^{-1}$=3322 w (ν NH), 1640 m (amide I), 1535 w (amide II), 2956 m ($\nu_{as}$ $CH_3$), 2927 vs ($\nu_{as}$ $CH_2$), 2855 m ($\nu_s$ $CH_2$), 1467 m and 1457 m ($\beta_s$ $CH_2$ and $\delta_{as}$ $CH_3$), 1378 w ($\delta_s$ $CH_3$), 722 m ($\beta_{as}$ $CH_2$). HRMS (MALDI): m/z calculated for $C_{100}H_{197}N_6O_3$ $[M+H]^+$1530.5442; found 1530.5478.

Example 5

$N^1$,$N^1$-Didodecylhexane-1,6-diamine 3e

Amine 2e was prepared from amine 1e (5.0 g, 23.11 mmol), n-dodecylaldehyde (15.38 ml, 69.34 mmol, 3 eq.) and sodium triacetoxyborohydride (14.70 g, 69.34 mmol, 3 eq.) according to the procedure described for compound 2a in Example 1. Amine 2e was obtained as a yellowish oil (3.67 g, 28.7%).

The deprotection of amine 2e was performed according to the procedure described for compound 2a in Example 1; diamine 3e (2.17 g, 72.2%; $R_f$ 0.31 in mobile phase D2 on a TLC plate pre-saturated with ammonia, detection with ninhydrin) was obtained as a yellowish oil. $^1H$ NMR (600 MHz, $CDCl_3$): δ=2.73, 2.65, 2.57, 1.56, 1.52, 1.51, 1.36, 1.31, 1.28, 1.25-1.29, 1.24, 0.87 ppm. $^{13}C$ NMR (150.9 MHz, $CDCl_3$): δ=53.51, 53.20, 41.62, 32.40, 31.89, 29.63, 29.61, 29.57, 29.44, 29.32, 27.39, 27.09, 26.53, 25.65, 25.02, 22.66, 14.10 ppm. IR (film): $\nu_{max}/cm^{-1}$=3374 w and 3294 w (ν $NH_2$), 2797 m ($\nu_s$ N—$\underline{CH_2}$), 2956 s ($\nu_a$ $CH_3$), 2924 vs ($\nu_{as}$ $CH_2$), 2853 s ($\nu_s$ $CH_2$), 1467 m and 1455 m, sh ($\beta_s$ $CH_2$ and $\delta_{as}$ $CH_3$), 1378 w and 1367 w ($\delta_s$ $CH_3$), 721 m ($\beta_{as}$ $CH_2$). HRMS (ESI): m/z calculated for $C_{30}H_{65}N_2$ $[M+H]^+$ 453.51423; found 453.51340.

$N^1$,$N^3$,$N^5$-Tris(6-(didodecylamino)hexyl)adamantane-1,3,5-tricarboxamide 4e Lipidoid 4e was prepared from adamantane-1,3,5-tricarboxylic acid (40 mg, 0.149 mmol), HCTU (256 mg, 0.596 mmol, 4 eq.), DIPEA (0.416 ml, 2.39 mmol, 16 eq.) and diamine 3e (270 mg, 0.596 mmol, 4 eq.) according to the procedure described for compound 4a in Example 1; lipidoid 4e (91 mg, 38.8%; $R_f$ 0.52 in mobile phase D2 on a TLC plate pre-saturated with ammonia, detection with ninhydrin) was obtained as a viscous yellowish oil. $^1H$ NMR (600 MHz, $CDCl_3$): δ=7.80, 3.33, 3.03, 2.99, 2.37, 2.27, 2.02, 1.92, 1.81, 1.76, 1.62, 1.43, 1.41, 1.34, 1.285, 1.26-1.30, 1.24, 0.88 ppm. $^{13}C$ NMR (150.9 MHz, $CDCl_3$): δ=177.87, 52.87, 52.26, 41.74, 39.31, 36.86, 31.90, 29.60, 29.50, 29.44, 29.32, 29.10, 28.26, 26.82, 25.77, 25.52, 23.44, 23.14, 22.68, 14.12 ppm. IR ($CCl_4$): $\nu_{max}/cm^{-1}$=3463 w and 3327 w (ν NH), 1641 m (amide I), 1535 m (amide II), 2958 s ($\nu_{as}$ $CH_3$), 2871 s ($\nu_s$ $CH_3$), 1467 m and 1457 m ($\beta_s$ $CH_2$ and $\delta_{as}$ $CH_3$), 2927 s ($\nu_{as}$ $CH_2$), 2855 s ($\nu_s$ $CH_2$), 1378 w ($\delta_s$ $CH_3$), 721 w ($\beta_{as}$ $CH_2$), 2799 w ($\nu_s$ $\underline{CH_2}NR_2$). HRMS (MALDI): m/z calculated for $C_{103}H_{203}N_6O_3$ $[M+H]^+$ 1572.5911; found 1572.5881.

Example 6

$N^1$,$N^1$-Didodecylheptane-1,7-diamine 3f

Amine 2f was prepared from amine 1f (1.0 g, 4.34 mmol), n-dodecylaldehyde (3.14 ml, 13.02 mmol, 3 eq.) and sodium triacetoxyborohydride (2.76 g, 13.02 mmol, 3 eq.) according to the procedure described for compound 2a in Example 1. Amine 2f was obtained as a yellowish oil (1.74 g, 70.6%).

The deprotection of amine 2f was performed in a mixture of TFA (4 ml) and DCM (4 ml) according to the procedure described for 2a in Example 1; diamine 3f (0.842 g, 59.1%; $R_f$ 0.38 in mobile phase D2 on a TLC plate pre-saturated with ammonia, detection with ninhydrin) was obtained as a yellowish oil. $^1H$ NMR (600 MHz, $CDCl_3$): δ=2.73, 2.69, 2.64, 1.56, 1.50, 1.30, 1.28, 1.25-1.31, 1.25, 0.87 ppm. $^{13}C$ NMR (150.9 MHz, $CDCl_3$): δ=53.37, 53.20, 41.62, 32.22, 31.89, 27.10-29.60, 26.57, 25.14, 22.66, 14.10 ppm. IR ($CCl_4$): $\nu_{max}/cm^{-1}$=3391 vw ($\nu_{as}$ $NH_2$); 2960 s, sh ($\nu_a$ $CH_3$); 2927 vs ($\nu_{as}$ $CH_2$); 2872 s, sh ($\nu_s$ $CH_3$); 2855 vs ($\nu_s$ $CH_2$); 2798 m ($\nu_s$ N—$\underline{CH_2}$); 1467 s and 1458 m ($\beta_s$ $CH_2$ and $\delta_{as}$ $CH_3$); 1378 w ($\delta_s CH_3$); 1302 w ($\gamma_s$ $CH_2$); 721 w ($\beta_{as}$ and $\gamma_{as}$ $CH_2$). HRMS (ESI): m/z calculated for $C_{31}H_{67}N_2$ $[M+H]^+$ 467.52988; found 467.52974.

$N^1$,$N^3$,$N^5$-Tris(7-(didodecylamino)heptyl)adamantane-1,3,5-tricarboxamide 4f Lipidoid 4f was prepared from adamantane-1,3,5-tricarboxylic acid (40 mg, 0.149 mmol), HCTU (256 mg, 0.596 mmol, 4 eq.), DIPEA (0.416 ml, 2.39 mmol, 16 eq.) and diamine 3f (278 mg, 0.596 mmol, 4 eq.) according to the procedure described for compound 4a in Example 1; lipidoid 4f (199 mg, 82.6%; $R_f$ 0.55 in mobile phase D2 on a TLC plate pre-saturated with ammonia, detection with ninhydrin) was obtained as a viscous yellowish oil. $^1H$ NMR (600 MHz, $CDCl_3$): δ=7.97, 3.22, 3.09, 2.34, 1.92, 1.83, 1.82, 1.70, 1.58, 1.52, 1.36, 1.30, 1.285, 1.28, 1.25-1.32, 1.25, 0.88 ppm. $^{13}C$ NMR (150.9 MHz, $CDCl_3$): δ=177.27, 54.00, 53.14, 41.59, 39.48, 39.30, 36.92, 31.89, 29.60, 29.48, 29.39, 29.32, 29.06, 28.22, 26.50, 25.58, 23.63, 23.38, 22.67, 14.10 ppm. IR ($CCl_4$): $\nu_{max}/cm^{-1}$=3438 w (free) and 3339, 3196 w (bound) (ν NH); 1627 m (amide I); 1535 m (amide II); 2956 s, sh ($\nu_{as}$ $CH_3$); 2873 m, sh ($\nu_s$ $CH_3$); 1468 m and 1457 m, sh ($\beta_s$ CH, and $\delta_a$, $CH_3$); 2927 vs ($\nu_{as}$ $CH_2$); 2856 s ($\nu_s$ $CH_2$); 1378 w ($\delta_s$ $CH_3$); 722 w ($\beta_{as}$ $CH_2$); 2805 w (ν $\underline{CH_2}NR_2$). HRMS (MALDI): m/z calculated for $C_{106}H_{209}N_6O_3$ $[M+H]^+$ 1614.6381; found 1614.6414.

Example 7

$N^1$,$N^1$-Didodecyloctane-1,8-diamine 3g

Amine 2g was prepared from amine 1g (1.0 g, 4.09 mmol), n-dodecylaldehyde (2.96 ml, 12.28 mmol, 3 eq.) and sodium triacetoxyborohydride (2.60 g, 12.28 mmol, 3 eq.) according to the procedure described for compound 2a in Example 1. The amine 2g was obtained as a yellowish oil (1.98 g, 83.1%).

The deprotection of amine 2g was performed in a mixture of TFA (4 ml) and DCM (4 ml) according to the procedure described for 2a in Example 1; diamine 3g (0.848 g, 52.0%; $R_f$ 0.35 in mobile phase D2 on a TLC plate pre-saturated with ammonia, detection with ninhydrin) was obtained in the form of a yellowish oil. $^1H$ NMR (600 MHz, $CDCl_3$): δ=2.70, 2.63, 2.53, 1.51, 1.47, 1.32, 1.28, 1.25-1.32, 1.25, 0.87 ppm. $^{13}C$ NMR (150.9 MHz, $CDCl_3$): δ=53.61, 53.20, 41.92, 33.00, 31.90, 27.30-29.60, 26.70, 25.83, 22.67, 14.10 ppm. IR ($CCl_4$): $\nu_{max}$/$cm^{-1}$=3391 vw ($\nu_{as}$ $NH_2$); 2960 s, sh ($\nu_{as}$ $CH_3$); 2927 vs ($\nu_{as}CH_2$); 2872 s, sh ($\nu_s$ $CH_3$); 2855 vs ($\nu_s$ $CH_2$); 2799 m ($\nu_s$ N—$\underline{CH_2}$); 1467 s and 1458 m ($\beta_s$ $CH_2$ and $\delta_{as}CH_3$); 1378 w ($\delta_s$ $\underline{CH_3}$); 1302 w ($\gamma_s$ $CH_2$); 721 w ($\beta_{as}$ and $\gamma_{as}$ $CH_2$). HRMS (ESI): m/z calculated for $C_{32}H_{69}N_2$ $[M+H]^+$ 481.54553; found 481.54507.

$N^1$,$N^3$,$N^5$-Tris(8-(didodecylamino)octyl)adamantane-1,3,5-tricarboxamide 4g Lipidoid 4g was prepared from adamantane-1,3,5-tricarboxylic acid (40 mg, 0.149 mmol), HCTU (256 mg, 0.596 mmol, 4 eq.), DIPEA (0.416 ml, 2.39 mmol, 16 eq.) and diamine 3g (286 mg, 0.596 mmol, 4 eq.) according to the procedure described for compound 4a in Example 1; lipidoid 4g (211 mg, 85.4%; $R_f$ 0.60 in mobile phase D2 on a TLC plate pre-saturated with ammonia, detection with ninhydrin) was obtained as a viscous yellowish oil. $^1$H NMR (600 MHz, $CDCl_3$): δ=8.03, 3.21, 3.09, 3.07, 2.35, 1.985, 1.82, 1.815, 1.71, 1.51, 1.335, 1.33, 1.29, 1.28, 1.25-1.33, 1.25, 0.88 ppm. $^{13}$C NMR (150.9 MHz, $CDCl_3$): δ=177.22, 54.04, 53.07, 41.56, 40.01, 39.08, 36.95, 31.89, 29.60, 29.49, 29.40, 29.32, 29.06, 28.45, 28.42, 28.30, 26.53, 26.13, 26.01, 23.88, 23.45, 22.67, 14.10 ppm. IR ($CCl_4$): $\nu_{max}$/$cm^{-1}$=3439 w (free) and 3341, 3196 w (bound) (ν NH); 1635, 1627 w (amide I); 1533 w (amide II); 2954 m, sh ($\nu_{as}CH_3$); 2873 m, sh ($\nu_s$ $CH_3$); 1467 m and 1457 w, sh ($\beta_s$ $CH_2$ and $\delta_{as}$ $CH_3$); 2927 vs ($\nu_{as}$ $CH_2$); 2856 s ($\nu_s$ $CH_2$); 1378 w ($\delta_s$ $CH_3$); 2810 vw, sh ($\nu_s$ $\underline{CH_2}NR_2$). HRMS: m/z calculated for $C_{109}H_{215}N_6O_3$ $[M+H]^+$ 1656.6856; found 1656.6882.

Example 8

1,2-Epoxydodecane 6

N-chlorosuccinimide (NCS, 3.44 g, 25.77 mmol, 0.95 eq.) and L-proline (0.937 g, 8.14 mmol, 0.30 eq.) were added to a solution of n-dodecylaldehyde (6.0 ml, 27.13 mmol) in acetonitrile (70 ml), cooled to 0° C. in an ice bath, and the mixture was stirred at 0° C. for 2 h. Then the solution was diluted with ethanol (40 ml), $NaBH_4$ (2.57 g, 67.82 mmol, 2.5 eq.) was added, and the reaction mixture was stirred at 0° C. for 3.5 h. The solution was poured into a 1000 ml separatory flask, diluted with water (100 ml) and brine (100 ml), and the product was extracted with ethyl acetate (300 ml, 50 ml). The combined organic phase was washed with brine (100 ml), dried over anhydrous sodium sulphate, filtered through an S2 frit, and the solvents were evaporated in an RVE. The crude product was purified by silica gel column chromatography using a linear gradient of ethyl acetate in cyclohexane (0-20%). Chloroalcohol 5 (2.79 g, 46.6%; $R_f$ 0.42 in mobile phase CE20, detection with $KMnO_4$) was obtained as a colorless oil.

A solution of NaOH (11.37 g, 0.284 mmol, 22.5 eq.) in water (49 ml) was added to a solution of chloroalcohol 5 (2.79 g, 12.64 mmol) in dioxane (38 ml), and the mixture was stirred for 30 h at 35° C. The solution was then poured into a 500 ml separatory flask, diluted with water (100 ml), and the product was extracted with DCM (100 ml, 50 ml). The combined organic phase was washed with brine (50 ml), dried over anhydrous sodium sulphate, filtered through an S2 frit, and the solvents were evaporated in an RVE. The crude product was purified by silica gel column chromatography using a linear gradient of ethyl acetate in cyclohexane (0-5%). Epoxide 6 (1.797 g, 77.2%; $R_f$ 0.38 in mobile phase CE5, detection with phosphomolybdic acid/$Ce^{4+}$) was obtained as a colorless oil. $^1$H NMR (400 MHz, $CDCl_3$): δ=0.92 (t, J=6 Hz, 3H), 1.29-1.60 (m, 18H), 2.47-2.49 (m, 1H), 2.76-2.78 (m, 1H), 2.90-2.95 (m, 1H) ppm. $^{13}$C NMR (101 MHz, $CDCl_3$) δ=14.11, 22.68, 25.97, 29.33, 29.45, 29.56, 29.59, 31.90, 32.50, 47.14, 52.42 ppm. IR ($CCl_4$): $\nu_{max}$/$cm^{-1}$=epoxid: 2997 w, sh ($\nu_{as}$ $CH_2$); 1482 w, 1410 w, 1130 w ($\delta_s$ O—$CH_2$); 1259 w ($\nu_s$ skeleton, respiratory); 917 w ($\delta_{as}$ circle); 896 vw ($\delta_{as}$ COC); alif. chain: 2957 s ($\nu_{as}$ $CH_3$); 2928 vs ($\nu_{as}$ $CH_2$); 2872 m ($\nu_s$ $CH_3$); 2856 s ($\nu_s$ $CH_2$); 1467 m and 1458 m ($\beta_s$ $CH_2$ and $\delta_{as}CH_3$); 1379 w ($\delta_s$ $CH_3$), HRMS (EI): m/z calculated for $C_{12}H_{24}O$ $[M]^+$ 184.1827; found 184.1832.

$N^1$,$N^1$-Bis(2-hydroxydodecyl)hexan-1,6-diamine 8

Amine 1e (0.86 g, 3.98 mmol) and epoxide 6 (1.76 g, 9.54 mmol, 2.4 eq.) were mixed in a 4 ml glass vial, and the mixture was heated in the absence of solvent to 80° C. under an argon atmosphere for 24 h. The resulting yellowish liquid was purified by silica gel column chromatography using a linear gradient of D1 in DCM (0-30%). Amine 7 (1.98 g, 85.1%; $R_f$ 0.51 in mobile phase D3, detection with ninhydrin) was obtained as a yellowish oil.

The deprotection of amine 7 was performed in a mixture of TFA (4 ml) and DCM (6 ml) according to the procedure described for compound 2a in Example 1; diamine 8 (1.271 g, 77.4%; $R_f$ 0.20 in mobile phase D2, detection with ninhydrin) was obtained as a viscous yellowish oil. $^1$H NMR (600 MHz, $CDCl_3$): δ=3.65, 3.63, 2.84, 2.82, 2.565, 2.55, 2.41, 2.325, 1.60, 1.59, 1.41, 1.38, 1.35, 1.30-1.48, 1.28, 1.25-1.29, 1.25, 0.87 ppm. $^{13}$C NMR (150.9 MHz, $CDCl_3$): δ=69.39, 67.71, 62.72, 61.05, 55.78, 54.77, 40.86, 40.56, 35.22, 35.08, 31.90, 30.45, 29.6-29.9, 29.33, 25.65-26.77, 22.67, 14.10 ppm. IR ($CCl_4$): $\nu_{max}$/$cm^{-1}$=3412 w, vbr (ν OH); 1077 w, vbr (ν C—OH); 1621 vw, vbr ($\beta_s$ $NH_2$); 1090 w (ν C—$NH_2$); 2956 m, sh ($\nu_{as}$ $CH_3$); 2928 vs ($\nu_{as}$ $CH_2$); 2871 m ($\nu_s$ $CH_3$); 2855 s ($\nu_s$ $CH_2$); 2810 w, sh ($\nu_s$ N—$\underline{CH_2}$); 1467 w and 1457 w ($\beta_s$ $CH_2$ and $\delta_{as}$ $CH_3$); 1378 vw ($\delta_s$ $CH_3$); 722 vw ($\beta_{as}$ and $\gamma_{as}$ $CH_2$). HRMS (ESI): m/z calculated for $C_{30}H_{65}N_2O_2$ $[M+H]^+$ 485.50406; found 485.50461.

$N^1$,$N^3$,$N^5$-Tris(6-(bis(2-hydroxydodecyl)amino)hexyl)adamantane-1,3,5-tricarboxamide 9

Lipidoid 9 was prepared from adamantane-1,3,5-tricarboxylic acid (40 mg, 0.149 mmol), HCTU (256 mg, 0.596 mmol, 4 eq.), DIPEA (0.416 ml, 2.39 mmol, 16 eq.) and diamine 8 (289 mg, 0.596 mmol, 4 eq.) according to the procedure described for compound 4a in Example 1; lipidoid 9 (188 mg, 75.5%; $R_f$ 0.43 in mobile phase D2, detection with ninhydrin) was obtained as a viscous yellowish oil. $^1$H NMR (600 MHz, $CDCl_3$): δ=6.97, 4.10, 4.075, 4.04, 4.00, 3.38, 3.31, 3.28, 3.24, 3.21, 3.19, 3.16, 3.11, 2.34, 2.14, 1.93, 1.87, 1.28, 1.25-1.31, 1.25, 0.88 ppm. $^{13}$C NMR (150.9 MHz, $CDCl_3$): δ=177.50, 66.38, 65.92, 65.10, 64.73, 61.43, 61.23, 60.55, 59.64, 57.63, 54.48, 53.38, 41.70, 39.42, 39.23, 37.16, 31.90, 29.63, 29.56, 29.52, 29.34, 28.39, 22.68, 14.11 ppm. IR ($CCl_4$): $\nu_{max}$/$cm^{-1}$=3300-3500 m, br (ν OH); 1090 w (ν C—OH); 3439 w (free) and 3344 w (bound) (ν NH); 1635 m (amide I); 1536 m (amide II); 2956 m, sh ($\nu_{as}$ $CH_3$); 2873 m, sh ($\nu_s$ $CH_3$); 2927 vs ($\nu_{as}$ $CH_2$); 2855 s ($\nu_s$ $CH_2$); 1378 w ($\delta_s$ $CH_3$); 2808 w, sh ($\nu_s$ $\underline{CH_2}NR_2$); 721 w ($\beta_s$ $CH_2$). HRMS (MALDI): m/z calculated for $C_{103}H_{203}N_6O_9$ $[M+H]^+$ 1668.5612; found 1668.5628.

Example 9

Linoleylaldehyde 10

Dess-Martin periodinane (4.45 g, 10.49 mmol, 1.3 eq.) was added to a solution of linoleyl alcohol (2.50 ml, 8.07 mmol) in DCM (120 ml), cooled to 0° C. in an ice bath, and the mixture was stirred at 0° C. for 4 h. The reaction was then quenched by the addition of sodium thiosulphate solution (20 g $Na_2S_2O_3 \cdot 5H_2O$/100 ml $H_2O$) and saturated aqueous sodium bicarbonate solution (50 ml), and stirred for 1 h at rt until the initially milky solution turned clear. The solution was poured into a 1000 ml separatory flask, diluted with water (150 ml), and the product was extracted with DCM (150 ml, 2×50 ml). The combined organic phase was washed with brine (150 ml), dried over anhydrous sodium sulphate, filtered through an S2 frit, and the solvents were evaporated in an RVE. The crude material was purified by silica gel column chromatography (isocratic conditions, 5% ethyl acetate in cyclohexane). Aldehyde 10 (1.271 g, 59.6%; $R_f$ 0.36 in mobile phase CE5, detection with KMnO4) was obtained as a colorless oil.

$N^1$,$N^1$-Di((9Z,12Z)-octadeca-9,12-dien-1-yl)hexane-1,6-diamine 12

Amine 11 was prepared from amine 1e (0.345 g, 1.59 mmol), aldehyde 10 (1.27 g, 4.78 mmol, 3 eq.) and sodium triacetoxyborohydride (1.01 g, 4.78 mmol, 3 eq.) according to the procedure described for compound 2a in Example 1. Amine 11 was obtained as a yellowish oil (1.08 g, 94.9%; $R_f$ 0.18 in mobile phase CE20, detection with ninhydrin).

The deprotection of amine 11 was performed in a mixture of TFA (4 ml) and DCM (5 ml) according to the procedure described for 2a in Example 1; diamine 12 (0.594 g, 64.0%; $R_f$ 0.13 in mobile phase D2, detection with ninhydrin) was obtained as a yellowish oil. $^1$H NMR (600 MHz, $CDCl_3$): δ=5.30-5.40, 2.765, 2.73, 2.67, 2.59, 2.04, 1.51, 1.385, 1.37, 1.34, 1.295, 1.29, 1.28-1.34, 1.28, 0.88 ppm. $^{13}$C NMR (150.9 MHz, $CDCl_3$): δ=130.19, 130.06, 127.99, 127.89, 53.49, 53.45, 41.67, 32.52, 31.50, 29.62, 29.46, 29.20-29.48, 27.37, 27.20, 27.18, 26.52, 25.61, 22.56, 14.06 ppm. IR ($CCl_4$): $\nu_{max}$/cm$^{-1}$=3011 s ($\nu_{as}$=CH); 1646-1673 m (ν C═C); 3455 w ($\nu_{as}$ $NH_2$); 3394 ($\nu_s$ $NH_2$); 1620 w ($\beta_s$ $NH_2$); 1087 m (ν C—$NH_2$); 2957 s, sh ($\nu_{as}$ $CH_3$); 2928 vs ($\nu_{as}$ $CH_2$); 2873 s, sh ($\nu_s$ $CH_3$); 2856 vs ($\nu_s$ $CH_2$); 2801 m ($\nu_s$ N—$\underline{CH_2}$); 1467 m and 1457 m, sh ($\beta_s$ $CH_2$ and $\delta_{as}$ $CH_3$); 1378 m ($\delta_s$ $CH_3$); 721 m ($\beta_{as}$ and $\gamma_{as}$ $CH_2$). HRMS: m/z calculated for $C_{42}H_1N_2$ [M+H]$^+$ 613.63943; found 613.63899.

$N^1$,$N^3$,$N^5$-Tris(6-(bis((9Z,12Z)-octadeca-9,12-dien-1-yl)amino)hexyl)adamantane-1,3,5-tricarboxamide 13

Lipidoid 13 was prepared from adamantane-1,3,5-tricarboxylic acid (30 mg, 0.112 mmol), HCTU (192 mg, 0.447 mmol, 4 eq.), DIPEA (0.312 ml, 2.39 mmol, 16 eq.) and diamine 12 (274 mg, 0.447 mmol, 4 eq.) according to the procedure described for compound 4a in Example 1; lipidoid 13 (154 mg, 67.1%; $R_f$ 0.48 in mobile phase D2, detection with ninhydrin) was obtained as a viscous yellowish oil. $^1$H NMR (600 MHz, $CDCl_3$): δ=6.32, 5.37, 5.32, 3.23, 2.76, 2.31, 2.04, 1.90, 1.81, 1.52, 1.35, 1.305, 1.295, 1.29, 1.28-1.35, 1.28, 0.88 ppm. $^{13}$C NMR (150.9 MHz, $CDCl_3$): δ=176.42, 130.21, 129.99, 128.04, 127.87, 52.94, 41.72, 39.98, 38.99, 37.77, 31.50, 29.60, 29.18, 29.08, 29.0-29.7, 28.57, 27.18, 26.26, 25.61, 22.55, 14.07 ppm. IR ($CCl_4$): $\nu_{max}$/cm$^{-1}$=3011 m ($\nu_{as}$=CH); 1661 m (ν C═C); 3464 w (free) and 3347 w (bound) (ν NH); 1645 m, sh (amide I); 1534 w (amide II); 2957 m, sh ($\nu_{as}$ $CH_3$); 2873 m, sh ($\nu_s$ $CH_3$); 2929 vs ($\nu_{as}$ $CH_2$); 2856 s ($\nu_s$ $CH_2$); 1378 and 1366 w ($\delta_s$ $CH_3$); 1086 w, sh (ν C—N); 722 w ($\beta_{as}$ and $\gamma_{as}$ $CH_2$). HRMS (MALDI): m/z calculated for $C_{139}H_{251}N_6O_3$ [M+H]$^+$ 2052.9667; found 2052.9672.

Example 10

8-((tert-Butyldiphenylsilyl)oxy)octane-1-ol 14

Tert-butyldiphenylchlorosilane (17.50 ml, 68.39 mmol, 1 eq.) was added to a solution of 1,8-octanediol (10.0 g, 68.39 mmol) and imidazole (5.59 g, 82.06 mmol, 1.2 eq.) in DCM (250 ml), and the reaction mixture was stirred for 24 h at rt. The solution was poured into a 1000 ml separatory flask, diluted with water (400 ml) and brine (100 ml), and the product was extracted with DCM (2×100 ml). The combined organic phase was washed with brine (100 ml), dried over anhydrous sodium sulphate, filtered through an S2 frit, and the solvents were evaporated in an RVE. The crude product was purified by silica gel column chromatography using a linear gradient of ethyl acetate in cyclohexane (0-30%). Alcohol 14 (13.65 g, 51.9%; $R_f$ 0.35 in mobile phase CE20, detection with $KMnO_4$) was obtained as a colorless oil. $^1$H NMR (400 MHz, $CDCl_3$): δ=1.08 (s, 9H), 1.31-1.41 (m, 8H), 1.55-1.62 (m, 4H), 3.64-3.70 (m, 4H), 7.38-7.47 (m, 6H), 7.69-7.71 (m, 4H) ppm. $^{13}$C NMR (101 MHz, $CDCl_3$): δ=19.24, 25.68, 25.72, 26.89, 29.33, 29.38, 32.56, 32.79, 63.09, 63.99, 127.57, 129.48, 134.19, 135.58 ppm. IR ($CCl_4$): $\nu_{max}$/cm$^{-1}$=3072 m (20a); 3053 m (20b); 2529 s, sh (tBu, $\nu_{as}$ $CH_3$); 2898 s, sh (tBu, $\nu_s$ $CH_3$); 1590, 1568 (8a, 8b); 1487 m (19a); 1463 m, 1473 s (tBu, $\delta_{as}$ $CH_3$); 1428 s (19b); 1390 m, 1362 m (tBu, $\delta_s$ $CH_3$); 1189 m; 1112 vs, 1094 vs ($\nu_{as}$ Si-Ph); 1030 m (18a); 1008 m (δ Ph-Si); 939 m (r $CH_3$); 701 vs ($\nu_s$ COSi); 688 m (4); 622 m (6b); 614 s (6a); 505 s (16b); 489 m (δ Si-Ph); 2932 vs ($\nu_{as}$ $CH_2$); 2858 vs ($\nu_s$ $CH_2$); 3636 m, 3341 m, br ($\nu_s$ OH); 1057 m ($\nu_s$ C—OH). HRMS (ESI): m/z calculated for $C_{24}H_{36}O_2NaSi$ [M+Na]$^+$ 407.23768; found 407.23742.

8-((tert-Butyldiphenylsilyl)oxy)octanoic acid 15

Dess-Martin periodinane (19.54 g, 46.07 mmol, 1.3 eq.) was added to a solution of alcohol 14 (13.63 g, 35.44 mmol) in DCM (250 ml), cooled to 0° C. in an ice bath, and the mixture was stirred at 0° C. for 4 h. The reaction was then quenched by the addition of sodium thiosulphate solution (50 g $Na_2S_2O_3 \cdot 5H_2O$/150 ml $H_2O$) and saturated aqueous sodium bicarbonate solution (100 ml), and stirred for 1 h at rt until the initially milky solution turned clear. The solution was poured into a 1000 ml separatory flask, diluted with water (200 ml), and the product was extracted with DCM (200 ml, 2×50 ml). The combined organic phase was washed with brine (200 ml), dried over anhydrous sodium sulphate, filtered through an S2 frit, and the solvents were evaporated in an RVE. 13.56 g of a colourless oil were obtained.

The obtained residue was dissolved in a 2 l flask in a mixture of acetone (450 ml) and water (90 ml); 2-methyl-2-butene (15.02 ml, 141.8 mmol, 4 eq.) and $NaH_2PO_4 \cdot 2H_2O$ (11.06 g, 70.88 mmol, 2 eq.) were added to the solution, and the suspension was cooled to 0° C. in an ice bath. A solution of sodium chlorite (9.62 g, 106.32 mmol, 3 eq.) in water (60 ml) was then added gradually from a dropping funnel over 30 min, the reaction mixture was removed from the cooling bath, and stirred vigorously at rt for 12 h. The solution was poured into a 1000 ml separatory flask, diluted with a solution of citric acid (70 g) in water (300 ml), and the product was extracted with diethyl ether (300 ml, 50 ml). The combined organic phase was washed with brine (300 ml), dried over anhydrous sodium sulphate, filtered through an S2 frit, and the solvents were evaporated in an RVE. The crude product was purified by silica gel column chromatography (isocratic conditions, 5% methanol in chloroform). Acid 15 (12.92 g, 91.5%; $R_f$ 0.35 in mobile phase MeOH—$CHCl_3$ 5:95 (v/v), detection with $KMnO_4$) was obtained as a viscous colourless oil. $^1H$ NMR (400 MHz, $CDCl_3$): δ=1.05 (s, 9H), 1.27-1.39 (m, 6H), 1.51-1.66 (m, 4H), 2.34 (t, J=7.5 Hz, 2H), 3.65 (t, J=6.5 Hz, 2H), 7.36-7.44 (m, 6H), 7.66-7.68 (m, 4H) ppm. $^{13}C$ NMR (101 MHz, $CDCl_3$): δ=19.23, 24.63, 25.59, 26.89, 28.97, 29.02, 32.48, 33.95, 63.91, 127.57, 129.49, 134.15, 135.58, 179.60 ppm. IR ($CCl_4$): $\nu_{max}$/cm$^{-1}$=3534 w (ν OH, monomer); 3100 w, 2740 w, 2674 w (ν OH, dimer); 1711 vs (ν C═O); 1413 w, 1289 w (ν CO and δ COH); 2561 m, sh (tBu, $\nu_{as}$ $CH_3$); 2898 m, sh (tBu, $\nu_s$ $CH_3$); 1590 w; 1487 w (19a); 1463 m, 1472 m (tBu, $\delta_{as}$ $CH_3$); 1429 m (19b); 1390 w, 1362 w (tBu, $\delta_s$ $CH_3$); 1112 s, ($\nu_{as}$ COSi); 1093 m (18b); 1030 w; 1008 w (δ Ph-Si); 940 w (r $CH_3$); 701 s (4); 688 w (SiOC); 622 w (6b); 614 m (6a); 505 w (16b); 2932 s ($\nu_{as}$ $CH_2$); 2858 m ($\nu_s$ $CH_2$). HRMS (ESI): m/z calculated for $C_{24}H_{33}O_3Si$ $[M+H]^+$ 397.22044; found 397.22018.

(Z)-Non-2-en-1-yl-8-hydroxyoctanoate 17

Diisopropylcarbodiimide (1.08 ml, 6.90 mmol, 1.1 eq.) and 4-dimethylaminopyridine (23.0 mg, 0.188 mmol, 0.03 eq.) were added to a solution of acid 15 (2.50 g, 6.27 mmol) in DCM (100 ml), cooled to 0° C. in an ice bath, and the mixture was stirred at 0° C. for 30 min. Then trans-2-nonen-1-ol (1.37 ml, 8.15 mmol, 1.3 eq.) was added, and the reaction mixture was stirred for 12 h at rt. The solvent was evaporated in an RVE, and the residue was purified by silica gel column chromatography (isocratic conditions, 5% ethyl acetate in cyclohexane). Ester 16 (2.784 g, 84.9%; $R_f$ 0.61 in mobile phase CE5, detection with $KMnO_4$) was obtained as a colorless oil.

A solution of tetrabutylammonium fluoride monohydrate (2.95 g, 10.56 mmol, 2 eq.) in tetrahydrofuran (10 ml), was added to a solution of ester 16 (2.76 g, 5.28 mmol) in tetrahydrofuran (40 ml), and the reaction the mixture was stirred for 20 h at rt. The solution was poured into a 500 ml separatory flask, diluted with 10% aqueous ammonium chloride solution (150 ml), and the product was extracted with diethyl ether (150 ml, 50 ml). The combined organic phase was washed with brine (100 ml), dried over anhydrous sodium sulfate, filtered through an S2 frit, and the solvents were evaporated in an RVE. The crude product was purified by silica gel column chromatography using a linear gradient of ethyl acetate in cyclohexane (0-45%). Alcohol 17 (1.311 g, 87.3%; $R_f$ 0.61 in mobile phase CE50, detection with $KMnO_4$) was obtained as a slightly yellowish oil. $^1H$ NMR (400 MHz, $CDCl_3$): δ=0.87 (t, J=6 Hz, 3H), 1.26-1.38 (m, 14H), 1.51-1.66 (m, 4H), 2.07-2.12 (m, 2H), 2.30 (t, J=7.5 Hz, 2H), 3.63 (t, J=6.6 Hz, 2H), 4.61-4.62 (m, 2H), 5.48-5.55 (m, 1H), 5.60-5.67 (m, 1H) ppm. $^{13}C$ NMR (101 MHz, $CDCl_3$): δ=14.07, 22.60, 24.88, 25.54, 27.54, 28.86, 29.02, 29.07, 29.39, 31.68, 32.68, 34.30, 60.22, 62.97, 123.34, 135.45, 173.75 ppm. IR ($CCl_4$): $\nu_{max}$/cm$^{-1}$=3637 w, 3453 w (ν OH); 1056 m (ν C—OH); 1736 vs (ν C═O); 1238 m, 1170 s (ν C—O); 3025 w ($\nu_{as}$=CH); 1659 w (ν C═C); 1419 w (ρ=C—H); 2955 s ($\nu_{as}CH_3$); 2931 vs ($\nu_a$ $CH_2$); 2858 s ($\nu_s$ $CH_2$); 2872 s, sh ($\nu_s$ $CH_3$); 1466 m and 1457 m ($\beta_s$ $CH_2$ and $\delta_{as}$ $CH_3$); 1378 m ($\delta_s$ $CH_3$); 722 m ($\beta_{as}$ and $\gamma_{as}$ $CH_2$). HRMS (EI): m/z calculated for $C_{17}H_{32}O_3$ $[M]^+$ 284.2351; found 284.2355.

(Z)-Non-2-en-1-yl-8-oxooctanoate 18

Dess-Martin periodinane (2.46 g, 5.80 mmol, 1.3 eq.) was added to a solution of alcohol 17 (1.27 ml, 4.46 mmol) in DCM (100 ml), cooled to 0° C. in an ice bath, and the mixture was stirred at 0° C. for 4 h. The reaction was then quenched by the addition of sodium thiosulfate solution (10 g $Na_2S2O_3$·$5H_2O$/50 ml $H_2O$) and saturated aqueous sodium bicarbonate solution (50 ml), and stirred for 1 h at rt until the initially milky solution turned clear. The solution was poured into a 500 ml separatory flask, diluted with water (100 ml), and the product was extracted with DCM (100 ml, 50 ml). The combined organic phase was washed with brine (150 ml), dried over anhydrous sodium sulfate, filtered through an S2 frit, and the solvents were evaporated in an RVE. The crude product was purified by silica gel column chromatography using a linear gradient of ethyl acetate in cyclohexane (0-30%). Aldehyde 18 (0.573 g, 45.4%; $R_f$ 0.49 in mobile phase CE20, detection with $KMnO_4$) was obtained as a colorless oil. $^1H$ NMR (400 MHz, $CDCl_3$): δ=0.88 (t, J=7 Hz, 3H), 1.26-1.38 (m, 14H), 1.59-1.67 (m, 4H), 2.07-2.12 (m, 2H), 2.30 (t, J=7.5 Hz, 2H), 2.40-2.44 (m, 2H), 4.61-4.63 (m, 2H), 5.48-5.55 (m, 1H), 5.61-5.68 (m, 1H), 9.76 (t, J=1.8 Hz, 1H) ppm. $^{13}C$ NMR (101 MHz, $CDCl_3$): δ=14.07, 21.86, 22.60, 24.71, 27.54, 28.77, 28.83, 28.86, 29.39, 31.68, 34.19, 43.79, 60.25, 123.31, 135.49, 173.59, 202.62 ppm. IR ($CCl_4$): $\nu_m$/cm$^{-1}$=2818 m, 2716 m (aldeh, ν CH); 1733 vs (aldeh, ν C═O); 1395 m, sh (aldeh, δ OCH); 1733 vs (ν C═O); 1244 m, 1172 s (ν C—O); 3026 m ($\nu_{as}$=CH); 1659 w (ν C═C); 2956 s ($\nu_{as}$ $CH_3$); 2930 vs ($\nu_{as}$ $CH_2$); 2858 s ($\nu_s$ $CH_2$); 2873 s, sh ($\nu_s$ $CH_3$); 1466 m a 1462 m ($\beta_s$ $CH_2$ a $\delta_{as}$ $CH_3$); 1378 m a 1373 m ($\delta_s$ $CH_3$). HRMS (ESI): m/z calculated for $C_{17}H_{29}O_4$ $[M-H]^-$ 297.20713; found 297.20722.

$N^1$,$N^1$-Bis(8-((Z)-non-2-en-1-yl)oxy-8-oxooctyl) hexane-1,6-diamine 20

Amine 19 was prepared from amine 1e (140 mg, 0.647 mmol), aldehyde 18 (0.548 g, 1.94 mmol, 3 eq.) and sodium triacetoxyborohydride (0.411 g, 1.94 mmol, 3 eq.) according to the procedure described for 2a in Example 1, except that the reaction mixture was evaporated without prior extraction and the residue was directly purified by chromatography. Amine 19 was obtained as a slightly yellowish oil (0.446 g, 92.0%).

The deprotection of amine 19 was performed in a mixture of TFA (4 ml) and DCM (4 ml) according to the procedure described for 2a in Example 1; diamine 20 (0.333 g, 86.2%; $R_f$ 0.16 in mobile phase D2, detection with ninhydrin) was obtained as a yellowish oil. $^1H$ NMR (600 MHz, $CDCl_3$): δ=5.63, 5.50, 4.61, 3.06, 3.02, 2.99, 2.29, 2.08, 1.82, 1.74, 1.60, 1.57, 1.42, 1.34, 1.28, 1.27, 0.87 ppm. $^{13}C$ NMR (150.9 MHz, $CDCl_3$): δ=173.59, 135.39, 129.29, 60.24, 52.64, 52.19, 39.50, 34.12, 31.64, 29.34, 28.84, 28.82, 28.73, 27.51, 26.60, 25.76, 25.36, 24.69, 23.11, 22.57, 14.05 ppm. IR ($CCl_4$): $\nu_m$/cm$^{-1}$=3446 w ($\nu_{as}$ $NH_2$); 1612 w ($\beta_s$ $NH_2$); 2800 m, sh ($\nu_s$ N—$\underline{CH_2}$); 1736 vs (ν C═O); 1236 m, 1168 s (ν C—O); 3024 m ($\overline{\nu_{as}}$=CH); 1679 w (ν C═C); 1419 w (ρ=CH); 2957 s ($\nu_{as}$ $CH_3$); 2931 vs ($\nu_{as}$ $CH_2$); 2858 s ($\nu_s$ $CH_2$); 2873 s, sh ($\nu_s$ $CH_3$); 1467 m and 1457 m ($\beta_s$ $CH_2$ and $\delta_{as}$ $CH_3$); 1378 m ($\delta_s$ $CH_3$); 721 w ($\beta_{as}$ and $\gamma_{as}$ $CH_2$). HRMS (ESI): m/z calculated for $C_{40}H_{77}O_4N_2$ $[M+H]^+$ 649.58779; found 649.58767.

N$^1$,N$^3$,N$^5$-Tris(6-(bis(8-((Z)-non-2-en-1-yl)oxy-8-oxooctyl)amino)hexyl)adamantane-1,3,5-tricarboxamide 21

Lipidoid 21 was prepared from adamantane-1,3,5-tricarboxylic acid (30 mg, 0.112 mmol), HCTU (192 mg, 0.447 mmol, 4 eq.), DIPEA (0.312 ml, 1.79 mmol, 16 eq.) and diamine 20 (290 mg, 0.447 mmol, 4 eq.) according to the procedure described for compound 4a in Example 1; lipidoid 21 (181 mg, 74.9%; $R_f$ 0.29 in mobile phase D2, detection with ninhydrin) was obtained as a viscous yellowish oil. $^1$H NMR (600 MHz, $CDCl_3$): δ=7.54, 5.63, 5.50, 4.61, 3.29, 3.00, 2.98, 2.34, 2.29, 2.23, 2.08, 1.98, 1.89, 1.76, 1.60, 1.585, 1.42, 1.38, 1.35, 1.28, 1.26, 0.87 ppm. $^{13}$C NMR (150.9 MHz, $CDCl_3$): δ=177.29, 173.53, 135.41, 123.27, 60.25, 52.62, 52.27, 41.72, 39.57, 39.20, 37.12, 34.09, 31.64, 29.34, 28.85, 28.82, 28.74, 28.44, 28.37, 27.51, 26.63, 25.83, 25.56, 24.67, 23.11, 22.57, 14.06 ppm. IR ($CCl_4$): $\nu_{max}/cm^{-1}$=3321 w (ν NH); 1644 m (amide I); 1535 w-m (amide II); 1736 s (ν C═O); 1276 w-m, 1166 m (ν C—O); 3025 w ($\nu_{as}$=CH); 1419 w (ρ=CH); 2956 s, sh ($\nu_{as}$ $CH_3$); 2930 vs ($\nu_{as}$ $CH_2$); 2858 s ($\nu_s$ $CH_2$); 2873 m, sh ($\nu_s CH_3$); 1467 m and 1457 m ($\beta_s$ $CH_2$ and $\delta_{as}$ $CH_3$); 1378 w-m ($\delta_s$ $CH_3$). HRMS (MALDI): m/z calculated for $C_{133}H_{239}N_6O_5$ $[M+H]^+$ 2160.8118; found 2160.8164.

Example 11

3,5,7-Tris((6-(didodecylamino)hexyl)carbamoyl)adamantane-1-carboxylic acid 22

Thionylchloride (300 μl) and DMF (2 μl) was added to adamantane-1,3,5,7-tetracarboxylic acid (21 mg, 0.067 mmol), and the suspension was stirred for 2 h at 70° C. in a closed vial; during this time the suspension turned into a clear homogeneous solution. Excessive $SOCl_2$ was blown out with a stream of dry nitrogen, the residue was dried in vacuo (10 min), and after cooling down to rt was dissolved in 0.5 ml of anhydrous DMF to form a clear solution. Then, a solution of N$^1$,N$^1$-didodecylhexane-1,6-diamine (76 mg, 0.168 mmol, 2.5 eq.) and DIPEA (117 μl, 0.672 mmol, 10 eq.) in a mixture of DCM (1.5 ml) and DMF (0.5 ml), and the reaction mixture was stirred for 10 min at rt. The reaction mixture was then adsorbed onto silica (10 g), and the solvents were evaporated in vacuo. The crude product was purified by flash chromatography on silica (elution with a linear gradient of D1 in DCM, 35-85%) to yield the target compound 22 (45 mg, 41.4%; $R_f$ 0.50 in D2/3, visualization by ninhydrin) as a thick pale yellow oil. $^1$H NMR (600 MHz, $CDCl_3$): δ=7.32, 3.24, 3.05-2.95, 2.16, 1.97, 1.92, 1.80-1.72, 1.55, 1.38-1.23, 0.87 ppm. $^{13}$C NMR (150.9 MHz, $CDCl_3$): δ=176.52, 52.89, 52.20, 42.28, 39.39, 38.96, 31.89, 29.60, 29.50, 29.44, 29.32, 29.10, 28.72, 26.83, 26.23, 25.99, 23.47, 23.14, 22.66, 14.10 ppm. IR ($CCl_4$): $\nu_{max}/cm^{-1}$=3314 w, br (ν NH), 1643 m (amide I) and 1638 w (amide II), 2954 s ($\nu_{as}$ $CH_3$), 2927 vs ($\nu_{as} CH_2$), 2855 s ($\nu_s$ $CH_2$), 1467 m, sh and 1457 m, sh ($\beta_s$ $CH_2$ and $\delta_{as}$ $CH_3$), 1378 w ($\delta_s$ $CH_3$); —COOH dimer: 2591 w, vbr (ν OH), 1715 w (ν C═O), 1411 vw and 1283 w, br (δ COH and ν CCO). HRMS (MALDI): m/z calcd. for $C_{104}H_{203}N_6O_5$ $[M+H]^+$ 1616.5810; found 1616.58014.

N$^1$,N$^3$,N$^5$-Tris(6-(didodecylamino)hexyl)adamantane-1,3,5,7-tetracarboxamide 23

DMF (2 μl) and thionylchloride (24 μl, 0.349 mmol, 14 eq.) were added to a solution of acid 22 (27 mg, 0.017 mmol) in DCM (3.5 ml), and the suspension was stirred for 2 h at rt in a closed vial. The solution was then bubbled with a gentle stream of anhydrous $NH_3$ for 5 min; a white precipitate formed immediately. After 10 min, the reaction mixture was filtered through a celite pad, the filtrate was adsorbed onto silica (10 g), and the solvents were evaporated in vacuo. The crude product was purified by flash chromatography on silica (elution with a linear gradient of D1 in DCM, 30-70%) to yield target compound 23 (15 mg, 55.6%; $R_f$ 0.57 in D2/3, visualization by ninhydrin) as a thick pale yellow oil. $^1$H NMR (600 MHz, $CDCl_3$): δ=6.69, 6.49, 3.21, 2.67, 1.99, 1.96, 1.57, 1.51, 1.33, 1.285, 1.245, 0.87 ppm. $^{13}$C NMR (150.9 MHz, $CDCl_3$): δ=178.41, 175.71, 53.42, 53.07, 42.38, 39.52, 39.40, 39.18, 31.88, 29.62, 29.60, 29.58, 29.55, 29.37, 29.32, 29.02, 27.24, 26.56, 26.21, 22.66, 14.09 ppm. IR ($CCl_4$): $\nu_{max}/cm^{-1}$=3330 w, br (ν NH), 1649 m (amide I) and 1536 w (amide II), 2953 m ($\nu_{as}$ $CH_3$), 2927 vs ($\nu_{as}CH_2$), 2875 m, sh ($\nu_s$ $CH_3$), 2855 s and 2805 vw ($\nu_s$ $CH_2$), 1467 m, and 1457 w, 1438 w, sh ($\beta_s$ $CH_2$ and $\delta_{as}$ $CH_3$), 1378 w ($\delta_s$ $CH_3$); prim. amide: 3199 w, br (ν $NH_2$ viz.), 1697 vw, sh (ν C═O), 1605 w, sh ($\beta_s$ $NH_2$). HRMS (MALDI): m/z calcd. for $C_{104}H_{204}N_7O_4$ $[M+H]^+$ 1615.5969; found 1615.5998.

Example 12

N$^1$,N$^3$,N$^5$-Tris(6-(didodecylamino)hexyl)-N$^7$-(2-hydroxyethyl)adamantane-1,3,5,7-tetracarboxamide 24

DMF (2 μl) and thionylchloride (20 μl, 0.286 mmol, 14 eq.) were added to a solution of acid 22 (33 mg, 0.020 mmol) in DCM (1.5 ml), and the suspension was stirred for 1 h at rt in a closed vial. Ethanolamine (50 μl, 0.816 mmol, 40 eq.) was then added, and a white precipitate formed immediately. After 20 min, the reaction mixture was filtered through a celite pad, the filtrate was adsorbed onto silica (10 g), and the solvents were evaporated in vacuo. The crude product was purified by flash chromatography on silica (elution with a linear gradient of D1 in DCM, 35-85%) to yield the target compound 24 (31 mg, 91.5%; $R_f$ 0.59 in D2/3, visualization by ninhydrin) as a thick pale yellow oil. $^1$H NMR (600 MHz, $CDCl_3$): δ=7.39, 6.92, 3.69, 3.37, 3.22, 3.00, 2.02, 1.96, 1.76, 1.53, 1.40-1.22, 0.86 ppm. $^{13}$C NMR (150.9 MHz, $CDCl_3$): δ=176.76, 176.16, 61.73, 61.38, 52.73, 52.16, 43.13, 42.55, 42.41, 39.54, 39.43, 38.74, 31.86, 29.56, 29.45, 29.40, 29.28, 29.06, 28.64, 26.78, 25.92, 25.64, 23.38, 23.08, 22.64, 14.07 ppm. IR ($CCl_4$): $\nu_{max}/cm^{-1}$=3324 w, br (ν NH), 1646 m (amide I) and 1538 w (amide II), 2955 s ($\nu_{as}CH_3$), 2927 vs ($\nu_{as}$ $CH_2$), 2855 s and 2876 m, sh ($\nu_s$ $CH_3$), 1467 m, 1457 m and 1435 w, sh ($\beta_s$ $CH_2$ and $\delta_{as}$ $CH_3$), 1378 w ($\delta_s$ $CH_3$), 1060 w, vbr, 1036 w, br (ν C—OH). HRMS (MALDI): m/z calcd. for $C_{106}H_{208}N_7O_5$ $[M+H]^+$ 1659.6231; found 1659.62718.

Example 13

N$^1$,N$^3$,N$^5$-Tris(6-(didodecylamino)hexyl)-N$^7$-(1,3-dihydroxypropan-2-yl)adamantane-1,3,5,7-tetracarboxamide 25

Following the procedure outlined for 24, the target compound 25 was prepared from acid 22 (51 mg, 0.031 mmol), and serinol (115 mg, 1.26 mmol, 40 eq.) to yield lipidoid 25 as a thick pale yellow oil (19 mg, 35.6%; $R_f$ 0.59 in D2/3). $^1$H NMR (600 MHz, $CDCl_3$): δ=7.79, 7.21, 7.17, 7.08, 3.26, 3.01, 2.03, 1.92, 1.775, 1.57, 1.385, 1.33, 1.28-1.24 ppm. $^{13}$C NMR (150.9 MHz, $CDCl_3$): δ=176.14, 175.04, 52.74, 52.66, 52.32, 52.17, 39.28-38.65, 31.89, 29.68, 29.59, 29.49, 29.43, 29.32, 29.09, 28.47, 26.83, 26.80, 25.98-25.40, 23.05, 22.67, 14.10 ppm. IR ($CCl_4$): $\nu_{max}$/cm$^{-1}$=3324 w, br (ν NH), 1646 m (amide I) and 1538 w (amide II), 2955 s ($\nu_{as}$ $CH_3$), 2927 vs ($\nu_{as}$ $CH_2$), 2855 s and 2876 m, sh ($\nu_s$ $CH_3$), 1467 m, 1457 m and 1435 w, sh ($\beta_s$ $CH_2$ and $\delta_{as}$ $CH_3$), 1378 w ($\delta_s$ $CH_3$), 1060 w, νbr, 1036 w, br (ν C—OH). HRMS (MALDI): m/z calcd. for $C_{107}H_{210}N_7O_6$ $[M+H]^+$ 1689.6337; found 1616.63235.

Example 14

N$^1$,N$^1$-Di((heptyloxycarbonyl)propyl)hexane-1,6-diamine 28a

Diisopropylcarbodiimide (3.17 ml, 20.24 mmol, 1.3 eq.) and DMAP (57.1 mg, 0.467 mmol, 0.03 eq.) were added to a solution of 4-bromobutyric acid (2.60 g, 15.57 mmol) and 1-heptanol (2.64 ml, 18.68 mmol, 1.2 eq.) in DCM (60 ml), and the mixture was stirred at rt for 1 h. The reaction mixture was then adsorbed onto silica (16 g), and the solvents were evaporated in vacuo. The crude product was purified by flash chromatography on silica (80 g, elution with a linear gradient of ethylacetate in cyclohexane, 0-10%) to yield the target compound 26a (3.916 g, 94.8%; $R_f$ 0.36 in CE5, visualization by $KMnO_4$) as a colorless oil.

Bromoester 26a (1.53 g, 5.78 mmol, 2.5 eq.) and potassium carbonate (3.19 g, 23.11 mmol, 10 eq.) were added to a solution of N-Boc-1,6-diaminohexane (0.50 g, 2.31 mmol) in ACN (10 ml), and the mixture was stirred at 35° C. for 3 days. The reaction mixture was then adsorbed onto silica (16 g), and the solvents were evaporated in vacuo. The crude product was purified by flash chromatography on silica (40 g, elution with a linear gradient of ethylacetate in cyclohexane, 0-100%) to yield the target compound 27a (1.093 g, 80.9%; $R_f$ 0.35 in in CE50 on an $NH_3$-pretreated TLC plate, visualization by ninhydrin) as a pale yellow oil.

The deprotection of amine 27a was performed according to the procedure described for compound 2a in Example 1; diamine 28a (0.817 g, 90.2%; $R_f$ 0.27 in mobile phase D2, detection with ninhydrin) was obtained in the form of a yellowish oil. $^1$H NMR (600 MHz, $CDCl_3$): δ=4.05, 3.63, 3.21, 3.15, 2.91, 2.85, 2.67, 2.53-2.41, 2.32, 1.86, 1.76, 1.61, 1.46, 1.35-1.25, 0.88 ppm. $^{13}$C NMR (150.9 MHz, $CDCl_3$): δ=173.66, 64.58, 53.66, 52.98, 52.87, 40.78, 40.34, 31.87, 31.70, 30.10, 28.90, 28.62, 26.85, 26.45, 25.87, 22.56, 22.02, 14.04 ppm. HRMS (ESI): m/z calcd. for $C_{28}H_{57}N_2O_4$ $[M+H]^+$ 485.43128; found 485.43039.

N$^1$,N$^3$,N$^5$-Tris(6-(bis((heptyloxycarbonyl)propyl)amino)hexyl)adamantane-1,3,5-tricarboxamide 29a Thionylchloride (300 μl) and DMF (2 μl) was added to adamantane-1,3,5-tricarboxylic acid (60 mg, 0.224 mmol), and the suspension was stirred for 1 h at 70° C. in a closed vial; during this time the suspension turned into a clear homogeneous solution. Excessive $SOCl_2$ was blown out with a stream of dry nitrogen, the residue was dried in vacuo (10 min), and after cooling down to rt was dissolved in 0.5 ml of anhydrous DMF to form a clear solution. Then, a solution of amine 28a (434 mg, 0.895 mmol, 4 eq.) and DIPEA (390 μl, 2.24 mmol, 10 eq.) in a mixture of DCM (1.5 ml) and DMF (0.5 ml), and the reaction mixture was stirred for 10 min at rt. The reaction mixture was then adsorbed onto silica (16 g), and the solvents were evaporated in vacuo. The crude product was purified by flash chromatography on silica (40 g, elution with a linear gradient of D1 in DCM, 20-60%) to yield the target compound 29a (115 mg, 30.8%; $R_f$ 0.51 in D2, visualization by ninhydrin) as a thick pale yellow oil. $^1$H NMR (600 MHz, $CDCl_3$): δ=5.76, 4.05, 3.21, 2.42, 2.32, 2.01, 1.84, 1.80, 1.74, 1.61, 1.47, 1.41, 1.34-1.25, 0.88 ppm. $^{13}$C NMR (150.9 MHz, $CDCl_3$): δ=176.01, 173.73, 64.53, 53.72, 53.00, 41.65, 39.77, 39.48, 37.88, 31.96, 31.70, 29.51, 28.90, 28.63, 27.02, 26.76, 25.87, 22.56, 14.05 ppm. HRMS (MALDI): m/z calcd. for $C_{97}H_{179}N_6O_{15}$ $[M+H]^+$ 1668.3423; found 1668.3398.

Example 15

N$^1$,N$^1$-Di((hexyloxycarbonyl)butyl)hexane-1,6-diamine 28b

Following the procedure outlined for 26a, bromoester 26b was prepared from 5-bromopentanoic acid (3.0 g, 16.57 mmol), 1-hexanol (2.48 ml, 19.89 mmol, 1.2 eq.), DIC (3.37 ml, 21.54 mmol, 1.3 eq.) and DMAP (61 mg, 0.497 mmol, 0.03 eq.) to yield 26b as a colorless oil (3.938 g, 89.6%, $R_f$ 0.28 in CE5, visualization by $KMnO_4$).

Following the procedure outlined for 27a, Boc-derivative 27b was prepared from bromoester 26b (1.53 g, 5.78 mmol, 2.5 eq.), N-Boc-1,6-diaminohexane (0.50 g, 2.31 mmol) and potassium carbonate (3.19 g, 23.11 mmol, 10 eq.) to yield 27b as a pale yellow oil (1.080 g, 79.9%, $R_f$ 0.30 in CE50 on an $NH_3$-pretreated TLC plate, visualization by ninhydrin).

The deprotection of amine 27b was performed according to the procedure described for compound 2a in Example 1; diamine 28b (0.788 g, 86.9%; $R_f$ 0.13 in mobile phase D2, detection with ninhydrin) was obtained in the form of a yellowish oil. $^1$H NMR (600 MHz, $CDCl_3$): δ=4.05, 3.63, 3.21, 3.15, 2.79, 2.68, 2.60, 2.51, 2.42, 2.32, 1.61, 1.50, 1.36-1.28, 0.88 ppm. $^{13}$C NMR (150.9 MHz, $CDCl_3$): δ 173.62, 64.52, 53.68, 53.29, 41.22, 40.26, 34.03, 31.41, 28.58, 25.75, 25.57, 22.80, 22.51, 13.98 ppm. HRMS (ESI): m/z calcd. for $C_{28}H_{57}N_2O_4$ $[M+H]^+$ 485.43128; found 485.43052.

N$^1$,N$^3$,N$^5$-Tris(6-(bis((hexyloxycarbonyl)butyl)amino)hexyl)adamantane-1,3,5-tricarboxamide 29b Following the procedure outlined for 29a in Example 14, lipidoid 29b was prepared from adamantane-1,3,5-tricarboxylic acid (53 mg, 0.198 mmol), amine 28b (383 mg, 0.790 mmol, 4 eq.) and DIPEA (344 μl, 1.98 mmol, 10 eq.) to yield 29b as a thick pale yellow oil (191 mg, 57.9%, $R_f$ 0.48 in D2, visualization by ninhydrin). $^1$H NMR (600 MHz, $CDCl_3$): δ=5.72, 4.05, 3.21, 2.38, 2.35, 2.30, 2.01, 1.83, 1.80, 1.61, 1.44, 1.40, 1.35-1.27, 0.88 ppm. $^{13}$C NMR (150.9 MHz, $CDCl_3$): δ=175.96, 173.77, 64.44, 53.98, 53.63, 41.64, 39.73, 39.55, 37.92, 34.27, 31.42, 29.59, 28.60, 27.22, 26.89, 26.63, 25.58, 23.01, 22.52, 13.99 ppm. HRMS (MALDI): m/z calcd. for $C_{97}H_{179}N_6O_{15}$ $[M+H]^+$ 1668.3428; found 1668.3418.

Example 16

N$^1$,N$^1$-Di((nonyloxycarbonyl)propyl)hexane-1,6-diamine 28c

Following the procedure outlined for 26a, bromoester 26c was prepared from 4-bromobutyric acid (2.60 g, 15.57 mmol), 1-nonanol (3.26 ml, 18.68 mmol, 1.2 eq.), DIC (3.17 ml, 20.24 mmol, 1.3 eq.) and DMAP (57 mg, 0.467 mmol, 0.03 eq.) to yield 26c as a colorless oil (4.025 g, 88.2%, $R_f$ 0.32 in CE5, visualization by $KMnO_4$).

Following the procedure outlined for 27a, Boc-derivative 27c was prepared from bromoester 26c (1.25 g, 4.28 mmol, 2.5 eq.), N-Boc-1,6-diaminohexane (0.370 g, 1.71 mmol) and potassium carbonate (2.36 g, 17.10 mmol, 10 eq.) to yield 27c as a pale yellow oil (0.848 g, 77.3%, $R_f$ 0.45 in CE50 on an $NH_3$-pretreated TLC plate, visualization by ninhydrin).

The deprotection of amine 27c was performed according to the procedure described for compound 2a in Example 1; diamine 28c (0.631 g, 88.2%; $R_f$ 0.29 in mobile phase D2, detection with ninhydrin) was obtained in the form of a yellowish oil. $^1$H NMR (600 MHz, $CDCl_3$): δ=4.66, 4.05, 3.16, 2.91, 2.63, 2.59, 2.53, 2.48, 2.34, 1.81, 1.70, 1.61, 1.54, 1.47, 1.42, 1.35-1.24, 0.87 ppm. $^{13}$C NMR (150.9 MHz, $CDCl_3$): δ=173.39, 64.72, 64.66, 52.53, 31.84, 31.59, 29.46, 29.25, 29.22, 28.61, 28.60, 25.91, 25.90, 22.64, 14.08 ppm. HRMS (ESI): m/z calcd. for $C_{32}H_{65}N_2O_4$ [M+H]$^+$ 541.49388; found 541.49303.

N$^1$,N$^3$,N$^5$-Tris(6-(bis((nonyloxycarbonyl)propyl) amino)hexyl)adamantane-1,3,5-tricarboxamide 29c Following the procedure outlined for 29a in Example 14, lipidoid 29c was prepared from adamantane-1,3,5-tricarboxylic acid (42 mg, 0.157 mmol), amine 28c (339 mg, 0.626 mmol, 4 eq.) and DIPEA (273 μl, 1.57 mmol, 10 eq.) to yield 29c as a thick pale yellow oil (134 mg, 46.6%, $R_f$ 0.56 in D2, visualization by ninhydrin). $^1$H NMR (600 MHz, $CDCl_3$): δ=5.72, 4.05, 3.21, 2.40, 2.36, 2.31, 2.01, 1.83, 1.80, 1.72, 1.61, 1.47, 1.38, 1.33-1.24, 0.87 ppm. $^{13}$C NMR (150.9 MHz, $CDCl_3$): δ=175.96, 173.84, 64.48, 53.80, 53.12, 41.65, 39.74, 39.54, 37.92, 32.06, 31.84, 29.47, 29.26, 29.22, 28.64, 25.92, 22.64, 14.09 ppm. HRMS (MALDI): m/z calcd. for $C_{109}H_{203}N_6O_{15}$ [M+H]$^+$ 1836.5306; found 836.5319.

Example 17

N$^1$,N$^1$-Di((octyloxycarbonyl)butyl)hexane-1,6-diamine 28d

Following the procedure outlined for 26a, bromoester 26d was prepared from 5-bromopentanoic acid (3.0 g, 16.57 mmol), 1-octanol (3.13 ml, 19.89 mmol, 1.2 eq.), DIC (3.37 ml, 21.54 mmol, 1.3 eq.) and DMAP (61 mg, 0.497 mmol, 0.03 eq.) to yield 26d as a colorless oil (4.327 g, 89.0%, $R_f$ 0.32 in CE5, visualization by $KMnO_4$).

Following the procedure outlined for 27a, Boc-derivative 27d was prepared from bromoester 26d (1.73 g, 5.89 mmol, 2.5 eq.), N-Boc-1,6-diaminohexane (0.510 g, 2.36 mmol) and potassium carbonate (3.26 g, 23.58 mmol, 10 eq.) to yield 27d as a pale yellow oil (1.241 g, 82.1%, $R_f$ 0.18 in CE50 on an $NH_3$-pretreated TLC plate, visualization by ninhydrin).

The deprotection of amine 27d was performed according to the procedure described for compound 2a in Example 1; diamine 28d (1.09 g, quantitative; $R_f$ 0.22 in mobile phase D2, detection with ninhydrin) was obtained in the form of a yellowish oil. $^1$H NMR (600 MHz, $CDCl_3$): δ=8.22, 4.86, 4.05, 3.04, 2.37, 1.75, 1.67, 1.61, 1.48, 1.40, 1.32-1.25, 0.88 ppm. $^{13}$C NMR (150.9 MHz, $CDCl_3$): δ=172.99, 64.85, 52.44, 51.90, 39.41, 33.13, 31.75, 29.18, 29.14, 28.54, 26.54, 25.86, 25.49, 24.88, 22.60, 21.83, 14.05 ppm. HRMS (ESI): m/z calcd. for $C_{32}H_{65}N_2O_4$ [M+H]$^+$ 541.49388; found 541.49297.

N$^1$,N$^3$,N$^5$-Tris(6-(bis((octyloxycarbonyl)butyl) amino)hexyl)adamantane-1,3,5-tricarboxamide 29d Following the procedure outlined for 29a in Example 14, lipidoid 29d was prepared from adamantane-1,3,5-tricarboxylic acid (70 mg, 0.261 mmol), amine 28d (565 mg, 1.04 mmol, 4 eq.) and DIPEA (455 μl, 2.61 mmol, 10 eq.) to yield 29d as a thick pale yellow oil (229 mg, 47.8%, $R_f$ 0.58 in D2, visualization by ninhydrin). $^1$H NMR (600 MHz, $CDCl_3$): δ=5.79, 4.05, 3.21, 2.44, 2.31, 2.01, 1.84, 1.80, 1.61, 1.47, 1.34-1.24, 0.88 ppm. $^{13}$C NMR (150.9 MHz, $CDCl_3$): δ=176.03, 173.63, 64.50, 53.54, 41.65, 39.77, 39.45, 37.88, 34.12, 31.76, 29.48, 29.20, 29.16, 28.63, 25.91, 22.87, 22.61, 14.07 ppm. HRMS (ESI): m/z calcd. for $C_{109}H_{203}N_6O_{15}$ [M+H]$^+$ 1836.53010; found 1836.52959.

Example 18

N$^1$,N$^1$-Di((heptyloxycarbonyl)pentyl)hexane-1,6-diamine 28e

Following the procedure outlined for 26a, bromoester 26e was prepared from 6-bromohexanoic acid (3.0 g, 15.38 mmol), 1-heptanol (2.61 ml, 18.46 mmol, 1.2 eq.), DIC (3.13 ml, 19.99 mmol, 1.3 eq.) and DMAP (56 mg, 0.461 mmol, 0.03 eq.) to yield 26e as a colorless oil (4.177 g, 92.6%, $R_f$ 0.27 in CE5, visualization by $KMnO_4$).

Following the procedure outlined for 27a, Boc-derivative 27e was prepared from bromoester 26e (1.49 g, 5.08 mmol, 2.5 eq.), N-Boc-1,6-diaminohexane (0.440 g, 2.03 mmol) and potassium carbonate (2.81 g, 20.34 mmol, 10 eq.) to yield 27e as a pale yellow oil (1.076 g, 82.5%, $R_f$ 0.15 in CE50 on an $NH_3$-pretreated TLC plate, visualization by ninhydrin).

The deprotection of amine 27e was performed according to the procedure described for compound 2a in Example 1; diamine 28e (0.895 g, 98.6%; $R_f$ 0.17 in mobile phase D2, detection with ninhydrin) was obtained in the form of a yellowish oil. $^1$H NMR (600 MHz, $CDCl_3$): δ=8.40, 4.04, 3.04, 2.99, 2.31, 2.05, 1.72, 1.66, 1.61, 1.48, 1.39, 1.33-1.26, 0.88 ppm. $^{13}$C NMR (150.9 MHz, $CDCl_3$): δ=173.38, 64.64, 52.02, 33.78, 31.68, 28.88, 28.58, 26.70, 26.25, 26.13, 25.83, 25.68, 24.93, 24.20, 22.99, 22.55, 22.48, 14.03 ppm. HRMS (ESI): m/z calcd. for $C_{32}H_{65}N_2O_4$ [M+H]$^+$ 541.49388; found 541.49303.

N$^1$,N$^3$,N$^5$-Tris(6-(bis((heptyloxycarbonyl)pentyl) amino)hexyl)adamantane-1,3,5-tricarboxamide 29e Following the procedure outlined for 29a in Example 14, lipidoid 29e was prepared from adamantane-1,3,5-tricarboxylic acid (55 mg, 0.205 mmol), amine 28e (444 mg, 0.820 mmol, 4 eq.) and DIPEA (357 μl, 2.05 mmol, 10 eq.) to yield 29e as a thick pale yellow oil (150 mg, 39.8%, $R_f$ 0.37 in D2, visualization by ninhydrin). $^1$H NMR (600 MHz, $CDCl_3$): δ=5.72, 4.05, 3.21, 2.37, 2.29, 2.01, 1.83, 1.80, 1.62, 1.47, 1.42, 1.33-1.25, 0.88 ppm. $^{13}$C NMR (150.9 MHz, $CDCl_3$): δ=175.97, 173.84, 64.42, 53.96, 41.64, 39.74, 39.53, 37.91, 34.35, 31.70, 29.59, 28.89, 28.63, 27.14, 25.87, 24.97, 22.56, 14.05 ppm. HRMS (ESI): m/z calcd. for $C_{109}H_{203}N_6O_{15}$ [M+H]$^+$ 1836.53010; found 1836.52930.

Example 19

N[1],N[1]-Di(((nonan-3-yl)oxycarbonyl)propyl)hexane-1,6-diamine 28f

Following the procedure outlined for 26a, bromoester 26f was prepared from 6-bromohexanoic acid (3.2 g, 16.41 mmol), 3-nonanol (2.60 g, 18.05 mmol, 1.1 eq.), DIC (3.27 ml, 21.33 mmol, 1.3 eq.) and DMAP (60 mg, 0.492 mmol, 0.03 eq.) to yield 26f as a colorless oil (2.88 g, 54.5%, $R_f$ 0.42 in CE5, visualization by $KMnO_4$).

Following the procedure outlined for 27a, Boc-derivative 27f was prepared from bromoester 26f (2.82 g, 8.78 mmol, 2.5 eq.), N-Boc-1,6-diaminohexane (0.760 g, 3.51 mmol) and potassium carbonate (4.86 g, 35.13 mmol, 10 eq.) to yield 27f as a pale yellow oil (1.72 g, 70.19%, $R_f$ 0.56 in CE50 on an $NH_3$-pretreated TLC plate, visualization by ninhydrin).

The deprotection of amine 27f was performed according to the procedure described for compound 2a in Example 1; diamine 28f (1.84 g, quantitative; $R_f$ 0.25 in mobile phase D2, detection with ninhydrin) was obtained in the form of a yellowish oil. $^1H$ NMR (600 MHz, $CDCl_3$): δ=8.29, 4.80, 2.99, 2.305, 1.69-1.66, 1.55-1.51, 1.445, 1.38, 1.28-1.24, 0.87, 0.86 ppm. $^{13}C$ NMR (150.9 MHz, $CDCl_3$): δ=173.14, 75.61, 52.10, 39.27, 34.08, 33.56, 31.71, 29.15, 26.90, 26.74, 26.14, 25.69, 25.27, 24.86, 24.33, 22.97, 22.56, 22.51, 14.03, 9.57 ppm. HRMS (ESI): m/z calcd. for $C_{36}H_{73}N_2O_4$ $[M+H]^+$ 597.55649; found 597.55631.

N[1],N[3],N[5]-Tris(6-(bis(((nonan-3yl)oxycarbonyl)propyl)amino)hexyl)adamantane-1,3,5-tricarboxamide 29f Following the procedure outlined for 29a in Example 14, lipidoid 29f was prepared from adamantane-1,3,5-tricarboxylic acid (50 mg, 0.186 mmol), amine 28f (334 mg, 746 mmol, 4 eq.) and DIPEA (325 μl, 1.86 mmol, 10 eq.) to yield 29f as a thick pale yellow oil (237 mg, 63.4%, $R_f$ 0.44 in D2, visualization by ninhydrin). $^1H$ NMR (600 MHz, $CDCl_3$): δ=6.385, 4.79, 3.21, 2.99, 2.305, 2.015, 1.88, 1.80, 1.73, 1.66, 1.55-1.50, 1.38-1.35, 1.27-1.24, 0.865, 0.855 ppm. $^{13}C$ NMR (150.9 MHz, $CDCl_3$): δ=176.57, 173.02, 76.58, 52.43, 51.98, 41.69, 39.89, 38.89, 37.64, 34.09, 33.55, 31.70, 29.14, 28.84, 26.90, 26.28, 26.01, 25.78, 24.39, 23.13, 22.96, 22.55, 14.04, 9.59 ppm. HRMS (MALDI): m/z calcd. for $C_{121}H_{227}N_6O_{15}$ $[M+H]^+$ 2004.7179; found 2004.7187.

Example 20

6-(Di((heptyloxycarbonyl)propyl)amino)hexan-1-ol 30a

Bromoester 26a (1.13 g, 4.27 mmol, 2.5 eq.) and potassium carbonate (2.36 g, 17.07 mmol, 10 eq.) were added to a solution of 6-aminohexan-1-ol (0.20 g, 1.71 mmol) in ACN (10 ml), and the mixture was stirred at 50° C. for 20 h. The reaction mixture was then adsorbed onto silica (16 g), and the solvents were evaporated in vacuo. The crude product was purified by flash chromatography on silica (40 g, elution with a linear gradient of D1 in DCM, 0-50%) to yield the target compound 30a (0.552 g, 63.0%; $R_f$ 0.56 in D2, visualization by $KMnO_4$) as a pale yellow oil.

$^1H$ NMR (600 MHz, $CDCl_3$): δ=4.05, 3.63, 2.52, 2.33, 1.80, 1.61, 1.565, 1.50, 1.375, 1.32-1.27, 0.88 ppm. $^{13}C$ NMR (150.9 MHz, $CDCl_3$): δ=173.54, 64.63, 53.45, 52.82, 32.59, 31.78, 31.69, 28.89, 28.60, 26.95, 25.86, 25.45, 22.55, 21.78, 14.03 ppm. HRMS (ESI): m/z calcd. for $C_2H_{56}NO_5$ $[M+H]^+$ 486.41530; found 486.41467.

tris(6-(Di((heptyloxycarbonyl)propyl))hexyl)adamantane-1,3,5-tricarboxylate 31a

Tetramethylfluoroformamidinium hexafluorophosphate (TFFH, 169 mg, 0.640 mmol, 3.3 eq.) and DIPEA (0.506 ml, 2.91 mmol, 15 eq.) were added to a solution of adamantane-1,3,5-tricarboxylic acid (52 mg, 0.194 mmol) in anhydrous DMF (5 ml), and the solution was stirred for 30 min at 0° C. Then a solution of alcohol 30a (311 mg, 0.640 mmol, 3.3 eq.) and DMAP (7 mg, 0.058 mmol, 0.3 eq.) in DMF (2.0 ml) was added, and the reaction mixture was stirred for 12 h at rt. The solution was poured into a 250 ml separatory flask, diluted with saturated aqueous $NaHCO_3$ (50 ml), and the product was extracted with diethyl ether (100 ml, 2×50 ml). The combined organic phase was washed with brine (50 ml), dried over anhydrous sodium sulphate, filtered through an S2 frit, and the solvents were evaporated in an RVE. The crude product was purified by silica gel column chromatography using a linear gradient of D1 in DCM (0-65%). Lipidoid 31a (33 mg, 10.3%; $R_f$ 0.57 in mobile phase D4, detection with ninhydrin) was obtained in the form of a viscous yellowish oil. $^1H$ NMR (600 MHz, $CDCl_3$): δ=4.05, 2.40, 2.05-1.94, 1.83, 1.61, 1.35-1.25, 0.886 ppm. $^{13}C$ NMR (150.9 MHz, $CDCl_3$): δ=176.02, 64.95, 64.45, 41.35, 39.14, 37.14, 31.67, 28.87, 28.55, 25.83, 22.54, 14.03 ppm. HRMS (MALDI): m/z calcd. for $C_{97}H_{176}N_3O_{18}$ $[M+H]^+$ 1671.2943; found 1671.2973.

Example 21

6-(Di((hexyloxycarbonyl)butyl)amino)hexan-1-ol 30b

Following the procedure outlined for 30a, alcohol 30b was prepared from 6-aminohexan-1-ol (0.20 g, 1.71 mmol), bromoester 26b (1.13 g, 4.27 mmol, 2.5 eq.) and $K_2CO_3$ (2.36 g, 17.07 mmol, 10 eq.) to yield 30b as a pale yellow oil (0.599 g, 72.3%, $R_f$ 0.55 in D2, visualization by $KMnO_4$). $^1H$ NMR (600 MHz, $CDCl_3$): δ=4.04, 3.63, 2.46, 2.32, 1.76, 1.60, 1.56, 1.45, 1.37-1.25, 0.87 ppm. $^{13}C$ NMR (150.9 MHz, $CDCl_3$): δ=173.69, 64.56, 62.79, 53.57, 52.96, 32.64, 31.90, 31.82, 29.45, 29.24, 29.21, 28.61, 27.02, 25.91, 25.51, 22.63, 14.07 ppm.

Tris(6-(di((hexyloxycarbonyl)butyl))hexyl)adamantane-1,3,5-tricarboxylate 31b

Lipidoid 31b was prepared from adamantane-1,3,5-tricarboxylic acid (84 mg, 0.313 mmol), TFFH (273 mg, 1.03 mmol, 3.3 eq.), DIPEA (0.818 ml, 4.179 mmol, 15 eq.), DMAP (11 mg, 0.093 mmol, 0.3 eq.) and alcohol 30b (608 mg, 1.25 mmol, 4 eq.) according to the procedure described for compound 31a in Example 20; lipidoid 31b (55 mg, 10.4%; $R_f$ 0.74 in mobile phase D2, detection with ninhydrin) was obtained as a viscous yellow oil. $^1H$ NMR (600 MHz, $CDCl_3$): δ=4.05, 2.96, 2.37, 2.33, 2.01, 1.94, 1.85-1.78, 1.66, 1.60, 1.38, 1.34-1.28, 0.88 ppm. $^{13}C$ NMR (150.9 MHz, $CDCl_3$): δ=176.01, 172.90, 64.76-64.34, 52.16, 47.81, 46.61, 41.35, 39.14, 37.12, 33.22, 31.38, 28.53, 25.54, 22.50, 22.09, 13.97 ppm. HRMS (MALDI): m/z calcd. for $C_{97}H_{176}N_3O_{18}$ $[M+H]^+$ 1671.2943; found 1671.2910.

Example 22

6-(Di((nonyloxycarbonyl)propyl)amino)hexan-1-ol 30c

Following the procedure outlined for 30a, alcohol 30c was prepared from 6-aminohexan-1-ol (0.20 g, 1.71 mmol), bromoester 26c (1.25 g, 4.27 mmol, 2.5 eq.) and $K_2CO_3$ (2.36 g, 17.07 mmol, 10 eq.) to yield 30c as a pale yellow oil (0.651 g, 70.4%, $R_f$ 0.59 in D2, visualization by $KMnO_4$).

$^1H$ NMR (600 MHz, $CDCl_3$): δ=4.07, 3.65, 3.09, 3.03, 2.45, 2.16, 1.89, 1.61, 1.56, 1.45, 1.34-1.25, 0.88 ppm. $^{13}C$ NMR (150.9 MHz, $CDCl_3$): δ=172.24, 65.25, 62.39, 52.41, 51.55, 32.11, 31.84, 30.65, 29.45, 29.22, 28.54, 26.29, 25.87, 22.65, 18.39, 14.09 ppm.

Tris(6-(di((nonyloxycarbonyl)propyl))hexyl)adamantane-1,3,5-tricarboxylate 31c Lipidoid 31c was prepared from adamantane-1,3,5-tricarboxylic acid (86 mg, 0.320 mmol), TFFH (279 mg, 1.06 mmol, 3.3 eq.), DIPEA (0.838 ml, 4.81 mmol, 15 eq.), DMAP (12 mg, 0.096 mmol, 0.3 eq.) and alcohol 30c (695 mg, 1.28 mmol, 4 eq.) according to the procedure described for compound 31a in Example 20; lipidoid 31c (23 mg, 3.9%; $R_f$ 0.91 in mobile phase D2, detection with ninhydrin) was obtained as a viscous yellow oil. $^1H$ NMR (600 MHz, $CDCl_3$): δ=4.05, 2.37, 2.01, 1.95, 1.83, 1.61, 1.35-1.24, 0.87 ppm. $^{13}C$ NMR (150.9 MHz, $CDCl_3$): δ=176.02, 64.70, 41.35, 39.15, 37.15, 31.82, 29.44, 29.23, 29.20, 28.58, 28.47, 25.88, 22.63, 14.07 ppm. HRMS (MALDI): m/z calcd. for $C_{109}H_{200}N_3O_{18}$ $[M]^+$ 1839.4821; found 1839.4799.

Example 23

6-(Di((octyloxycarbonyl)butyl)amino)hexan-1-ol 30d

Following the procedure outlined for 30a, alcohol 30d was prepared from 6-aminohexan-1-ol (0.20 g, 1.71 mmol), bromoester 26d (1.25 g, 4.27 mmol, 2.5 eq.) and $K_2CO_3$ (2.36 g, 17.07 mmol, 10 eq.) to yield 30d as a pale yellow oil (0.623 g, 67.4%, $R_f$ 0.50 in D2, visualization by $KMnO_4$).

$^1H$ NMR (600 MHz, $CDCl_3$): δ=4.05, 3.63, 2.47, 2.31, 1.61, 1.56, 1.50, 1.37-1.24, 0.87 ppm. $^{13}C$ NMR (150.9 MHz, $CDCl_3$): δ=173.65, 64.52, 62.78, 53.69, 53.42, 34.07, 32.60, 31.75, 29.19, 29.15, 28.61, 27.05, 25.90, 25.49, 22.85, 22.61, 14.06 ppm.

Tris(6-(di((octyloxycarbonyl)butyl))hexyl)adamantane-1,3,5-tricarboxylate 31d Lipidoid 31d was prepared from adamantane-1,3,5-tricarboxylic acid (83 mg, 0.309 mmol), TFFH (270 mg, 1.02 mmol, 3.3 eq.), DIPEA (0.808 ml, 4.64 mmol, 15 eq.), DMAP (11 mg, 0.093 mmol, 0.3 eq.) and alcohol 30d (671 mg, 1.24 mmol, 4 eq.) according to the procedure described for compound 31a in Example 20; lipidoid 31d (147 mg, 25.8%; $R_f$ 0.82 in mobile phase D2, detection with ninhydrin) was obtained as a viscous yellow oil. $^1H$ NMR (600 MHz, $CDCl_3$): δ=4.05, 2.34, 2.01, 1.95, 1.83, 1.78-1.56, 1.36-1.24, 0.87 ppm. $^{13}C$ NMR (150.9 MHz, $CDCl_3$): δ=176.04, 64.76-64.46, 41.36, 39.16, 37.15, 31.75, 29.19, 29.15, 28.60, 25.90, 22.61, 14.06 ppm. HRMS (MALDI): m/z calcd. for $C_{109}H_{200}N_3O_{1s}$ $[M]^+$ 1839.4821; found 1839.4792.

Example 24

Preparation of Transfection Reagents

Reagents were generated by mixing the individual components listed in Table 1 to Table 4. All tables contain the final molar concentrations in the transfection reagent. Stock 5 mM solutions of the individual components in 99.7% ethanol were used for the preparation. Only the DOPE-Cy5 stock solution had a concentration of 0.79 mM and was prepared in chloroform.

TABLE 1

Composition of transfection reagents A01-A10.

| compound | Concentration of individual components in transfection reagents (mM) | | | | | | | | | |
|---|---|---|---|---|---|---|---|---|---|---|
| | A01 | A02 | A03 | A04 | A05 | A06 | A07 | A08 | A09 | A10 |
| 4a | 1.1 | — | — | — | — | — | — | — | — | — |
| 4b | — | 1.1 | — | — | — | — | — | — | — | — |
| 4c | — | — | 1.1 | — | — | — | — | — | — | — |
| 4d | — | — | — | 1.1 | — | — | — | — | — | — |
| 4e | — | — | — | — | 1.1 | — | — | — | — | — |
| 4f | — | — | — | — | — | 1.1 | — | — | — | — |
| 4g | — | — | — | — | — | — | 1.1 | — | — | — |
| 9 | — | — | — | — | — | — | — | 1.1 | — | — |
| 13 | — | — | — | — | — | — | — | — | 1.1 | — |
| 21 | — | — | — | — | — | — | — | — | — | 1.1 |
| cholesterol | 2.18 | 2.18 | 2.18 | 2.18 | 2.18 | 2.18 | 2.18 | 2.18 | 2.18 | 2.18 |
| DOPE | 1.64 | 1.64 | 1.64 | 1.64 | 1.64 | 1.64 | 1.64 | 1.64 | 1.64 | 1.64 |
| DMG-$PEG_{2000}$ | 0.075 | 0.075 | 0.075 | 0.075 | 0.075 | 0.075 | 0.075 | 0.075 | 0.075 | 0.075 |
| DOPE-Cy5 | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ |

TABLE 2

Composition of transfection reagents A11-A13.

| compound | Concentration of individual components in transfection reagents (mM) | | |
|---|---|---|---|
| | A11 | A12 | A13 |
| 23 | 1.1 | — | — |
| 24 | — | 1.1 | — |
| 25 | — | — | 1.1 |
| cholesterol | 2.18 | 2.18 | 2.18 |

TABLE 2-continued

| Composition of transfection reagents A11-A13. | | | |
|---|---|---|---|
| | Concentration of individual components in transfection reagents (mM) | | |
| compound | A11 | A12 | A13 |
| DOPE | 1.65 | 1.65 | 1.65 |
| DMG-PEG$_{2000}$ | 0.075 | 0.075 | 0.075 |

TABLE 3

| Composition of transfection reagents A14-A23. | | | | | | | | | | |
|---|---|---|---|---|---|---|---|---|---|---|
| | Concentration of individual components in transfection reagents (mM) | | | | | | | | | |
| compound | A14 | A15 | A16 | A17 | A18 | A19 | A20 | A21 | A22 | A23 |
| 29a | 1.1 | — | — | — | — | — | — | — | — | — |
| 29b | — | 1.1 | — | — | — | — | — | — | — | — |
| 29c | — | — | 1.1 | — | — | — | — | — | — | — |
| 29d | — | — | — | 1.1 | — | — | — | — | — | — |
| 29e | — | — | — | — | 1.1 | — | — | — | — | — |
| 29f | — | — | — | — | — | 1.1 | — | — | — | — |
| 31a | — | — | — | — | — | — | 1.1 | — | — | — |
| 31b | — | — | — | — | — | — | — | 1.1 | — | — |
| 31c | — | — | — | — | — | — | — | — | 1.1 | — |
| 31d | — | — | — | — | — | — | — | — | — | 1.1 |
| cholesterol | 2.18 | 2.18 | 2.18 | 2.18 | 2.18 | 2.18 | 2.18 | 2.18 | 2.18 | 2.18 |
| DOPE | 1.64 | 1.64 | 1.64 | 1.64 | 1.64 | 1.64 | 1.64 | 1.64 | 1.64 | 1.64 |
| DMG-PEG$_{2000}$ | 0.075 | 0.075 | 0.075 | 0.075 | 0.075 | 0.075 | 0.075 | 0.075 | 0.075 | 0.075 |
| DOPE-Cy5 | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ |

TABLE 4

| Composition of transfection reagents A24-A29 (A26 and A27 are comparative examples). | | | | | | |
|---|---|---|---|---|---|---|
| | Concentration of individual components in transfection reagents (mM) | | | | | |
| compound | A24 | A25 | A26 | A27 | A28 | A29 |
| 4e | 1.1 | 1.1 | — | — | 1.1 | — |
| 4d | — | — | — | — | — | 1.1 |
| D-Lin-MC3-DMA | — | — | 2.5 | — | — | — |
| TT3 | — | — | — | 1.1 | — | — |
| cholesterol | 2.18 | 2.18 | 1.93 | 2.18 | 2.18 | 2.18 |
| DOPE | — | — | — | 1.64 | 1.65 | 1.65 |
| DOPC | 1.64 | — | — | — | — | — |
| DSPC | — | 1.64 | 0.49 | — | — | — |
| DMG-PEG$_{2000}$ | 0.075 | 0.075 | 0.075 | 0.075 | 0.075 | 0.075 |
| DOPE-Cy5 | $1.19 \times 10^{-3}$ | $1.19 \times 10^{-3}$ | $1.19 \times 10^{-3}$ | $1.19 \times 10^{-3}$ | — | — |

Example 25

Preparation of Lipid Nanoparticles (LNP) Containing mRNA

DNA encoding the fluorescent protein mKate2 was amplified from the plasmid pmKate2-C (Evrogen) using the primers (5'-CGCCACCATGGTGAGCGAGCTG-3' (SEQ ID NO. 1); 5'-CCTCCTCCACCTCTGTGCCCCAG-3' (SEQ ID NO. 2)) and cloned into the pET24a vector (Invitrogen) under the T7 promoter. Messenger RNA (mRNA) encoding mKate2 was transcribed in vitro using the Ampliscribe T7-Flash transcription kit (Lucigen) according to the manufacturer's protocol. The RNA cap analog ARCA (Jena Bioscience) was added to the in vitro transcription reaction, and the poly(A) terminus was synthesized using poly(A) polymerase (New England Biolabs) according to the standard protocol.

The mRNA-containing LNPs (mRNA-LNPs) were prepared as follows: 300 μl of a solution of each of the A01-A27 transfection reagents prepared in Example 24 was mixed with a solution of 120 μg of mRNA in 300 μl of 10 mM citrate buffer (pH 3.0) using a "Y" microfluidic device with two inputs and one output for sampling. The lipid mixture and the mRNA solution were injected separately into each inlet by a linear pump at a constant flow rate of 300 μl/min. The resulting 600 μl nanoparticle solution was collected and immediately diluted by the addition of 600 μl PBS; the corresponding nanoparticle samples designated B01-B27 were thus formed from the transfection reagents A01-A27. Each of the mRNA-LNP samples (B01-B27) was prepared in triplicate. The hydrodynamic diameter of freshly formed mRNA-LNPs was measured using dynamic light scattering (NanoZS Zetasizer, Malvern, Worcestershire, UK) at a scattering angle of 173° at 25° C. The hydrodynamic diameter of mRNA-LNPs ranged from 72 to 135 nm with the exception of B18 with diameter of 265 nm (Table 5). In this form, the particles were used for subsequent biological tests.

TABLE 5

| Hydrodynamic diameter of mRNA-LNPs including standard deviation measured by dynamic light scattering. | |
|---|---|
| LNP | Diameter (nm) |
| B01 | 81.5 ± 8.0 |
| B02 | 99.3 ± 2.7 |
| B03 | 85.1 ± 4.1 |
| B04 | 107.7 ± 4.2 |
| B05 | 76.1 ± 1.9 |
| B06 | 72.9 ± 8.6 |
| B07 | 73.6 ± 3.9 |
| B08 | 108.0 ± 18.3 |
| B09 | 90.8 ± 5.5 |
| B10 | 89.5 ± 5.0 |
| B11 | 82.5 ± 0.2 |
| B12 | 85.5 ± 1.1 |
| B13 | 102.1 ± 10.7 |
| B14 | 92.6 ± 5.1 |
| B15 | 118.0 ± 5.5 |
| B16 | 79.4 ± 2.7 |

TABLE 5-continued

Hydrodynamic diameter of mRNA-LNPs including standard deviation measured by dynamic light scattering.

| LNP | Diameter (nm) |
|---|---|
| B17 | 72.2 ± 4.0 |
| B18 | 265.7 ± 19.9 |
| B19 | 71.8 ± 4.2 |
| B20 | 85.7 ± 6.4 |
| B21 | 135.1 ± 1.1 |
| B22 | 80.3 ± 6.7 |
| B23 | 80.1 ± 5.4 |

Example 26

Comparison of mRNA Transfection Using New LNPs In Vitro Using Various Helper Lipids in a Lipid Mixture LNPs B05, B24 and B25 containing mRNA encoding the fluorescent protein mKate2 prepared in triplicate in Example 25 were tested on cells of the human cell line HEK293. Cells were cultured in 96-well plates ($5\times10^4$ cells in 100 μl culture medium per well) in IMDM medium supplemented with 10% FBS at 37° C. in 50% $CO_2$. Cells were transfected with 2 μl of mRNA-LNP (with a final total concentration of all lipid components of 20 μM) and subsequently incubated for 24 hours. Transfections were performed in triplicates. The intensity of Cy5 fluorescence, indicating LNP entry into cells, and mKate2 fluorescence, indicating the translation of mRNA released from LNP after cell transfection, were analysed in a BD LSR Fortessa cytometer.

The novel mRNA-LNPs, whose lipid mixture contained DOPE, DOPC or DSPC helper lipid, were able to efficiently transfect mRNA into the HEK293 cell line, with the most efficient transfection being achieved with mRNA-LNP containing DOPE helper lipid (Table 6).

TABLE 6

Transfection efficiency of new mRNA-LNPs containing helper lipids DOPE (B05), DOPC (B24) or DSPC (B25). The indicated values of the fluorescence intensity of Cy5 and mKate2 are normalized to the control variant of transfection with LNPs containing DOPE (B05).

| LNP | Fluorescence Cy5 | Fluorescence mKate2 |
|---|---|---|
| B05 | 1.00 ± 0.04 | 1.00 ± 0.19 |
| B24 | 0.52 ± 0.01 | 0.18 ± 0.01 |
| B25 | 0.42 ± 0.03 | 0.12 ± 0.02 |

Example 27

Comparison of mRNA Transfection Using New LNPs and mRNA-LNPs Formed by Known Transfection Reagents The transfection efficiency of mRNA-LNP B05 was compared with selected known, highly efficient transfection reagents, namely D-Lin-MC3-DMA (MedChemExpress Europe) and ionisable lipidoid TT3 (Li, B.: *Nano Lett.* 2015, 15, 8099-8107) formulated in Example 25 as B26-B27, and also with Lipofectamine® 2000 reagent (Invitrogen, used according to the standard protocol provided by the manufacturer, designated as Lip2000). Cells of the human cell line HEK293T were cultured in 96-well plates ($5\times10^4$ in 100 μl of culture medium per well) in DMEM medium supplemented with 10% FBS at 37° C. in 5% $CO_2$. Cells were transfected with 2 μl of mRNA-LNP (with a final total concentration of all lipid components of 20 μM) and subsequently incubated for 24 hours. Transfections were performed in triplicates. The fluorescence intensity of mKate2 and the percentage of cells expressing mKate2 were analysed in a BD LSR Fortessa cytometer.

The new mRNA-LNPs (labelled B05) exhibited significantly higher transfection efficiency than known transfection reagents (Table 7).

TABLE 7

Comparison of new mRNA-LNPs with mRNA-LNPs formed by commercial ionisable lipids D-Lin-MC3-DMA (B26), TT3 (B27) and Lipofectamine ® 2000 (Lip2000). Transfection efficiency is expressed as the percentage of cells expressing the mKate2 fluorescent protein and as the mKate2 fluorescence intensity normalized to the value from the control transfection with Lipofectamine ® 2000.

| LNP | % cells expressing mKate2 | Fluorescence mKate2 |
|---|---|---|
| B05 | 95.20 ± 0.84 | 13.29 ± 0.02 |
| B26 | 84.22 ± 1.18 | 0.76 ± 0.03 |
| B27 | 90.04 ± 2.43 | 1.96 ± 0.06 |
| Lip2000 | 40.70 ± 1.13 | 1.00 ± 0.03 |

Example 28

Efficiency of mRNA Incorporation into Lipid Nanoparticles

The packaging efficiency of mRNA encoding the mKate2 fluorescent protein into mRNA-LNPs B01-B27 prepared in Example 25 was determined using a Qubit 4 RNA HS Assay Kit (Life Technologies) according to the manufacturer's protocol. The efficiency of incorporation was determined by comparing the concentration of mRNA freely available in the nanoparticle solution and the concentration of mRNA released from the nanoparticles after their decomposition. mRNA-LNPs were decomposed with buffer containing Triton X-100 (10 mM Tris-HCl, pH 8.0; 0.1 mM EDTA, 2% Triton X-100). The mRNA packaging efficiency was demonstrated, ranging from 43 to 93% (Table 8).

TABLE 8

Efficiency of packaging mRNA encoding fluorescent protein mKate2 into mRNA-LNP, including standard deviations from triplicates.

| LNP | mRNA packaging (%) |
|---|---|
| B01 | 92.59 ± 2.79 |
| B02 | 82.30 ± 2.20 |
| B03 | 90.94 ± 0.55 |
| B04 | 93.18 ± 0.77 |
| B05 | 80.86 ± 2.31 |
| B06 | 83.74 ± 0.24 |
| B07 | 76.49 ± 6.16 |
| B08 | 81.22 ± 1.33 |
| B09 | 67.51 ± 6.27 |
| B10 | 78.33 ± 0.79 |
| B11 | 92.3 ± 4.4 |
| B12 | 88.3 ± 1.0 |
| B13 | 78.3 ± 7.0 |
| B14 | 60.8 ± 2.8 |
| B15 | 62.2 ± 4.2 |
| B16 | 64.3 ± 1.4 |
| B17 | 65.9 ± 7.3 |
| B18 | 65.3 ± 3.8 |

TABLE 8-continued

| Efficiency of packaging mRNA encoding fluorescent protein mKate2 into mRNA-LNP, including standard deviations from triplicates. | |
|---|---|
| LNP | mRNA packaging (%) |
| B19 | 83.6 ± 1.8 |
| B20 | 43.4 ± 5.8 |
| B21 | 54.8 ± 2.8 |
| B22 | 66.3 ± 9.8 |
| B23 | 64.2 ± 1.7 |

Example 29

Cellular Toxicity of mRNA-LNP

A human cell line derived from embryonic kidney cells (HEK293), the same line expressing SV40 large T antigen (HEK293T), human osteosarcoma-derived cell line (U2OS), and human hepatocyte carcinoma cell line (HepG2) were cultured in 96-well plates ($5\times10^4$ cells in 100 µl of culture medium per well) in Dulbecco's modified medium (DMEM) or in IMDM medium (Iscove's Modified Dulbecco's medium) supplemented with 10% foetal bovine serum (FBS) at 37° C. in 5% $CO_2$. Cells were transfected with 2 µl of mRNA-LNPs generated in triplicates in Example 25 (the final total concentration of all lipid components in the well was 20 µM) or 10 µl of mRNA-LNPs (the final total concentration of all lipid components in the well was 100 µM) and subsequently incubated for 24 hours. The cytotoxicity of LNPs was analysed in a CellTiterGlo 2.0 cell viability assay (Promega, USA). Cell viability was normalized to non-transfected cells (control). The results are summarized in Tables 9A,B and 10A,B.

When using mRNA-LNPs with a total concentration of all lipid components of 20 µM, the maximum cytotoxicity measured in the HEK293 cell line was 16%, measured for B02 and B03. No significant toxicity was demonstrated for particles B01 and B05-B23. With a 5 times higher total concentration of all lipid components of 100 µM, the trend was analogous, with the highest toxicity of 38% in B03; particles B04-B08 exhibited a cytotoxicity of approximately 20%, B09 and B10 exhibited no toxicity. Particles B11-B23 also exhibited no toxicity. In the HEK293T line, the highest cytotoxicity was measured again in B02 and B03; in other particles, the toxicity was very low. Particles with total concentrations of all lipid components of 20 µM exhibited almost no toxicity on the U2OS cell line, with a concentration of 100 µM, the highest toxicity was 35% for B10 particles. Particles formed by lipidoids 4a, 4b, 4d and 4e were non-toxic, particles formed by lipidoids 4f, 4g, 9 and 13 were very slightly toxic (Tab. 9A, Tab. 10B).

TABLE 9A

Cytotoxicity of mRNA-LNPs expressed as cell viability (%) after the addition of 20 µM transfection mixture with mRNA for individual cell line types.

| LNP | HEK293 | HEK293T | U2OS |
|---|---|---|---|
| Control | 100.00 ± 6.75 | 100.00 ± 2.34 | 100.00 ± 2.65 |
| B01 | 98.15 ± 1.00 | 95.54 ± 0.29 | 96.51 ± 0.47 |
| B02 | 84.02 ± 1.98 | 80.75 ± 2.61 | 98.08 ± 1.38 |
| B03 | 84.62 ± 0.32 | 75.04 ± 2.58 | 90.09 ± 1.64 |
| B04 | 91.76 ± 0.45 | 89.54 ± 1.13 | 98.59 ± 0.88 |
| B05 | 98.98 ± 1.73 | 93.75 ± 2.51 | 96.45 ± 2.97 |
| B06 | 96.89 ± 4.71 | 92.70 ± 2.59 | 92.75 ± 2.53 |
| B07 | 96.91 ± 5.64 | 93.45 ± 0.94 | 92.53 ± 2.70 |
| B08 | 97.70 ± 5.13 | 95.16 ± 4.00 | 92.98 ± 4.65 |

TABLE 9A-continued

Cytotoxicity of mRNA-LNPs expressed as cell viability (%) after the addition of 20 µM transfection mixture with mRNA for individual cell line types.

| LNP | HEK293 | HEK293T | U2OS |
|---|---|---|---|
| B09 | 107.46 ± 6.15 | 84.34 ± 3.78 | 95.89 ± 1.87 |
| B10 | 97.13 ± 3.47 | 81.06 ± 2.69 | 98.92 ± 1.11 |

TABLE 9B

Cytotoxicity of mRNA-LNPs expressed as cell viability (%) after the addition of 20 µM transfection mixture with mRNA for individual cell line types.

| LNP | HEK293T | HepG2 |
|---|---|---|
| B11 | 103.8 ± 6.8 | 104.2 ± 8.4 |
| B12 | 99.3 ± 6.5 | 105.7 ± 4.5 |
| B13 | 101.5 ± 5.6 | 104.0 ± 7.6 |
| B14 | 102.3 ± 3.7 | 106.6 ± 4.8 |
| B15 | 98.9 ± 1.4 | 99.7 ± 1.9 |
| B16 | 100.7 ± 1.7 | 107.4 ± 3.3 |
| B17 | 100.2 ± 4.5 | 108.7 ± 4.9 |
| B18 | 100.2 ± 3.8 | 104.2 ± 1.3 |
| B19 | 96.6 ± 1.6 | 79.6 ± 4.2 |
| B20 | 101.7 ± 1.8 | 106.3 ± 2.4 |
| B21 | 105.6 ± 1.9 | 106.4 ± 1.2 |
| B22 | 104.3 ± 1.6 | 106.6 ± 3.0 |
| B23 | 102.9 ± 1.1 | 104.7 ± 5.0 |

TABLE 10A

Cytotoxicity of mRNA-LNPs expressed as cell viability (%) after the addition of 100 µM transfection mixture with mRNA for individual cell line types.

| LNP | HEK293 | HEK293T | U2OS |
|---|---|---|---|
| Control | 100.00 ± 6.75 | 100.00 ± 2.34 | 100.00 ± 2.65 |
| B01 | 95.98 ± 0.88 | 90.01 ± 0.24 | 94.63 ± 0.58 |
| B02 | 70.24 ± 2.90 | 65.65 ± 2.32 | 91.32 ± 2.40 |
| B03 | 62.00 ± 2.89 | 57.21 ± 2.18 | 75.64 ± 4.92 |
| B04 | 77.44 ± 1.35 | 78.14 ± 1.30 | 97.02 ± 0.73 |
| B05 | 88.00 ± 4.82 | 88.92 ± 1.39 | 96.51 ± 1.87 |
| B06 | 81.58 ± 3.97 | 83.86 ± 0.98 | 83.31 ± 1.74 |
| B07 | 87.19 ± 1.71 | 91.09 ± 1.98 | 85.02 ± 1.37 |
| B08 | 77.93 ± 14.22 | 88.46 ± 2.81 | 84.76 ± 2.16 |
| B09 | 100.44 ± 12.84 | 82.46 ± 5.08 | 84.88 ± 5.59 |
| B10 | 94.09 ± 5.58 | 86.73 ± 8.29 | 65.30 ± 7.71 |

TABLE 10B

Cytotoxicity of mRNA-LNPs expressed as cell viability (%) after the addition of 100 µM transfection mixture with mRNA for individual cell line types.

| LNP | HEK293T | HepG2 |
|---|---|---|
| B11 | 98.2 ± 3.3 | 99.7 ± 3.8 |
| B12 | 95.9 ± 3.8 | 101.6 ± 3.1 |
| B13 | 90.9 ± 4.3 | 96.3 ± 3.0 |
| B14 | 98.3 ± 0.7 | 103.8 ± 4.5 |
| B15 | 97.5 ± 0.6 | 109.9 ± 9.6 |
| B16 | 96.8 ± 3.3 | 108.5 ± 5.1 |
| B17 | 96.7 ± 2.9 | 105.1 ± 6.6 |
| B18 | 101.5 ± 5.9 | 108.2 ± 4.6 |
| B19 | 82.2 ± 1.8 | 84.4 ± 4.2 |
| B20 | 96.9 ± 4.2 | 104.5 ± 3.8 |
| B21 | 96.7 ± 1.7 | 102.3 ± 6.7 |
| B22 | 96.1 ± 3.1 | 103.1 ± 4.3 |
| B23 | 100.1 ± 4.4 | 103.6 ± 3.9 |

Example 30

Transfection of mRNA Using New LNPs In Vitro

A human cell line derived from embryonic kidney cells (HEK293), the same line expressing SV40 large T antigen (HEK293T), liver carcinoma cells (HepG2, Huh7) and a human osteosarcoma-derived cell line (U2OS), were cultured in 96-well plates ($5\times10^4$ cells in 100 µl culture medium per well) in Dulbecco's modified medium (DMEM) or in IMDM medium supplemented with 10% fetal bovine serum (FBS) at 37° C. in 5% $CO_2$. Cells were transfected with 2 µl of mRNA-LNP B01 to B05 prepared in Example 25 (final total concentration of all lipid components in the well was 20 µM) carrying mRNA encoding the fluorescent protein mKate2 and subsequently incubated for 24 hours. Lipofectamine® 2000 was used as a control transfection reagent. Transfections were performed in three biological replicates, with each biological replicate having three technical replicates. The percentage of cells expressing the mKate2 fluorescent protein and the fluorescence intensity of the mKate2 were analyzed in a BD LSR Fortessa cytometer. For fluorescence intensity, data are normalized to the commercial transfection reagent Lipofectamine® 2000.

For the HEK293 line, the percentage of cells expressing the mKate2 protein was more than 2-fold higher for all the lipidoids used than for a commercially available transfection reagent. The fluorescence intensity was more than 2× higher for all lipidoids used, with the B02 particles formed by lipidoid 4d it was 3× higher than for commercially available Lipofectamine® 2000. mRNA-LNPs formed with the new lipidoids transfected the HepG2 cell line in all cases at least 2.5 times better than commercial Lipofectamine® 2000, the fluorescence intensity for the mRNA-LNPs B03 formed with lipidoid 4c was 4.5-fold that for Lipofectamine® 2000. A similar improvement in transfection with new mRNA-LNPs compared to commercial Lipofectamine® 2000 was achieved in other cell lines (Tab. 11, Tab. 12).

TABLE 11

Transfection efficiency of new mRNA-LNPs for different cell lines expressed as a percentage of cells expressing fluorescent mKate2 protein from mRNA transfected with particles for HEK293, HepG2, HEK293T, Huh7 and U2OS lines. Statistics were evaluated by Student's unpaired t-test. The p values are always related to the control variant of Lip2000 transfection in the respective cell line; p values <0.001 are indicated with the letter "a".

| LNP | HEK293 | p | HepG2 | p | HEK293T | p | Huh7 | p | U2OS | p |
|---|---|---|---|---|---|---|---|---|---|---|
| B01 | 91.24 ± 4.25 | a | 94.57 ± 0.38 | a | — | | 97.08 ± 0.40 | a | — | |
| B02 | 96.39 ± 0.72 | a | 97.10 ± 0.70 | a | 93.10 ± 1.63 | a | — | | — | |
| B03 | 95.63 ± 0.79 | a | 96.93 ± 0.39 | a | 92.31 ± 1.56 | a | 88.23 ± 2.61 | a | 82.37 ± 1.68 | a |
| B04 | 90.57 ± 1.54 | a | 97.56 ± 0.36 | a | 93.53 ± 3.58 | a | 90.66 ± 0.79 | a | — | |
| B05 | 91.56 ± 3.02 | a | 96.42 ± 0.75 | a | 93.53 ± 3.58 | a | 96.26 ± 0.37 | a | — | |
| Lip2000 | 42.63 ± 17.56 | a | 38.10 ± 1.54 | a | 46.03 ± 1.88 | a | 64.67 ± 1.40 | a | 53.93 ± 1.93 | a |

TABLE 12

Transfection efficiency of new mRNA-LNPs for different cell lines expressed as relative fluorescence intensity of mKate2 from mRNA transfected with particles for HEK293, HepG2, HEK293T, Huh7 and U2OS lines. For fluorescence intensity, data are normalized to the commercial transfection reagent Lipofectamine ® 2000. Statistics were evaluated by Student's unpaired t-test. The p values are always relative to the control variant of Lip2000 transfection in the respective cell line; values of p <0.001 are marked with the letter "a", p <0.01 are marked with "b".

| LNP | HEK293 | p | HepG2 | p | HEK293T | p | Huh7 | p | U2OS | p |
|---|---|---|---|---|---|---|---|---|---|---|
| B01 | 2.33 ± 0.17 | a | 3.05 ± 0.22 | a | — | | 2.04 ± 0.09 | a | — | |
| B02 | 2.74 ± 0.37 | a | 2.87 ± 0.17 | a | 3.00 ± 0.47 | a | — | | — | |
| B03 | 2.92 ± 0.38 | a | 4.54 ± 0.22 | a | 3.93 ± 0.57 | a | 1.19 ± 0.08 | b | 2.07 ± 0.27 | a |
| B04 | 3.08 ± 0.21 | a | 3.93 ± 0.24 | a | 3.50 ± 0.55 | a | 1.26 ± 0.08 | a | — | |
| B05 | 2.61 ± 0.11 | a | 3.48 ± 0.32 | a | 2.87 ± 0.31 | a | 1.96 ± 0.13 | a | — | |
| Lip2000 | 1.00 ± 0.30 | a | 1.00 ± 0.11 | a | 1.00 ± 0.05 | a | 1.00 ± 0.03 | ab | 1.00 ± 0.03 | a |

Example 31

Transfection of mRNA Using New LNPs Formed by Lipidoids Modified in "Z"

Human cell line HepG2 was cultured in 96-well plates ($5\times10^4$ cells in 100 µl culture medium per well) in DMEM medium supplemented with 10% FBS at 37° C. in 5% $CO_2$. Cells were transfected with 2 µl of mRNA-LNP B11-B13 prepared in Example 25 (final total concentration of all lipid components in the well was 20 µM) and subsequently incubated for 24 hours. Lipofectamine® 2000 was used as a control transfection reagent. Transfections were performed in three biological replicates, with each biological replicate having three technical replicates. The percentage of cells expressing the mKate2 fluorescent protein and the fluorescence intensity of the mKate2 were analyzed in a BD LSR Fortessa cytometer. New mRNA-LNP with Z modified substituents of lipidoids were able to efficiently transfect the mRNA into HepG2 cell line (Tab. 13) in all cases better than control transfection reagent Lipofectamine® 2000.

TABLE 13

Transfection efficiency of new mRNA-LNPs expressed as a percentage of cells expressing fluorescent mKate2 protein and as relative fluorescence intensity of mKate2 from mRNA transfected with particles for HepG2 cell line. For fluorescence intensity, data are normalized to the commercial transfection reagent Lipofectamine ® 2000 (Lip2000). Statistics were evaluated by Student's unpaired t-test. The p values are always related to the control variant of Lip2000 transfection in the respective cell line; p values <0.001 are indicated with the letter "a".

| LNP | % cells expressing mKate2 | p | Fluorescence intensity | p |
|---|---|---|---|---|
| B11 | 97.92 ± 0.62 | a | 3.81 ± 0.51 | a |
| B12 | 95.92 ± 2.55 | a | 1.62 ± 0.34 | a |
| B13 | 95.31 ± 0.53 | a | 2.23 ± 0.26 | a |
| Lip2000 | 40.70 ± 1.13 | a | 1.00 ± 0.03 | a |

Example 32

Transfection of mRNA Using New LNPs Formed by Biodegradable Lipidoids

Human cell lines HEK293, HEK293T and U2OS were cultured in 96-well plates ($5\times10^4$ cells in 100 μl culture medium per well) in DMEM or IMDM medium supplemented with 10% FBS at 37° C. in 5% $CO_2$. Cells were transfected with 2 μl of mRNA-LNP B05, B08-B10 and B14-B23 prepared in Example 25 (final total concentration of all lipid components in the well was 20 μM) and subsequently incubated for 24 hours. Lipofectamine® 2000 was used as a control transfection reagent. Transfections were performed in three biological replicates, with each biological replicate having three technical replicates. The percentage of cells expressing the mKate2 fluorescent protein and the fluorescence intensity of the mKate2 were analyzed in a BD LSR Fortessa cytometer.

Cell lines were transfected significantly better with the new mRNA-LNPs compared to commercial Lipofectamine® 2000. Lipidoids 4e, 9, 13 and 21 had comparable effects on the percentage of cells transfected. The fluorescence intensity of the translated mRNA encoding the mKate2 protein was then always significantly increased in the HEK293 and HEK293T lines compared to commercial Lipofectamine® 2000. In the U2OS line, lipidoid 13 transfected similarly to the lipidoid 4e (Tab. 14, Tab. 15).

TABLE 14

Transfection efficiency of new mRNA-LNPs for various cell lines expressed as the percentage of cells expressing the mKate2 fluorescent protein from the mRNA transfected with the particles. HEK293, HEK293T and U2OS lines are listed. Statistics were evaluated by Student's unpaired t-test. The p values are always related to the control variant of Lip2000 transfection in the respective cell line; values of p <0.001 are marked with the letter "a".

| LNP | HEK293 | p | HEK293T | p | U2OS | p |
|---|---|---|---|---|---|---|
| B08 | 86.50 ± 0.71 | a | 95.63 ± 4.50 | a | 86.87 ± 4.72 | a |
| B09 | 87.50 ± 2.15 | a | 96.03 ± 4.79 | a | 88.65 ± 0.93 | a |
| B10 | 86.50 ± 0.71 | a | 96.83 ± 3.52 | a | 86.85 ± 2.32 | a |
| B14 | | | 92.94 ± 0.90 | a | | |
| B15 | | | 87.30 ± 1.44 | a | | |
| B16 | | | 92.81 ± 0.95 | a | | |
| B17 | | | 92.94 ± 2.50 | a | | |
| B18 | | | 92.16 ± 2.02 | a | | |
| B19 | | | 99.67 ± 0.12 | a | | |
| B20 | | | 90.23 ± 0.38 | a | | |
| B21 | | | 91.68 ± 0.53 | a | | |
| B05 | 89.20 ± 0.34 | a | 98.57 ± 0.23 | a | 90.15 ± 2.10 | a |
| Lip2000 | 36.73 ± 1.86 | a | 59.40 ± 2.78 | a | 38.87 ± 3.18 | a |

TABLE 15

Transfection efficiency of new mRNA-LNPs for various cell lines expressed as relative fluorescence intensity of mKate2 related to the Lip2000 transfection control variant. HEK293, HEK293T and U2OS lines are listed. Statistics were evaluated by Student's unpaired t-test. The p values are always related the control variant of Lip2000 transfection in the respective cell line; values of p <0.001 are marked with the letter "a", p <0.01 are marked with "b".

| LNP | HEK293 | p | HEK293T | p | U2OS | p |
|---|---|---|---|---|---|---|
| B08 | 3.11 ± 0.49 | a | 1.37 ± 0.08 | b | 1.08 ± 0.12 | b |
| B09 | 4.31 ± 0.62 | a | 1.49 ± 0.13 | a | 1.93 ± 0.05 | a |
| B10 | 2.96 ± 0.19 | a | 1.77 ± 0.26 | b | 1.06 ± 0.11 | b |
| B14 | | | 1.41 ± 0.04 | a | | |
| B15 | | | 2.51 ± 0.21 | a | | |
| B16 | | | 1.03 ± 0.14 | | | |
| B17 | | | 1.74 ± 0.29 | b | | |
| B18 | | | 1.94 ± 0.08 | a | | |
| B19 | | | 7.47 ± 0.90 | a | | |
| B05 | 8.54 ± 0.44 | a | 2.93 ± 0.15 | a | 2.14 ± 0.10 | a |
| Lip2000 | 1.00 ± 0.09 | a | 1.00 ± 0.11 | ab | 1.00 ± 0.15 | ab |

Example 33

Transfection of siRNA Using New LNPs In Vitro

LNPs containing small interfering RNA (siRNA, catalog number AM4626, Ambion) causing degradation of mRNA encoding green fluorescent protein (GFP) were prepared as follows: 300 μl of A28 transfection reagent solution prepared in Example 24 was mixed with a solution of 1.20 nmol siRNA in 300 μl 10 mM citrate buffer (pH 3.0) using a microfluidic device analogously to Example 25 The resulting siRNA-LNPs were immediately diluted in 600 μl PBS; the corresponding nanoparticles labeled B28 were thus formed from transfection reagent A28. LNPs carrying control (scrambled; 4390843, Ambion) siRNAs that do not target any endogenously cell-transcribed mRNA (B29) were prepared analogously. Lipofectamine RNAiMax (Invitrogen) was used as a control transfection reagent specifically for siRNA transfection according to the manufacturer's standard protocol. A human cell line U2OS stably expressing the green fluorescent protein (GFP) was used for siRNA-LNP knockdown. Cells were cultured in 96-well plates ($5\times10^4$ cells in 100 μl culture medium per well) in DMEM medium supplemented with 10% FBS at 37° C. in 5% $CO_2$. Cells were transfected with 2 μl of siRNA-LNP, the final total concentration of all lipid components in the well was 20 μM; final siRNA concentration was 16 nM) and subsequently incubated for 24 hours. Transfections were performed in three biological replicates. The percentage of cells expressing the green fluorescent protein GFP and the fluorescence intensity of the GFP were analyzed in a BD LSR Fortessa cytometer.

With the new siRNA-LNPs (B28), a decrease in GFP expression was observed down to 1% of GFP-expressing cells; with commercial RNAiMax, GFP expression was still detected in 13.6% of cells. The fluorescence intensity of GFP when using the new siRNA-LNPs (B28) decreased by 1.25-fold compared to the commercial RNAiMax reagent (Tab. 16).

TABLE 16

Reduction in GFP-encoding mRNA in the U2OS cell line by siRNA-LNP (B28) expressed as a percentage of GFP-expressing cells and GFP fluorescence intensity compared to the commercial transfection reagent RNAiMAx and siRNA-LNP carrying control siRNA (B29). Statistics were evaluated by Student's unpaired t-test. The p values are related to the B28 transfection mixture tested; values of p <0.001 are marked with the letter "a", p <0.01 are marked with "b".

| LNP | % cells expressing GFP | p | GFP fluorescence intensity | p |
|---|---|---|---|---|
| Control | 82.30 ± 1.60 | | 0.86 ± 0.02 | |
| B28 | 1.00 ± 0.30 | a | 0.26 ± 0.03 | ab |
| B29 | 83.60 ± 0.90 | a | 0.92 ± 0.06 | a |
| RNAiMax | 13.60 ± 1.20 | a | 0.32 ± 0.03 | b |

siRNA-LNPs containing small interfering RNA (siRNA, catalog number 4392420, Ambion) causing the degradation of mRNA encoding tyrosyl-DNA phosphodiesterase 2 (TDP2) were prepared in the same manner as B28 particles in this example. The corresponding nanoparticles designated B30 were thus formed from the transfection reagent A28. LNPs carrying control (scrambled; 4390843, Ambion) siRNAs that do not target any endogenously cell-transcribed mRNA (B29) were also used as a control. Lipofectamine RNAiMax (Invitrogen) was used as a control transfection reagent specifically for siRNA transfection. The human cell line HEK293 and two lines derived from human multiple myeloma, which are very difficult to transfect with available transfection reagents, were used for siRNA-LNP knockdown (Brito J. L. R., Brown N., Morgan G. J. (2010) Transfection of siRNAs in Multiple Myeloma Cell Lines. In: Min W P., Ichim T. (eds) RNA Interference. Methods in Molecular Biology (Methods and Protocols), vol 623. Humana Press). Cells were cultured in 96-well plates ($5 \times 10^4$ cells in 100 μl culture medium per well) in DMEM medium supplemented with 10% FBS at 37° C. in 5% $CO_2$. Cells were transfected with 2 μl siRNA-LNP (with a final total concentration of all lipid components of 20 μM and a final concentration of siRNA of 16 nM) and subsequently incubated for 24 hours. Transfections were performed in three biological replicates. RNA was isolated with an RNAeasy Plus Micro Kit (Qiagen). The cDNA was prepared with TATAA GrandScript cDNA Supermix (TATAAbiocenter) according to the manufacturer's recommendations. Quantitative RT-PCR was performed in a LightCycler 480 (Roche Life Science). The primers for amplifying mRNA encoding TDP2 were as follows: 5'-CGAGAGGAGGGTCTCAAAGAG-3' (SEQ ID NO. 3) and 5'-ATTTCGGGAAGGCTGCTGTC-3' (SEQ ID NO. 4). mRNA encoding GAPDH was used to normalize the data (Primers: 5'-AATCCCATCACCATCTTCCA-3' (SEQ ID NO. 5) and 5'-TGGACTCCACGACGTACTCA-3' (SEQ ID NO. 6)).

In all these cases, the new siRNA-LNPs significantly reduced the level of TDP2 mRNA in cells compared to the commercial transfection reagent RNAiMax. In the HEK293 cell line it was 2.86-fold, in the OPM-2 myeloma line 4.3-fold, and in the RPMI8226 myeloma line 6.7-fold compared to a commercial reagent for siRNA transfection (Tab. 17).

TABLE 17

Reduction of endogenously expressed TDP2 mRNA levels in cells by new siRNA-LNPs (B30) compared to the commercial transfection reagent RNAiMax and compared to control siRNA-LNPs (B29) in the HEK293, OPM-2 and RPMI8226 cell lines. Statistics were evaluated by Student's unpaired t-test. The p values are related to the B30 transfection mixture tested; p values <0.001 are indicated with the letter "a".

| LNP | HEK293 | p | OPM-2 | p | RPMI8226 | p |
|---|---|---|---|---|---|---|
| Control | 1.00 ± 0.10 | | 1.00 ± 0.01 | | 1.00 ± 0.03 | |
| B30 | 0.03 ± 0.01 | a | 0.14 ± 0.02 | a | 0.13 ± 0.00 | a |
| B29 | 0.99 ± 0.17 | a | 1.09 ± 0.01 | a | 0.78 ± 0.01 | a |
| RNAiMax | 0.09 ± 0.01 | a | 0.58 ± 0.02 | a | 0.87 ± 0.11 | a |

Example 34

Transfection of Plasmid DNA Using New LNPs In Vitro

LNPs containing 4706 bp plasmid DNA (Evrogen, Cat. No. FP181) encoding the mKate2 fluorescent protein were prepared as follows: 300 μl of the A28 transfection reagent solution prepared in Example 24 was mixed with a solution of 120 μg of plasmid DNA in 300 μl of 10 mM citrate buffer (pH 3.0) using a microfluidic device analogously to Example 25. The resulting DNA-LNPs were immediately diluted in 600 μl PBS; the corresponding nanoparticles designated B31 were thus formed from transfection reagent A28. Transfections were performed on the human cell line HEK293T. Cells were cultured in 96-well plates ($5 \times 10^4$ cells in 100 μl culture medium per well) in DMEM medium supplemented with 10% FBS at 37° C. in 5% $CO_2$. Cells were transfected with 2 μl of DNA-LNP (with a final total concentration of all lipid components of 20 μM) and subsequently incubated for 24 hours. Lipofectamine® 2000 (Lip2000, Invitrogen) was used as a control transfection reagent. Transfections were performed in three biological replicates, with each biological replicate having three technical replicates. The percentage of cells expressing the mKate2 fluorescent protein and the fluorescence intensity of the mKate2 were analyzed in a BD LSR Fortessa cytometer.

The percentage of cells expressing the fluorescent protein mKate2 was 3.8-fold higher with the new DNA-LNPs compared to the commercial transfection reagent. The fluorescence intensity was 2.9 times higher than with the commercial reagent (Tab. 18).

TABLE 18

Transfection efficiency of new DNA-LNPs (B31) compared to commercial Lipofectamine ® 2000 (Lip2000) in the HEK293T cell line expressed as % of mKate2-expressing cells and as mKate2 fluorescence intensity. For fluorescence intensity, data are normalized to the commercial transfection reagent Lipofectamine ® 2000. Statistics were evaluated by Student's unpaired t-test. Values of p <0.001 are indicated with the letter "a".

| LNP | % cells expressing mKate2 | p | mKate2 fluorescence intensity | p |
|---|---|---|---|---|
| B31 | 91.16 ± 0.98 | a | 2.93 ± 0.36 | a |
| Lip2000 | 24.30 ± 1.00 | a | 1.00 ± 0.07 | a |

Example 35

Transfection of mRNA with New LNPs into Human Primary Hepatocytes

The gene encoding the NanoLuc bioluminescent protein was amplified from plasmid pET51b(+)_S-Luc_CLIP (Addgene, Cat. No. 113923; obtained as a gift from Kai Johnsson) using the primers: (5'-TAATACGACTCACTATAGGG-'3 (SEQ ID NO. 7); 5'-GCTAGTTATTGCTCAGCGG-3' (SEQ ID NO. 8)). Messenger RNA (mRNA) was prepared in vitro analogously to Example 25 and packaged into LNP as follows: A 300 μl sample of transfection reagent A28, and 120 μg of mRNA in 300 μl of 10 mM citrate buffer (pH 3.0) were assembled into LNP using a microfluidic device analogously to Example 25. The resulting mRNA-LNPs were immediately diluted in 600 μl PBS; the corresponding nanoparticles labeled B32 were thus formed from transfection reagent A28. Primary hepatocytes were isolated from a human donor according to a published protocol (LeCluyse, E. L.: *Methods in Molecular Biology* 2005; 290, 207-230). Cells were transfected with 2 μl of mRNA-LNP (with a final total concentration of all lipid components of 20 μM) and incubated for 24 hours. Lipofectamine® 2000 transfection reagent was used as a control. Substrate in the Nano-Glo® Luciferase Assay System kit (Promega) was then added to the cells and the luminescence intensity was analyzed in a Microplate Reader: Infinite® M1000 PRO (Tecan).

The new mRNA-LNPs efficiently transfected human primary hepatocytes, with a significant 2.0-fold increase in luminescence compared to the non-transfected control (Tab. 19).

TABLE 19

Transfection efficiency of new mRNA-LNPs (B32) in the primary line of human hepatocytes compared to the commercial transfection reagent Lipofectamine ® 2000 expressed as bioluminescence intensity normalized to the value from control transfection. Statistics were evaluated by Student's unpaired t-test. Values of $p < 0.05$ are indicated with the letter "c").

| LNP | bioluminescence intensity | p |
|---|---|---|
| B32 | 1.97 ± 0.60 | c |
| Lip2000 | 1.00 ± 0.12 | c |

Example 36

Transfection of Cyclic Dinucleotides with New LNPs In Vitro

The cyclic dinucleotide (2',3'-cGAMP) (Sigma, cat. No. SML1229-0.5UMO) was packaged in LNP as follows: 300 μl samples of A01-A06 transfection reagents, and 120 nmol of cGAMP in 300 μl of 10 mM citrate buffer (pH 3.0) were added to the LNP using a microfluidic device analogous to Example 25. The resulting cGAMP-LNPs were immediately diluted in 600 μl PBS; samples of nanoparticles designated B33-B38 were thus formed from the corresponding transfection reagents A01-A06. A reporter assay showing the degree of induction of the interferon response by the cyclic dinucleotide cGAMP depending on the STING pathway was used to analyse the efficiency of cGAMP-LNP particle transfection. For this purpose, a cell reporter line HEK293T expressing the common type of STING protein and a luciferase reporter gene under the IRF3 interferon-stimulated (ISRE) promoter were used according to Novotná et al. (Novotná, B.: *J. Med. Chem.* 2019, 62 (23), 10676-10690). Cells were transferred to poly-D-lysine (Sigma-Aldrich)-coated 96-well plates (Greiner Bio-One) at a density of $2.5\times10^4$ in DMEM medium containing glucose (containing L-glutamine; Biowest) supplemented with 10% FBS (Capricorn Scientific) and 1% penicillin-streptomycin (Biowest). After incubation at 37° C. in 5% $CO_2$ overnight, serially diluted compounds were added to the cells for 7 hours. In parallel, HEK293T cells were incubated with the test compounds alone for 30 minutes, washed twice with fresh medium, and then cultured for an additional 6.5 hours. Finally, 50 μl of cell culture medium was mixed with 30 μl of Bright-Glo Luciferase Assay System reagent (Promega) in white 96-well plates and luminescence was read in a Spark® spectrophotometer (TECAN, Grodig). Values of 50% effective concentration ($EC_{50}$) were calculated using GraphPad Prism (La Jolla) as described in Novotná et al. (Novotná, B.: *J. Med. Chem.* 2019, 62 (23), 10676-10690) (Tab. 20).

The cyclic dinucleotide 2',3'cGAMP exhibited $EC_{50}$ values of STING activation±30 μM. All new cGAMP-LNPs formed by ionizable lipidoids 4a-4f efficiently transfected HEK293T cells and activated STING in the nanomolar region, increasing transfection efficiency approximately 2000-15000×. The most effective was lipidoid 4d, exhibiting an $EC_{50}$ of 2.00±0.36 nM.

TABLE 20

$EC_{50}$ values of STING activation for 2',3'-cGAMP transfected with new cGAMP-LNPs (B33-B38) formed by ionizable lipidoids 4a-4f.

| LNP | $EC_{50}$ STING activation (nM) |
|---|---|
| B33 | 9.00 ± 1.75 |
| B34 | 12.00 ± 1.80 |
| B35 | 10.00 ± 6.42 |
| B36 | 2.00 ± 0.36 |
| B37 | 4.00 ± 1.12 |
| B38 | 14.00 ± 2.61 |

Example 37

Toxicity of New mRNA-LNPs In Vivo

Messenger RNA (mRNA) encoding NanoLuc protein was prepared and packaged into particles analogously to Example 35. The resulting mRNA-LNPs (B32) were administered intraperitoneally to three C57Bl/6 mice (BIOCEV, Vestec) at a concentration of 0.5 mg mRNA/kg, wherein three control C57Bl/6 mice were administered PBS intraperitoneally. Another three C57Bl/6 mice were administered mRNA-LNP at a 5-fold higher concentration (2.5 mg mRNA/kg) in the same manner. Similarly, identical doses of mRNA-LNPs were again administered to 3 C57Bl/6 mice (0.5 mg mRNA/kg) and 3 C57Bl/6 mice (2.5 mg mRNA/kg) intravenously, and the animals were anesthetized prior to the administration (2.5 mg/mouse ketaminum, 0.4 mg/mouse xylazinum, Bioveta). Mice were then observed for 48 hours and none showed any signs of toxicity or phenotypic changes compared to control animals.

Example 38

Biodistribution of New mRNA-LNPs In Vivo

Figure 7:
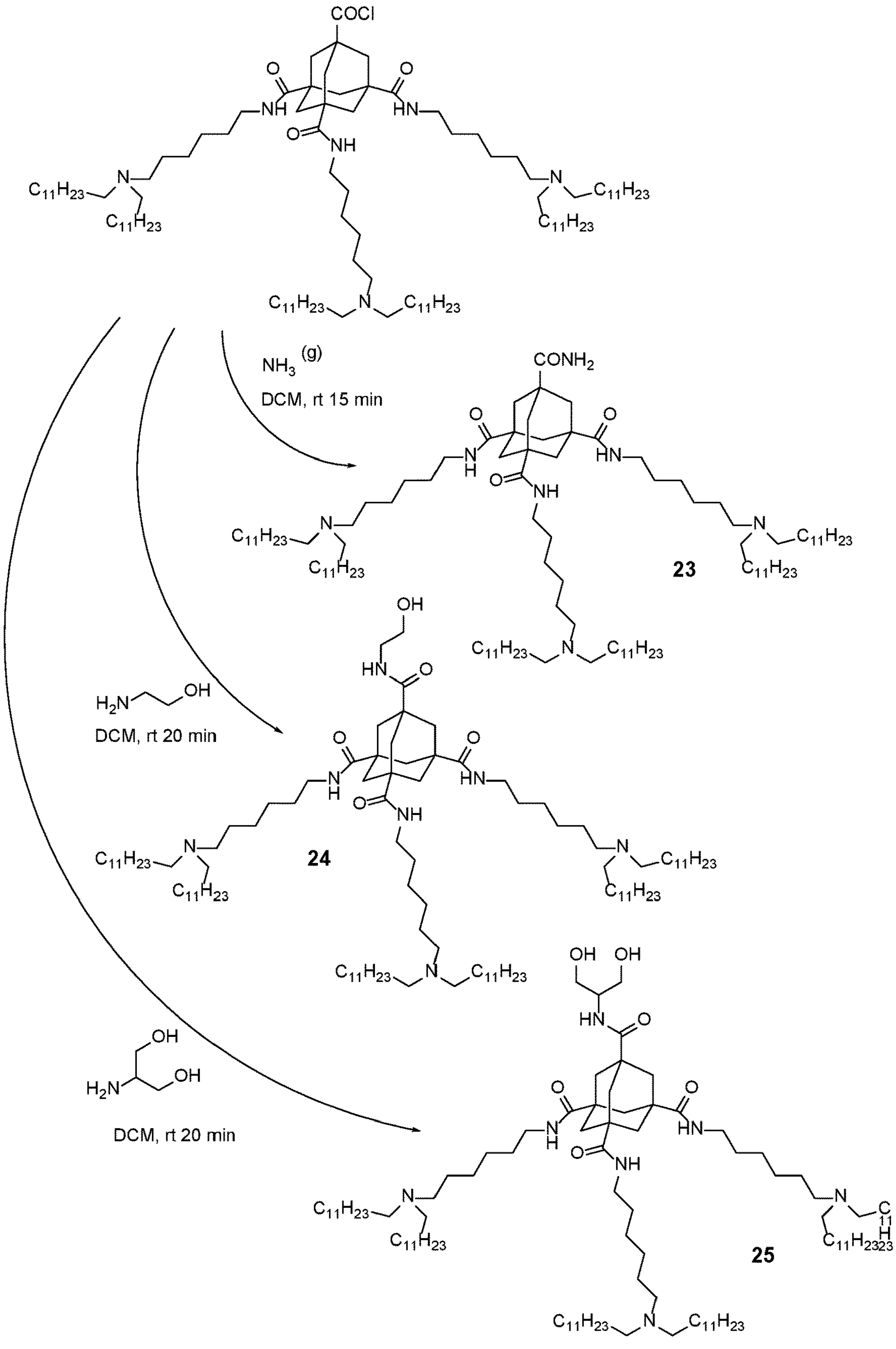
FIG. 7. Synthetic scheme of lipidoids 23-25.
Figure 8:
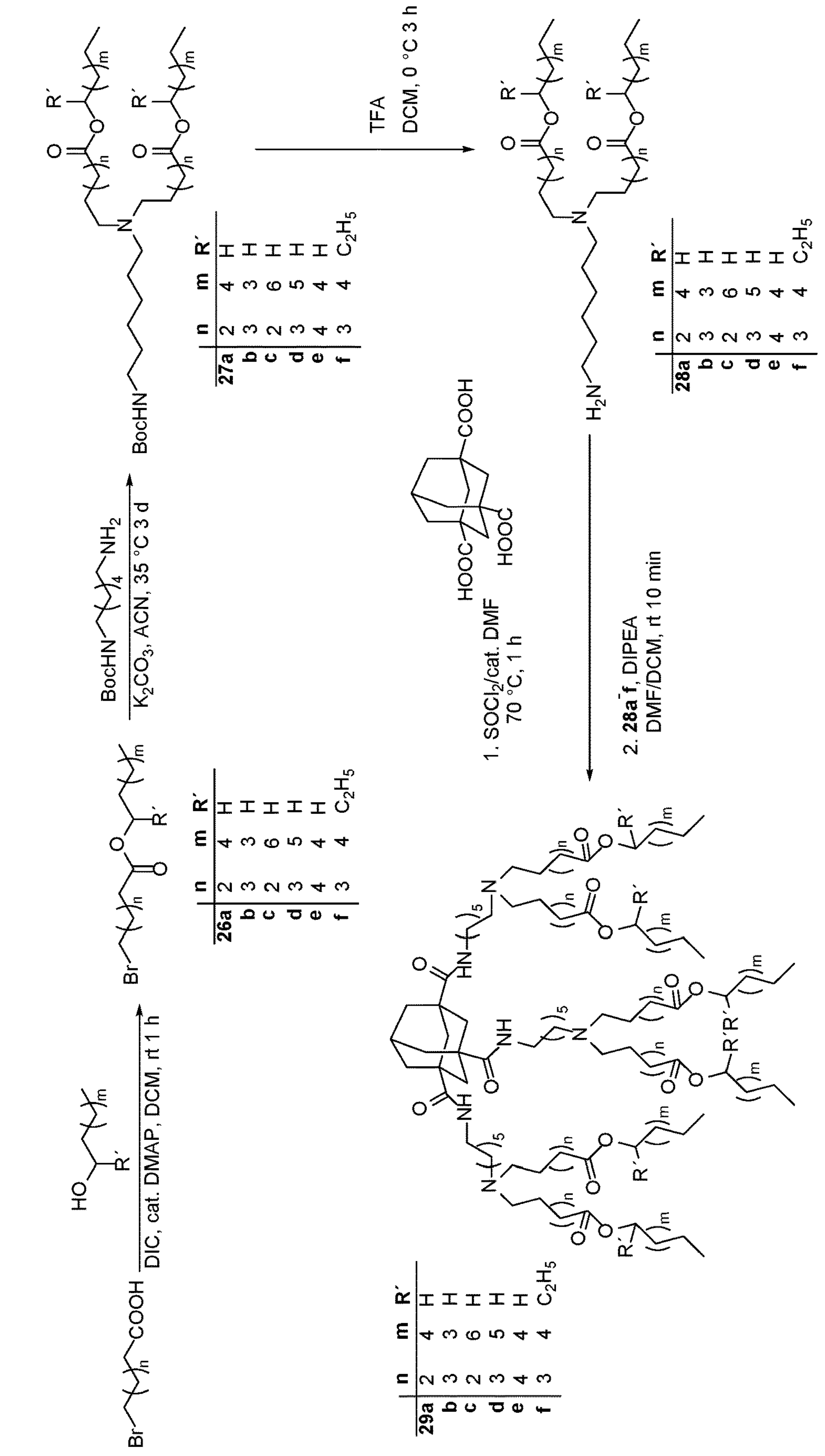
FIG. 8. Synthetic scheme of lipidoids 29a-f
Figure 9:
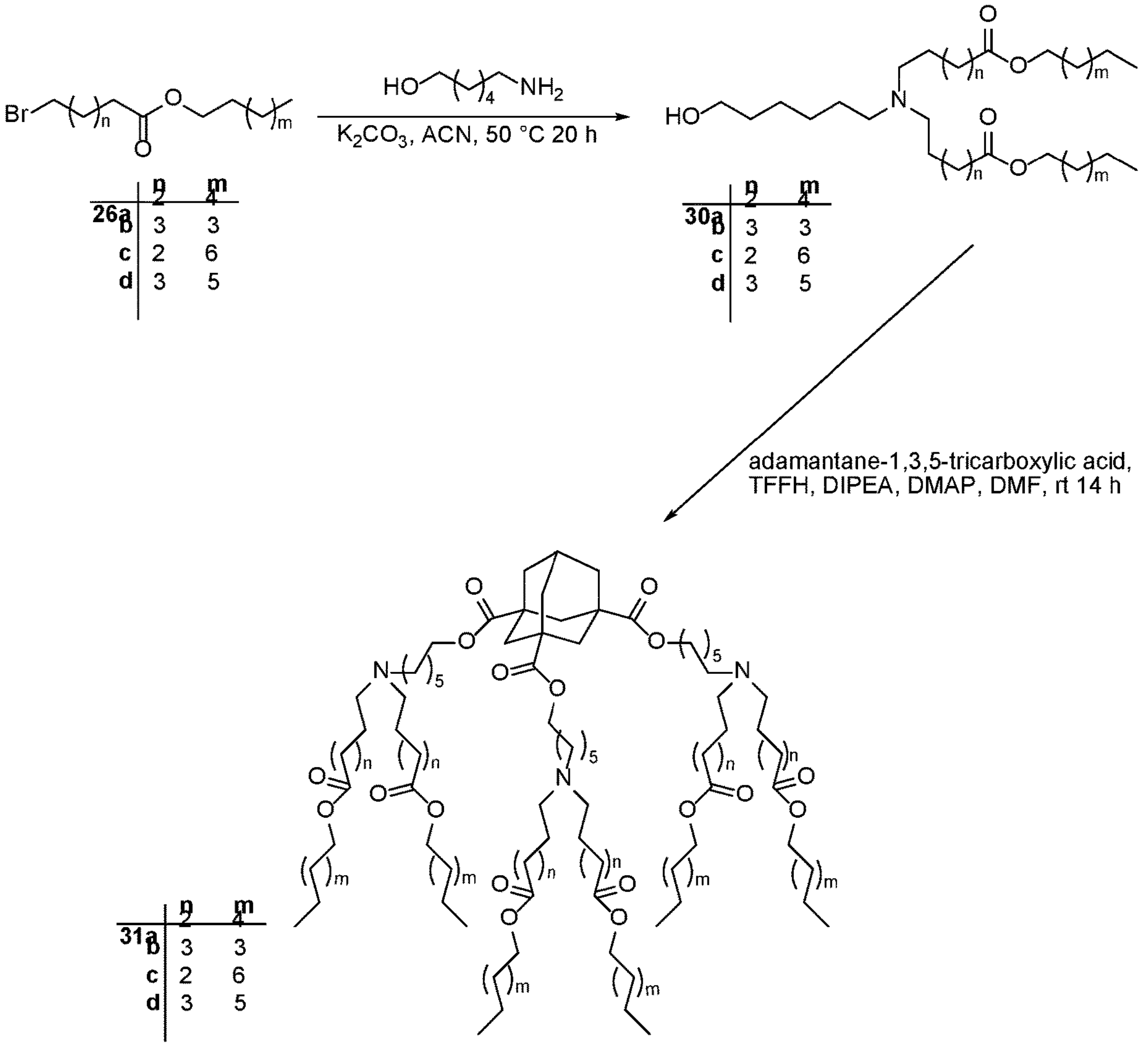
FIG. 9. Synthetic scheme of lipidoids 31a-d.
Figure 10:
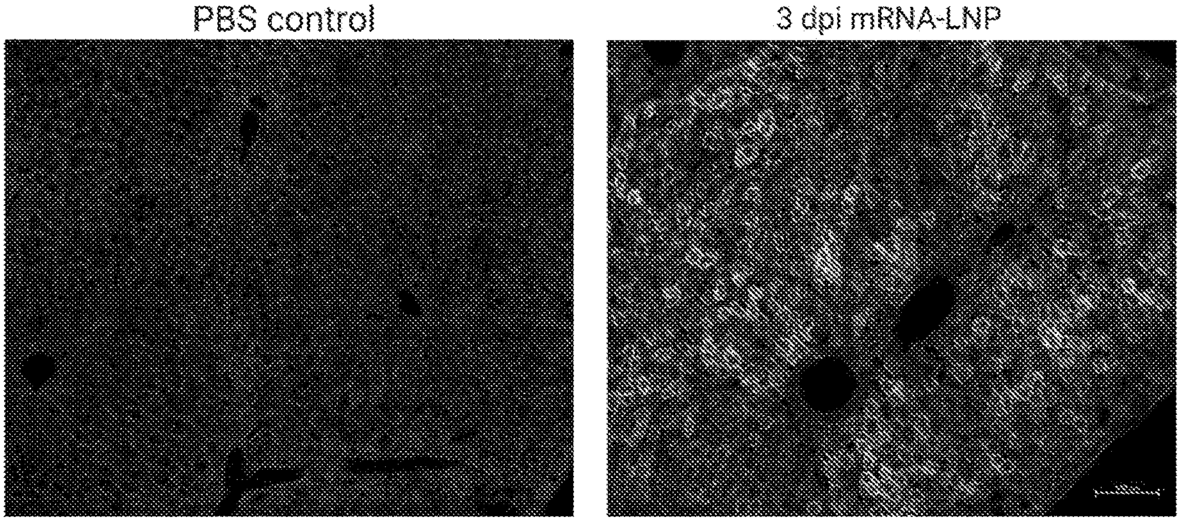
FIG. 10. Test of functional delivery of mRNA-LNP (B39) to murine liver.

The gene encoding the CRE recombinase protein was amplified from the plasmid pCAG-Cre-IRES2-GFP (Addgene, catalog number 26646, donated by Anjen Chenn) using the primers: (5'-TAATACGACTCACTATAGAATT-TACT-'3 (SEQ ID NO. 9); 5'-CTAATCGC-CATCTTCCAGCA-3' (SEQ ID NO. 10)). Messenger RNA (mRNA) was prepared in vitro analogously to Example 25 and packaged into LNP as follows: A 300 µl sample of transfection reagent A28, and 120 µg of mRNA in 300 µl of 10 mM citrate buffer (pH 3.0) were assembled into LNP using a microfluidic device analogously to Example 25. The resulting mRNA-LNPs were immediately diluted in 600 µl PBS; the corresponding nanoparticles labeled B39 were thus formed from transfection reagent A28. mRNA-LNPs (B39) were administered intravenously at a concentration of 0.5 mg mRNA/kg to 2.5 mg mRNA/kg in each case to 3 mice with a global dual Cre reporter (Mazumdar, M. D.: *Genesis* 2007, 45:593-605) (breeding BIOCEV, Vestec) enabling the analysis of successful recombination. In the cells to which mRNA-LNPs carrying Cre recombinase mRNA were successfully delivered, chromosomal recombination and subsequent excision of the membrane red protein gene (so-called red tomato) and "turning on" the transcription of membrane green protein (GFP) gene occurred. Mice, including non-particulate control mice, were sacrificed 3 days after particulate application, and all organs were subjected to histological analysis according to a standardized protocol. Histological images show a complete distribution of particles into the liver, which led to a 30-50% conversion of cells expressing the red membrane protein to cells expressing the green membrane protein 3 days after application (FIG. 7). In FIG. 7, histological images of liver show the conversion of cells expressing the red membrane protein to cells expressing the green membrane protein 3 days after application of the mRNA-LNPs [2.5 mg/kg of mRNA] encoding Cre recombinase (labeled as "3 dpi mRNA-LNP"). "PBS control"-injection of PBS buffer only.

Example 39

Stability of New mRNA-LNPs and siRNA-LNPs at 4° C.

Human cell line HEK293T was cultured in 96-well plates ($5\times10^4$ cells in 100 µl culture medium per well) in DMEM medium supplemented with 10% FBS at 37° C. in 5% $CO_2$. Cells were transfected with 2 µl of mRNA-LNP B05, prepared in Example 25 (final total concentration of all lipid components in the well was 20 µM) and subsequently incubated for 24 hours. The B05 mRNA-LNPs were stored at 4° C. and transfections were analogously repeated one, three and five weeks after assembly. Transfections were performed in triplicates. The fluorescence intensity of the mKate2 was analyzed in a BD LSR Fortessa cytometer.

Transfection efficiency of the new mRNA-LNPs (labelled B05) remained unchanged for at least three weeks and decreased to 81% compared to Day 1, while stored at 4° C. (Tab. 21).

TABLE 21

Transfection efficiency of B05 mRNA-LNPs stored at 4° C. for HEK293 cells expressed as relative fluorescence intensity of mKate2. Data normalized to fluorescence intensity measured at Day 1 after assembly. Five weeks later, the B05 mRNA-LNPs still kept 81% of transfection efficiency while stored at 4° C.

| Time | Fluorescence of mKate2 |
|---|---|
| 1 day | 1.00 ± 0.17 |
| 1 week | 1.14 ± 0.26 |
| 3 weeks | 1.04 ± 0.16 |
| 5 weeks | 0.81 ± 0.11 |

siRNA-LNPs (labelled B30 and B40) containing small interfering RNA (siRNA, catalog number 4392420, Ambion) causing the degradation of mRNA encoding tyrosyl-DNA phosphodiesterase 2 (TDP2) were prepared in the same manner as described in Example 33 and were stored at 4° C. siRNA-LNPs B40 were formed from transfection reagent A29 prepared in Example 24. HEK293T cells were cultured in 96-well plates ($5\times10^4$ cells in 100 µl culture medium per well) in DMEM medium supplemented with 10% FBS at 37° C. in 5% $CO_2$. Cells were transfected with 2 µl siRNA-LNPs (with a final total concentration of all lipid components of 20 µM and a final concentration of siRNA of 16 nM) and subsequently incubated for 24 hours. Transfections were performed in triplicates. RNA isolation, cDNA preparation and qRT-PCR were performed as described in Example 33. The whole procedure was repeated one, two and three months after the LNP assembly.

The transfection efficacy of the new siRNA-LNPs (labelled B30 and B40) expressed as their ability to reduce the level of TDP2 mRNA in cells remained practically unchange while stored at 4° C. for three months (Tab. 22).

TABLE 22

Relative level of TDP2 mRNA in HEK293T cells after transfection of siRNA-LNPs stored at 4° C. at respective time points.

| Time | B30 | B40 |
|---|---|---|
| 1 day | 0.0380 ± 0.0107 | 0.0336 ± 0.0079 |
| 1 month | 0.0700 ± 0.0036 | 0.0817 ± 0.0100 |
| 2 months | 0.0423 ± 0.0026 | 0.0492 ± 0.0037 |
| 3 months | 0.0387 ± 0.0067 | 0.0646 ± 0.0164 |

Example 40

Transfection of siRNA by Preformed Empty LNPs

Transfection reagents A28 and A29 from Example 24 were used to assemble empty nanoparticles B41 and B42 in citrate buffer excluding nucleic acid analogously to Example 25, with no post-dilution. One µl of LNPs was mixed with 1 pmol of siRNA targeting TDP2 10 minutes prior to transfection, analogously as recommended for Lipofectamine RNAiMax, and incubated at room temperature. HEK293T and HepG2 cells ($5\times10^4$ cells in 100 µl culture medium per well) were transfected with the mixture of preassembled LNPs and siRNA and incubated for 24 hours. Transfections were performed in triplicates. Lipofectamine RNAiMax was used as a control transfection reagent. Preassembled LNPs subsequently mixed with 1 pmol of siRNA were able to knock down TDP2 mRNA expression by 90-97%, both significantly better then commercial transfection reagent Lipofectamine RNAiMax (Tab. 23).

TABLE 23

Reduction of TDP2 mRNA levels in cells by preassembled empty LNPs mixed with siRNA targeting TDP2 compared to commercial transfection reagent RNAiMax. Statistics were determined by Student's unpaired t-test. P values are related to control transfection with Lipofectamine RNAiMax, values $p < 0.001$ are indicated by letter "a", values $p < 0.01$ are indicated by letter "b".

| LNP | HEK293T | p | HepG2 | p |
|---|---|---|---|---|
| Control | 1.00 ± 0.25 | | 1.00 ± 0.08 | |
| B41 | 0.03 ± 0.01 | a | 0.10 ± 0.03 | b |
| B42 | 0.07 ± 0.01 | b | 0.08 ± 0.01 | a |
| RNAiMax | 0.12 ± 0.03 | ab | 0.18 ± 0.01 | ab |

Example 41

Transfection of Peripheral Blood Mononuclear Cells (PBMC) by siRNA-LNPs and Evaluation of Cytokine Response Transfection reagent A28 from Example 24 was used to form siRNA-LNP designated B43 containing siRNA causing the degradation of mRNA encoding Poly(U)-binding-splicing factor (PUF60). The siRNA-LNPs were prepared analogously as in Example 33. Lipofectanime RNAiMax was used as a control transfection reagent. Peripheral blood mononuclear cells (PBMC) from 3 anonymous blood donors (with the agreement number 13/06/2012 of ethical committee of the Institute of Hematology and Blood Transfusion, Prague, Czech Republic) were isolated by Ficoll (Ficoll® Paque Plus, 17-1440-02, GE Healthcare) gradient and cultured in RPMI medium supplemented with 10% of FBS and 50 U/ml of penicillin/streptomycin. Cells were seeded at $10^5$ cells/100 ul (200 ul in total) in 96-well plates and incubated at 37° C. The ON-target plus SMARTpool siRNA targeting PUF60 were purchased from Dharmacon (catalogue number L-012505-01-0005; llkirch, France) and resuspended in water at 20 pmol/ul. The final concentrations of 1 pmol or 10 pmol were used. Each condition was performed in triplicate. 24 hours after transfection the cells were harvested including the supernatant. Total RNA was extracted using Nucleospin RNA extraction kit (Macherey Nagel) following manufacture's instruction. Reverse transcription was performed with 500 ng of RNA. Quantitative RT-PCR was performed in a LightCycler 480 (Roche Life Science) in duplicate using the SYBERGREEN mix. The primers for amplifying PUF60 were as follows: 5-CCTTCAACCGCATCTACGTG-3 (SEQ ID NO. 7) and 5-CTGGGCCTTCTCGTACTCAA-3 (SEQ ID NO. 8). RPLPO was used to normalize the data (Primers: 5-CACCATTGAAATCCTGAGTGATG-3 (SEQ NO. 9) and 5-TGACCAGCCCAAAGGAGAAG-3 (SEQ NO. 10)). The quantities of total IFN-α and IFN-γ produced by PBMC after transfections were measured in cell-free supernatants using human ELISA kits (Human IFN-α ELISABASIC kit (HRP), 3425-1H-20, Mabtech and Human IFN-λ1 ELISABASIC kit, 3570-1H-20, Mabtech). 24 hours treatment of PBMC with 1 μM CpG ODN 2216 Class A (Invivogen) was used as a positive control.

In all cases, the siRNA-LNPs reduced the level of PUF60 mRNA in PBMC cells (Tab. 24) without upregulating the cytokine response as opposed to RNAiMax (Tab. 25 and Tab. 26).

TABLE 24

Reduction of endogenously expressed PUF60 mRNA levels in PBMC by new siRNA-LNPs (B43) compared to the transfection reagent RNAiMax and compared to non-treated cells.

| LNP | Donor 1 | Donor 2 | Donor 3 |
|---|---|---|---|
| Non treated | 1.00 ± 0.23 | 1.00 ± 0.34 | 1.00 ± 0.18 |
| B43 [1 pmol of siRNA] | 0.55 ± 0.04 | 0.12 ± 0.20 | 0.65 ± 0.32 |
| B43 [10 pmol of siRNA] | 0.40 ± 0.14 | 0.50 ± 0.02 | 0.07 ± 0.03 |
| RNAiMax [1 pmol of siRNA] | 0.51 ± 0.08 | 1.15 ± 0.01 | 0.62 ± 0.40 |
| RNAiMax [10 pmol of siRNA] | 0.21 ± 0.20 | 0.29 ± 0.30 | 0.22 ± 0.10 |

TABLE 25

IFN-α response of PBMC after treatment of siRNA-LNPs compared to RNAiMax.

| LNP | Donor 1 | Donor 2 | Donor 3 |
|---|---|---|---|
| Non treated | 2.38 ± 2.06 | 0.44 ± 0.56 | 0.00 ± 0.00 |
| Positive control | 533 ± 13 | 661 ± 58 | 2265 ± 29 |
| B43 [1 pmol of siRNA] | 0.00 ± 0.00 | 1.52 ± 1.54 | 0.00 ± 0.00 |
| B43 [10 pmol of siRNA] | 0.00 ± 0.00 | 0.00 ± 0.00 | 16.8 ± 20.1 |
| RNAiMax [1 pmol of siRNA] | 0.00 ± 0.00 | 6.05 ± 8.58 | 0.65 ± 1.12 |
| RNAiMax [10 pmol of siRNA] | 433 ± 251 | 1814 ± 243 | 1951 ± 31 |

TABLE 26

IFN-λ response of PBMC after treatment of siRNA-LNPs compared to RNAiMax.

| LNP | Donor 1 | Donor 2 | Donor 3 |
|---|---|---|---|
| Non treated | 2.49 ± 2.34 | 2.99 ± 2.75 | 37.9 ± 7.4 |
| Positive control | 713 ± 67 | 1765 ± 180 | 1000 ± 52 |
| B43 [1 pmol of siRNA] | 0.00 ± 0.00 | 0.00 ± 0.00 | 20.4 ± 2.7 |
| B43 [10 pmol od siRNA] | 11.7 ± 20.2 | 0.00 ± 0.00 | 40.7 ± 4.2 |
| RNAiMax [1 pmol of siRNA] | 0.00 ± 0.00 | 0.00 ± 0.00 | 44.5 ± 13.2 |
| RNAiMax [10 pmol of siRNA] | 28.7 ± 49.8 | 100 ± 59 | 706 ± 188 |

Example 42

Effectivity of siRNA-LNPs In Vivo

Transfection reagent A29 from Example 24 was used to form siRNA-LNPs designated as B44 with siRNA targeting mouse apolipoprotein B (ApoB) gene, a hepatocyte-expressed gene involved in cholesterol transport (ApoB) (catalogue number 238055 Apob mouse siPOOL-40 kit, siTOOLs Biotech GmbH) and alternatively siRNA-LNPs (B45) with control non-targeted siRNA-LNPs (enclosed in 238055 Apob mouse siPOOL-40 kit, siTOOLs Biotech GmbH), assembled as described in Example 33. The siRNA-LNPs were dialyzed to PBS. The endotoxin levels were <2 EU/ml. Mice were fasted for 4 hours before plasma collection by retroorbital bleed. The siRNA-LNPs targeting ApoB were administered intravenously to 5 C57Bl/6 mice (BIOCEV, Czech Center of Phenogenomics, Vestec) at a concentration of 32 μg of siRNA and 16 μg of siRNA, respectively, wherein the control 5 mice were administered with 32 μg of non-targeting siRNA-LNPs and another 5 mice were administered PBS control. All mice were sacrificed 2 days after LNP application. Plasma levels of cholesterol, triglycerides and LDL-C were measured by using automated systems at the Czech Center of Phenogenomics according to standardized protocol.

Clinical biochemistry of plasma markers such as total cholesterol, triglycerides and LDL-C, affected by ApoB knock down, were significantly decreased compared to control animals, demonstrating thus the efficient delivery of ApoB siRNA by novel LNPs into the liver (Tab. 27).

TABLE 27

Clinical biochemistry of plasma markers indicating efficient ApoB knockdown in the liver. Statistics were evaluated by Student's unpaired t-test. The p1 values are always relative to the control mice injected with PBS; the p2 values are always relative to the mice injected with B45 LNP with control non-targeted siRNA; values of p <0.001 are marked with the letter "a", p <0.01 are marked with "b".

| LNP | Total cholesterol | p1 | p2 | Triglycerides | p1 | p2 | LDL-C | p1 | p2 |
|---|---|---|---|---|---|---|---|---|---|
| Control | 1.99 ± 0.34 | a | | 0.46 ± 0.12 | ab | | 0.39 ± 0.04 | a | |
| B44 [16 μg] | 0.43 ± 0.18 | a | a | 0.18 ± 0.03 | a | a | 0.15 ± 0.05 | a | a |
| B44 [32 μg] | 0.35 ± 0.13 | a | a | 0.19 ± 0.03 | b | a | 0.13 ± 0.03 | a | a |
| B45 [32 μg] | 2.58 ± 0.61 | | a | 0.53 ± 0.04 | | a | 0.84 ± 0.12 | | a |

Example 43

Effectivity of Nucleoside-Modified mRNA-LNPs In Vivo

The gene encoding the CRE recombinase protein was amplified from the plasmid pCAG-Cre-IRES2-GFP (Addgene, catalog number 26646, donated by Anjen Chenn) using the primers: (5'-TAATACGACTCACTATAGAATTTACT-'3 (SEQ ID NO. 9); 5'-CTAATCGCCATCTTCCAGCA-3' (SEQ ID NO. 10)). Messenger RNA (mRNA) was prepared in vitro analogously to Example 25, with the exception that CTP was 100% exchanged for 5-Methyl-CTP (NU-1138L, Biogen Praha s.r.o.) and UTP was 100% exchanged for N1-Methylpseudo-UTP (NU-890L, Biogen Praha s.r.o.), and packaged into LNP as follows: A 300 μl sample of transfection reagent A28, and 120 μg of mRNA in 300 μl of 10 mM citrate buffer (pH 3.0) were assembled into LNP using a microfluidic device analogously to Example 25. The resulting mRNA-LNPs were immediately diluted in 600 μl PBS; the corresponding nanoparticles labeled B46 were thus formed from transfection reagent A28. mRNA-LNPs (B46) were administered intravenously at a concentration of 0.5 mg mRNA/kg to 2.5 mg mRNA/kg in each case to 3 mice with a global dual Cre reporter (Mazumdar, M. D.: *Genesis* 2007, 45:593-605) (breeding BIOCEV, Vestec) enabling the analysis of successful recombination. In the cells to which mRNA-LNPs carrying Cre recombinase mRNA were successfully delivered, chromosomal recombination and subsequent excision of the membrane red protein gene (so-called red tomato) and "turning on" the transcription of membrane green protein (GFP) gene occurred. Mice, including non-particulate control mice, were sacrificed 3 days after particulate application, and all organs were subjected to histological analysis according to a standardized protocol. Histological images show a complete distribution of particles into the liver, which led to a 35-75% conversion of cells expressing the red membrane protein to cells expressing the green membrane protein 3 days after application.

The invention claimed is:

1. Compounds of general formula I

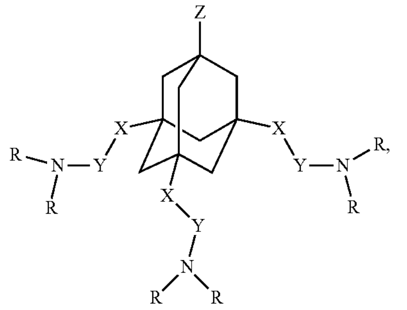

(I)

wherein X is selected from a group consisting of —C(=O)NH—, —C(=O)O—, —C(=S)O—, —C(=O)S—, —C(=S)S—, —C(=O)NHNH—, —$CH_2$—, —O—, —OC(=O)—, —S—, —SC(=O)—, —NH—, —NHNH—, —NHC(=O)—, —NHNHC(=O)—, —C≡C—, —CH=CH—, a five-membered heterocycle containing at least 2 nitrogen atoms, —$CH_2$C(=O)NH—, —$CH_2$C(=O)O—, —$CH_2$C(=S)O—, —$CH_2$C(=S)S—, —$CH_2$C(=O)NHNH—, —N=CH—, and —CH=N—;

Y is independently selected from the group consisting of $C_2$-$C_{10}$ alkylene chains wherein in the alkylene chain, one or more —$CH_2$— groups may optionally be replaced with one or more 0 or S atoms;

Z is selected from the group consisting of hydrogen, —OH, —$CH_2$OH, —$NH_2$, —$N^+(CH_3)_2$—$(CH_2)_3$—$SO_3^-$, —$N^+(CH_3)_2$—$(CH_2)_2$—COO—, and —$NHCH_3$, —$N(CH_3)_2$, —$N^+(CH_3)_3$, —$OCH_3$, —$OCH_2CH_3$, —C(=O)$R^1$, wherein $R^1$ is selected from —$NH_2$, —$NH(CH_2)_n$OH, —N$[(CH_2)_n$OH$]_2$, —NHCH$(CH_2OH)_2$, —$NHCH_2$CH(—OH)$CH_2$OH, —NH($CH_2$) C(=O)$NH_2$, —N$[CH_2C(=O)NH_2]_2$, —NHCH$[C(=O)NH_2]_2$, —$NH(CH_2)_2$NHC(=O)$NH_2$,

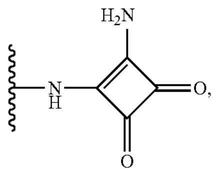

and

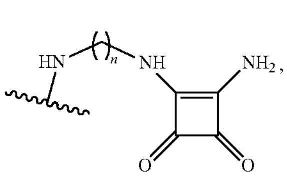

, wherein n is an integer within the range from 2 to 5;

and R are the same or different from each other, each R being independently selected from the group consisting of $C_8$-$C_{20}$ alkyl, $C_8$-$C_{20}$ alkenyl, and $C_8$-$C_{20}$ alkynyl, wherein in the alkyl, alkenyl or alkynyl, one or more —$CH_2$— groups may optionally be replaced with one or more groups selected from —CH(OH)—, —OC(=O)—, —C(=O)O—, —S—S—, —C(=O)NH—, —NHC(=O)—, —O—, and —S—;

and pharmaceutically acceptable salts, addition salts and solvates thereof.

2. The compound according to claim 1, wherein Z is selected from a group consisting of hydrogen, —OH, —$CH_2$OH, —$NH_2$, —N'$(CH_3)_2$—$(CH_2)_3$—$SO_3^-$, —$N^+(CH_3)_2$—$(CH_2)_2$—COO—, and —C(=O)$R^1$, wherein $R^1$ is selected from —$NH_2$, —$NH(CH_2)_n$OH, —N$[(CH_2)_n$OH$]_2$, —NHCH$(CH_2OH)_2$, —$NHCH_2$CH(OH)$CH_2$OH, —$NH(CH_2)_n$C(=O)$NH_2$, —N$[CH_2C(=O)NH_2]_2$, —NHCH$[C(=O)NH_2]_2$, —$NH(CH_2)_2$NHC(=O)$NH_2$,

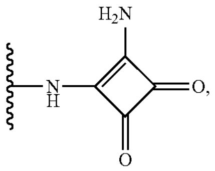

and

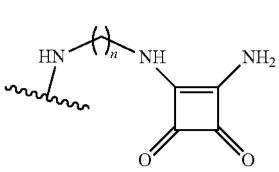

, wherein n is an integer within the range from 2 to 5.

3. The compound according to claim 1, wherein X is selected from —C(=O)NH—, a five membered heterocycle containing at least 2 nitrogen atoms, or —C(=O)O—.

4. The compound according to claim 1, wherein R is independently selected from the group consisting of $C_8$-$C_{20}$ alkyl, $C_8$-$C_{20}$ alkenyl, and $C_8$-$C_{20}$ alkynyl, wherein in the said alkyl, alkenyl or alkynyl, one or more —$CH_2$— groups may optionally be replaced by one or more groups selected from —CH(OH)—, —OC(=O)—, and —C(=O)O—.

5. The compound according to claim 1, wherein all R in the molecule are the same, or all nitrogen atoms in the molecule are substituted identically by two identical R or two different R.

6. A transfection agent comprising at least one compound of general formula I according to claim 1 in an amount of 10 to 50 mol. %, and at least one helper lipid in a total amount of 50 to 90 mol. %.

7. A transfection agent comprising at least one compound of general formula I according to claim 1 in an amount of 15 to 30 mol. %, cholesterol in an amount of 30 to 55 mol. %, and at least one further helper lipid in an amount of 20 to 50 mol. %.

8. A transfection particle comprising at least one compound of general formula I according to claim 1, at least one nucleic acid and/or a part thereof and/or nucleic acid derivative, and at least one helper lipid.

9. A method of treatment comprising the step of administering the compound of general formula I according to claim 1 for in vitro transfection of cells or tissues with nucleic acid and/or a part thereof and/or nucleic acid derivative to a subject in need thereof.

10. The method of treatment according to claim 9 for silencing or activating at least one chromosomal gene(s), silencing or activating immunogens, inhibiting or activating signaling pathways, editing genome or transcriptome, or enabling the expression of at least one protein(s) encoded by the nucleic acid.

11. The compound of general formula I according to claim 1 for transfecting cells or tissues with nucleic acid and/or a part thereof and/or nucleic acid derivative in vivo, preferably except for the transfection of human embryos for industrial or commercial purposes and except for the modification of a human germ line.

12. The compound of general formula I according to claim 1 for silencing or activating chromosomal genes(s), silencing or activating immunogens, inhibiting or activating signaling pathways, editing genome or transcriptome, or enabling the expression of the protein(s) encoded by the nucleic acid.

13. A method of administering a medicament, comprising the step of administering the compound of general formula I according to claim 1 for gene therapy.

14. A method of treatment of administering the compound of general formula I according to claim 1 in cosmetic preparations for delivering an active ingredient to the site of action to a subject in need thereof.

* * * * *

SEQUENCE LISTING

```
<160> NUMBER OF SEQ ID NOS: 10

<210> SEQ ID NO 1
<211> LENGTH: 23
<212> TYPE: DNA
<213> ORGANISM: artificial
<220> FEATURE:
<223> OTHER INFORMATION: primer

<400> SEQUENCE: 1

atcaacatat ggtgagcgag ctg                                              23


<210> SEQ ID NO 2
<211> LENGTH: 26
<212> TYPE: DNA
<213> ORGANISM: artificial
<220> FEATURE:
<223> OTHER INFORMATION: primer

<400> SEQUENCE: 2

aagaattcct atcatctgtg ccccag                                           26


<210> SEQ ID NO 3
<211> LENGTH: 21
<212> TYPE: DNA
<213> ORGANISM: artificial
<220> FEATURE:
<223> OTHER INFORMATION: primer

<400> SEQUENCE: 3

cgagaggagg gtctcaaaga g                                                21
```

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
atttcgggaa ggctgctgtc 20

<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
aatcccatca ccatcttcca 20

<210> SEQ ID NO 6
<211> LENGTH: 20
<212> TYPE: DNA
<213> ORGANISM: artificial
<220> FEATURE:
<223> OTHER INFORMATION: primer

<400> SEQUENCE: 6
tggactccac gacgtactca 20

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
taatacgact cactataggg 20

<210> SEQ ID NO 8
<211> LENGTH: 19
<212> TYPE: DNA
<213> ORGANISM: artificial
<220> FEATURE:
<223> OTHER INFORMATION: primer

<400> SEQUENCE: 8
gctagttatt gctcagcgg 19

<210> SEQ ID NO 9
<211> LENGTH: 26
<212> TYPE: DNA
<213> ORGANISM: artificial
<220> FEATURE:
<223> OTHER INFORMATION: primer

<400> SEQUENCE: 9
taatacgact cactatagaa tttact 26

<210> SEQ ID NO 10
<211> LENGTH: 20
<212> TYPE: DNA
<213> ORGANISM: artificial
<220> FEATURE:

-continued

<223> OTHER INFORMATION: primer

<400> SEQUENCE: 10
ctaatcgcca tcttccagca 20